United States Patent
Boger

(10) Patent No.: US 10,975,101 B2
(45) Date of Patent: Apr. 13, 2021

(54) ULTRA-POTENT VINCA ALKALOIDS: ADDED MOLECULAR COMPLEXITY FURTHER DISRUPTS THE TUBLIN DIMER-DIMER INTERFACE

(71) Applicant: The Scripps Research Institute, LaJolla, CA (US)

(72) Inventor: Dale Boger, LaJolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/305,357

(22) PCT Filed: May 30, 2017

(86) PCT No.: PCT/US2017/035027
§ 371 (c)(1),
(2) Date: Nov. 28, 2018

(87) PCT Pub. No.: WO2017/210206
PCT Pub. Date: Dec. 7, 2017

(65) Prior Publication Data
US 2020/0317696 A1  Oct. 8, 2020

Related U.S. Application Data

(60) Provisional application No. 62/343,490, filed on May 31, 2016.

(51) Int. Cl.
*C07D 519/04* (2006.01)
*A61P 35/00* (2006.01)
*A61P 35/02* (2006.01)

(52) U.S. Cl.
CPC ............ *C07D 519/04* (2013.01); *A61P 35/00* (2018.01); *A61P 35/02* (2018.01)

(58) Field of Classification Search
CPC ......... C07D 519/04; A61P 35/00; A61P 35/02
See application file for complete search history.

(56) References Cited

U.S. PATENT DOCUMENTS

| 8,940,754 B2 | 1/2015 | Boger |
| 9,611,271 B2 | 4/2017 | Boger |
| 10,689,381 B2 | 6/2020 | Boger |

OTHER PUBLICATIONS

International Search Report for WO 2017/210206.
Written Opinion for WO 2017/210206.
Proc Natl Acad Sci, USA, 113(35):9691-9698 (Aug. 30, 2016).
Proc Natl Acad Sci, USA, 113(35):9691-9698 (Aug. 30, 2016), Supplemental Information.

*Primary Examiner* — Noble E Jarrell
(74) *Attorney, Agent, or Firm* — Husch Blackwell LLP

(57) ABSTRACT

Synthetically-derived and previously inaccessible modifications of 20'-hydroxy-vinca derivative compounds such as vinblastine, vincristine or vindesine are disclosed that are a stunning 100-fold more active than the natural product ($IC_{50}$'s 50-75 pM vs 7 nM, HCT116), and are now accessible as a result of advances in the total synthesis of the natural product. Illustrative new ultra-potent vinblastines bind tubulin with much higher affinity and likely further disrupt the tubulin head-to-tail α/β dimer-dimer interaction by virtue of the strategic placement of an added conformationally well-defined, rigid and extended C20'-urea along the adjacent protein-protein interface. Added molecular complexity was used to markedly enhance target binding and functional biological activity, and represents a general approach to improving the properties of other natural products targeting a protein-protein interaction. A pharmaceutical composition containing an ultra-potent 20'-hydroxy-vinca derivative compound and a method of treating cancerous cells with such a compound are also disclosed.

21 Claims, No Drawings

ULTRA-POTENT VINCA ALKALOIDS: ADDED MOLECULAR COMPLEXITY FURTHER DISRUPTS THE TUBLIN DIMER-DIMER INTERFACE

CROSS-REFERENCE TO RELATED APPLICATION

This application claims priority to U.S. application Ser. No. 62/343,490, filed on May 31, 2016, whose disclosures are incorporated herein by reference.

STATEMENT REGARDING FEDERALLY SPONSORED RESEARCH OR DEVELOPMENT

This invention was made with government support under CA115526 and CA042056 awarded by the National Institutes of Health. The Government has certain rights in the invention.

TECHNICAL FIELD

The invention contemplates vinca anticancer agents and to their use. More particularly, the invention relates to derivatives of 20'-hydroxy-vinca derivative compounds that exhibit about 100-fold enhanced potency as compared to vinblastine in inhibiting microtubulin assembly and in vitro inhibition of cancer cell proliferation.

BACKGROUND ART

Vinca alkaloids, originally isolated from the periwinkle plant [*Vinca rosea* Linn., now *Cantharanthus roseus* (L.) G. Don] are a family of indole-indoline dimeric compounds that contain a four-ring system containing an indole linked to a five-ring system containing an indoline. Two of those natural alkaloids, vinblastine and vincristine, are important clinical agents in the treatment of leukemias, lymphomas and testicular cancer. The semi-synthetic vinca alkaloid, vindesine (deacetyl vinblastine carboxamide) is used to treat lung cancer and acute leukemia and less often for melanoma, and breast cancer. [*Goodman & Gilman's The Pharmaceutical Basis of Therapeutics*, Hardman et al. Eds., 9th ed., McGraw-Hill, 1257-1260, 1996].

These three vinca alkaloids each include a 20'-hydroxyl group through which they can each be chemically altered to introduce a new substituent group. The compounds contemplated herein can be viewed as derivatives of these 20'-hydroxyl vinca alkaloids and are referred to collectively herein as 20'-hydroxy-vinca derivative compounds for convenience. Structural formulas for these three compounds are illustrated below.

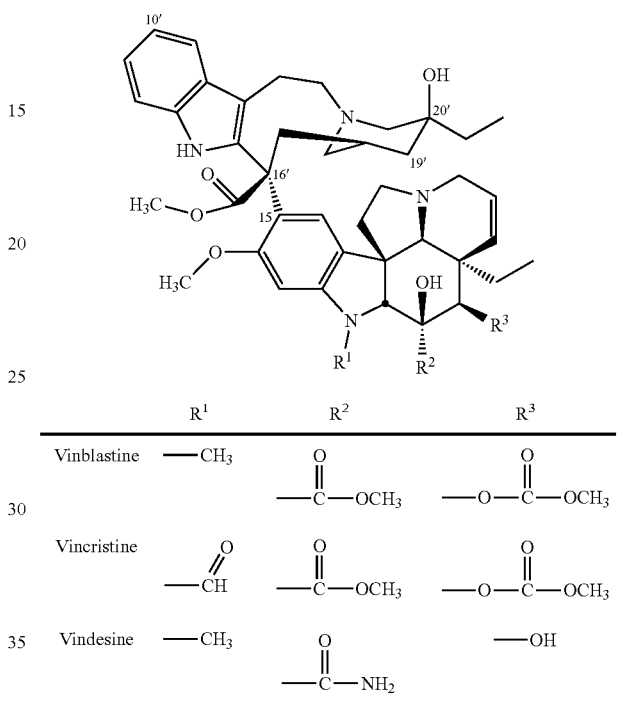

Vinblastine and vincristine are superb clinical drugs successfully used alone and in combination therapies for treatment of cancer with $IC_{50}$ values for several 20'-substituted vinblastines shown below. [For a comprehensive review of the chemistry, medicinal chemistry, biology, and clinical

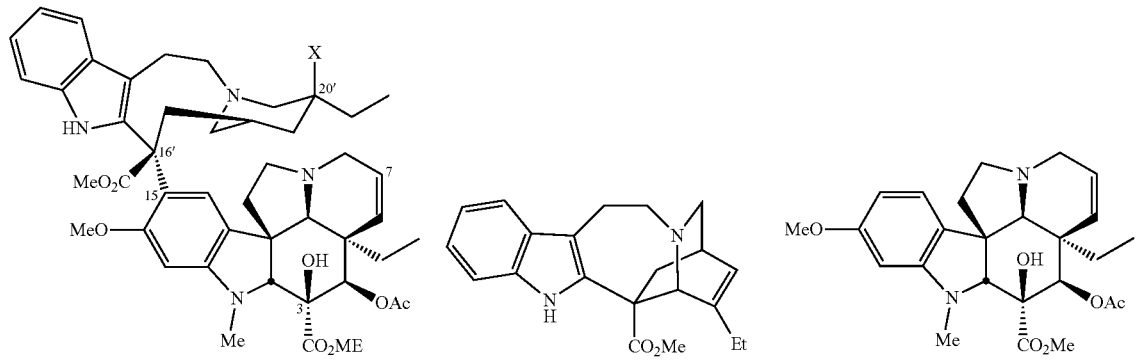

| compound | HCT116 | HCT116/VM46 |
|---|---|---|
| 1, X = OH | 6.8 | 600 |
| 4, X = H | 60 | 600 |
| 5, X = $N_3$ | 690 | 5500 |

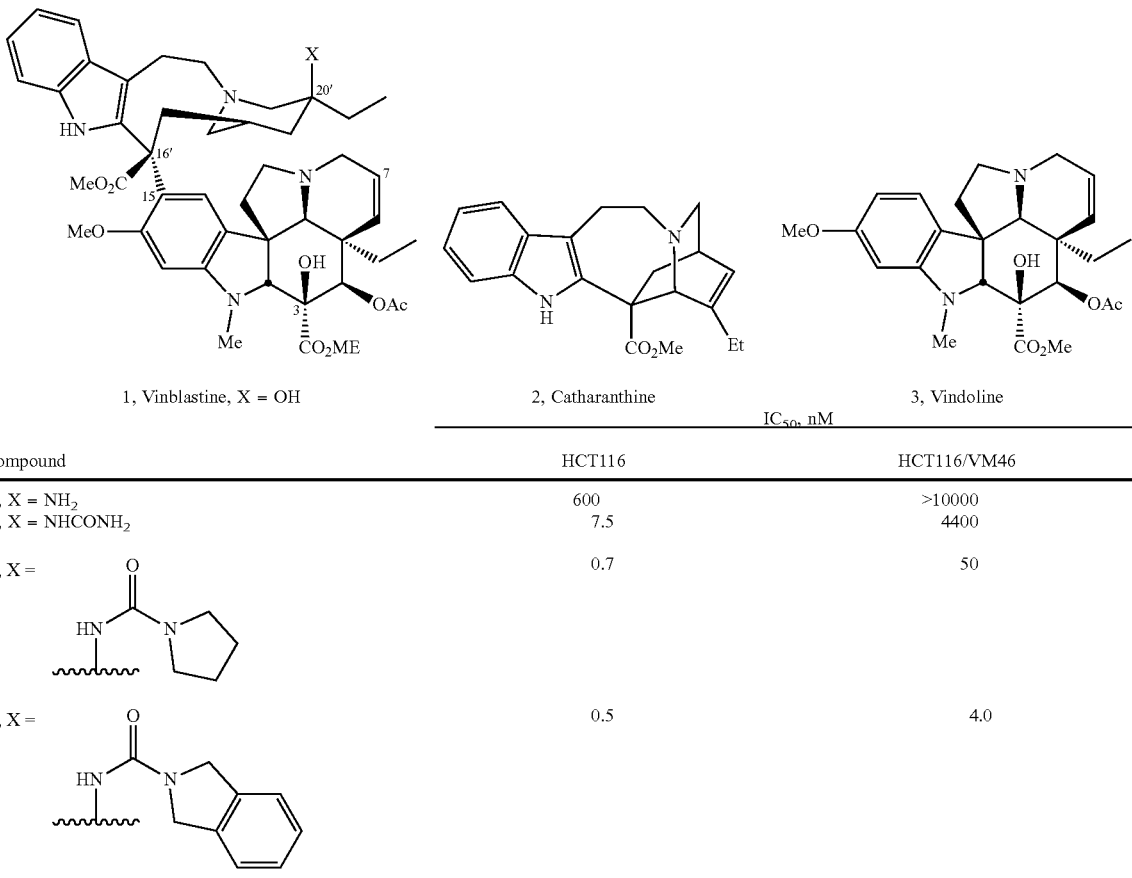

| compound | 1, Vinblastine, X = OH | 2, Catharanthine | 3, Vindoline |
|---|---|---|---|
| | | IC$_{50}$, nM | |
| | HCT116 | | HCT116/VM46 |
| 6, X = NH$_2$ | 600 | | >10000 |
| 7, X = NHCONH$_2$ | 7.5 | | 4400 |
| 8, X = 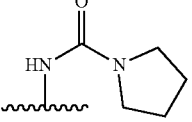 | 0.7 | | 50 |
| 9, X = 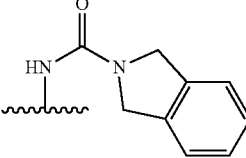 | 0.5 | | 4.0 | applications, see: (a) Kuehne et al., In *The Alkaloids*; Brossi, A., Suffness, M., Eds.; Academic: San Diego, 1990, 37, 77-131; (b) Borman et al., In *The Alkaloids*; Brossi, A., Suffness, M., Eds.; Academic: San Diego, 1990, 37, 133-144; (c) Pearce, In *The Alkaloids*; Brossi, A., Suffness, M., Eds.; Academic: San Diego, 1990, 37, 145-204; (d) Neuss et al., In *The Alkaloids*; Brossi, A., Suffness, M., Eds.; Academic: San Diego, 1990, 37, 229-240. Vinblastine is used in frontline therapies for treatment of Hodgkin's disease, testicular cancer, ovarian cancer, breast cancer, head and neck cancer, and non-Hodgkin's lymphoma, whereas vincristine is used in the curative treatment regimens for childhood lymphocytic leukemia and Hodgkin's disease. Originally isolated from the leaves of *Catharanthus roseus* (L) G. Don (periwinkle), [(a) Nobel et al., *Ann. N.Y. Acad. Sci.* 1958, 76, 882; (b) *Noble Lloydia* 1964, 27, 280; (c) Review: Nobel *Biochem. Cell Biol.* 1990, 68, 1344; and Svoboda et al., *J. Am. Pharm. Assoc., Sci. Ed.* 1959, 48, 659] vinblastine and vincristine were among the first small molecules shown to bind tubulin and to inhibit microtubule formation and mitosis, defining an oncology drug target central to one of the most successful mechanisms of action still pursued today. [Reviews: (a) Timasheff et al., *Cellular Pharmacol.* 1993, 1, S27; (b) Jordan et al., *Nat. Rev. Cancer* 2004, 4, 253.] Vindesine also acts similarly in inhibiting microtubule assembly and inhibiting cell proliferation in culture [Jordan et al., *Cancer Res* 1985, 45, 2741]. As a result, they continue to be extensively studied due to interest in their complex dimeric alkaloid structures, their role in the discovery of tubulin as an effective oncology drug target, and their clinical importance. [Reviews: (a) Potier, *Nat. Prod.* 1980, 43, 72; (b) Kutney, *Nat. Prod. Rep.* 1990, 7, 85; (c) Fahy, *Curr. Pharm. Design* 2001, 7, 1181; and (d) Sears et al., *Acc. Chem. Res.* 2015, 48, 653.]

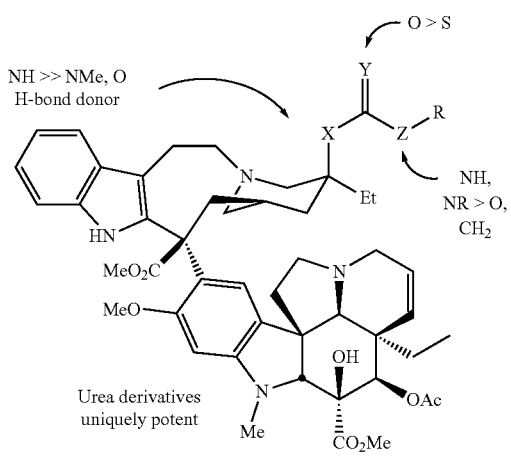

In the development of a total synthesis of vinblastine and vincristine, the inventor and co-workers introduced an Fe(III)/NaBH$_4$-mediated free radical oxidation of the anhydrovinblastine trisubstituted alkene for penultimate installation of the C20' tertiary alcohol found in the natural products. [(a) Ishikawa et al., *J. Am. Chem. Soc.* 2008, 130, 420;

(b) Ishikawa et al., *J. Am. Chem. Soc.* 2009, 131, 4904; and (c) Gotoh et al., *J. Am. Chem. Soc.* 2012, 134, 13240.] This now powerful hydrogen atom transfer- (HAT-) initiated free radical reaction was subsequently developed to provide a general method for functionalization of alkenes through use of a wider range of free radical traps [a) Leggans et al., *Org. Lett.* 2012, 14, 1428; and (b) Barker et al., *J. Am. Chem. Soc.* 2012, 134, 13588] beyond $O_2$ (air) and was explored specifically for the purpose of providing the late-stage, divergent [(a) Boger et al., *J. Org. Chem.* 1984, 49, 4050; and (b) Mullican et al., *J. Org. Chem.* 1984, 49, 4033] preparation of vinblastine analogues that bear alternative C20' functionality at a site previously inaccessible for systematic exploration (Scheme 1). [(a) Leggans et al., *Org. Lett.* 2012, 14, 1428; and (b) Barker et al., *J. Am. Chem. Soc.* 2012, 134, 13588.]

provided compounds 100-fold less potent than vinblastine, the conversion of the amine (6) to a C20' urea (7) provided a compound with cell growth inhibition activity equal to vinblastine (Table, above). [(a) Leggans et al., *Org. Lett.* 2012, 14, 1428; and (b) Barker et al., *J. Am. Chem. Soc.* 2012, 134, 13588.]

As a result, key structural features of such ureas that contribute to their activity, including the importance of the H-bond donor site on the a C20' nitrogen substituent were identified in subsequent studies. [Leggans et al., *J. Med. Chem.* 2013, 56, 628.] A trend in activity was additionally defined where substitution of the urea terminal nitrogen improves the differential in activity of the derivatives against matched sensitive and resistant tumor cell lines ($NR_2$>NHR>$NH_2$), discovered a series of potent disubstituted C20' ureas (e.g., 8 and 9) that displayed further Scheme 1

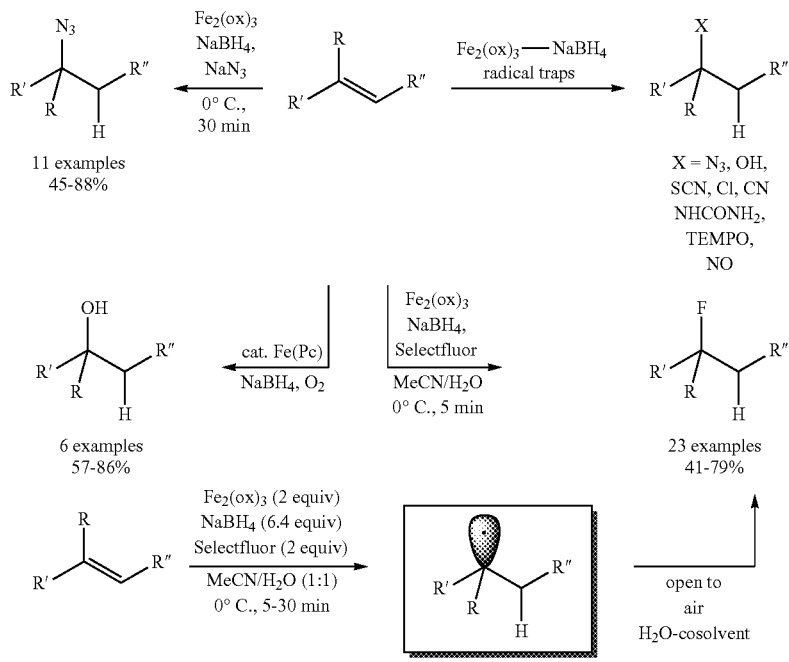

In addition to the alternative free radical traps that were introduced, the broad alkene substrate scope was defined, the exclusive Markovnikov addition regioselectivity was established, the outstanding functional group tolerance was revealed, a range of Fe(III) salts and initiating hydride sources were examined and utilized, its unique free radical reaction mechanism refined, and remarkably mild reaction conditions (0-25° C., 5-30 minutes, $H_2O$/co-solvent) were introduced that are relatively insensitive to the reaction parameters.

Although the vinblastine C20' site and its hydroxyl substituent were known to be important, the prior exploration of C20' substituent effects had been limited to a handful of alcohol acylation reactions, the removal of the C20' hydroxyl group, and a specialized set of superacid-mediated functionalizations. [Borman et al., In *The Alkaloids*; Brossi, A., Suffness, M., Eds.; Academic: San Diego, 1990, 37, 133-144] Additional studies permitted systematic changes at C20' where it was initially demonstrated that while incorporation of a C20' azide (5) or its reduced amine (6)

improved activity against resistant tumor cell lines, and established that sterically demanding C20' ureas were surprisingly well tolerated. [Leggans et al., *J. Med. Chem.* 2013, 56, 628; and Barker et al., *ACS Med. Chem. Lett.* 2013, 4, 985.]

The target of vinblastine is the tubulin α/β dimer-dimer interface where its binding destabilizes microtubulin assembly derived from the repetitive head-to-tail tubulin binding. [Reviews: (a) Timasheff et al., *Cellular Pharmacol.* 1993, 1, S27; (b) Jordan et al., *Nat. Rev. Cancer* 2004, 4, 253; and Gigant et al., *Nature* 2005, 435, 519.] This disruption of a protein-protein interaction by vinblastine is often overlooked in discussions or reviews of such targets as candidate, but challenging, biological targets to address with small molecules perhaps because the target identification preceded the contemporary interest. [(a) Arkin et al., *Nat. Rev. Drug Discovery* 2004, 3, 301; (b) Wells et al., *Nature* 2007, 450, 1001; (c) Yin, et al., *Angew. Chem. Int. Ed.* 2005, 44, 4130; d) Meireles et al., *Med. Chem.* 2011, 11, 248; e) Boger et al., *Chem. Int. Ed.* 2003, 42, 4138.]

In the disclosure that follows, the discovery of compounds modified at C20' that are now a stunning 100-fold more potent than vinblastine and that may initially look unusual in their structure are reported. This increase in potency is shown to correlate directly with enhanced target tubulin binding affinity. Significantly, the remarkable potency of the new compounds ($IC_{50}$'s as low as 50-75 pM) suggest that it is not likely, or even possible, that their cellular functional activity is derived from stoichiometric occupancy of the relatively large number of intracellular tubulin binding sites, but rather implicates effective substoichiometric or catalytic occupancy of candidate binding sites sufficient to disrupt tubulin dynamics and assembly during mitosis.

It is suggested that the newly added linear and rigid C20' urea substituents on vinblastine extend into and create a narrow channel adjacent to the vinblastine binding site, bind across this adjacent region of the protein-protein interaction defined by the tubulin dimer-dimer interface, further disrupt the tubulin c/P head-to-tail dimer-dimer interaction, and extend across the full protein-protein interface contacting solvent on the distal side of the binding site. This further disruption of the target protein-protein interaction by an added structural element to an already complex natural product (added molecular complexity) represents a unique and rational approach to substantially improve the functional properties of such molecules and likely represents a general approach to improving the properties of other natural products that target protein-protein interactions.

BRIEF SUMMARY OF THE INVENTION

The present invention contemplates a 20'-hydroxy-vinca derivative compound (sometimes also referred to herein as a 20'-urea) such as vinblastine, vincristine or vindesine that is substituted at the 20'-position with a urea group whose proximal nitrogen atom that is directly bonded to the 20'-position carbon atom is secondary and whose distal nitrogen is a ring atom of an isoindoline. These proximal and distal nitrogens are illustrated below in the partial structure of a contemplated compound showing atoms near the 20'-position and an urea derivative bonded to the 20'-carbon atom via the proximal urea nitrogen, with the distal urea nitrogen as part of an isoindoline ring structure.

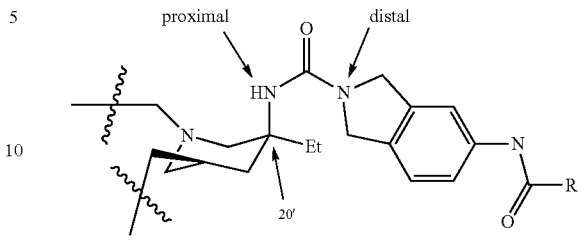

One general observation made in studies of the total syntheses of vinblastine and related natural products is that although removal of individual substituents or key structural features of vinblastine typically results in reductions in biological activity, addition of structural features can substantially improve biological properties. [(a) Leggans et al., Org. Lett. 2012, 14, 1428; (b) Barker et al., J. Am. Chem. Soc. 2012, 134, 13588; and Gotoh et al., ACS Med. Chem. Lett. 2011, 2, 948]. This includes not only demonstration of the impact of the addition of a key indole C10' substituent (10'-fluorovinblasine) [Gotoh et al., ACS Med. Chem. Lett. 2011, 2, 948] but also the discovery of the remarkable impact of select C20' alcohol replacements (C20'-ureas) [(a) Leggans et al., Org. Lett. 2012, 14, 1428; and (b) Barker et al., J. Am. Chem. Soc. 2012, 134, 13588].

Herein, the discovery of compounds in this latter series is reported that exhibit a stunning 100-fold greater potentntcy than vinblastine. Such compounds exhibited $IC_{50}$'s of 50-75 pM against the vinblastine-sensitive tumor cell lines (e.g., HCT116), representing increases of 100-fold relative to vinblastine, and even sub-nanomolar activity against a resistant tumor cell line (HCT116/VM46, $IC_{50}$'s=830-880 pM) insensitive to vinblastine by virtue of the clinically observed Pgp overexpression, representing increases of 700-fold relative to vinblastine.

In one aspect, the invention contemplates a 20'-hydroxy-vinca derivative of structural Formula A,

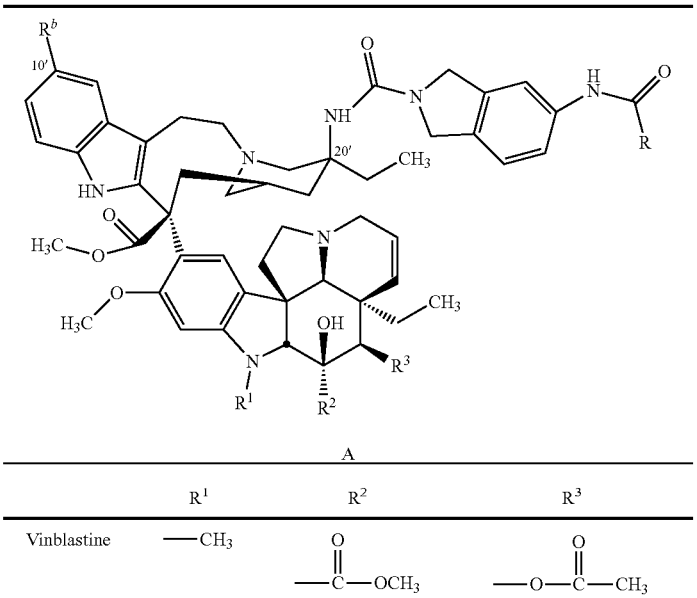

A

| | $R^1$ | $R^2$ | $R^3$ |
|---|---|---|---|
| Vinblastine | —CH$_3$ | —C(O)—OCH$_3$ | —O—C(O)—CH$_3$ |

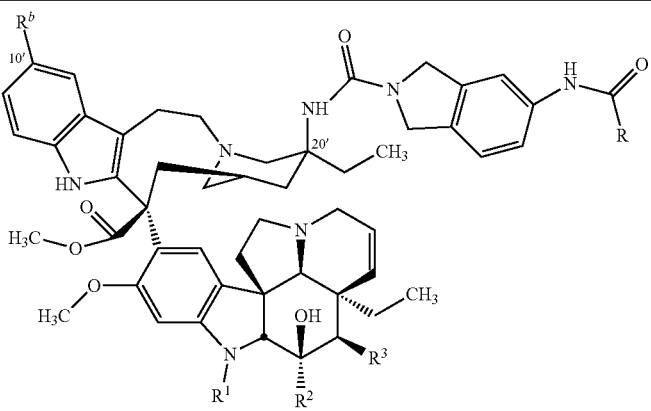

| | R¹ | R² | R³ |
|---|---|---|---|
| Vincristine | —CH=O | —C(=O)—OCH₃ | —O—C(=O)—CH₃ |
| Vindesine | —CH₃ | —C(=O)—NH₂ | —OH |

A wherein R is a substituent of the formula

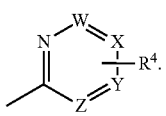

In the 6-membered ring structural formula immediately above, N is nitrogen and one of W, X, Y and Z can also be nitrogen (N). When not nitrogen, W, X, Y and Z are CH or one of W, X, Y, Z is $CR^4$, and $R^4$ is hydrido (H) or an electron donating substituent. $R^b$ in the first structural formula is F or H.

It is preferred that one of W, X, Y and Z is nitrogen. Thus, a preferred 6-membered aromatic R group contains two ring nitrogen atoms. Illustrative R groups have one or more of the structural formulas shown below

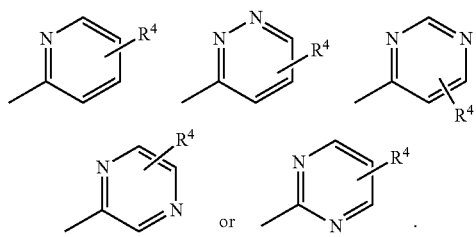

A preferred electron donating substituent group $R^4$ is selected from the group consisting of a $C_1$-$C_4$ hydrocarbyl, amino, mono-$C_1$-$C_4$ hydrocarbylamino, di-$C_1$-$C_4$ hydrocarbylamino and $C_1$-$C_4$ hydrocarbyloxy group. An amino group is a preferred $R^4$ substituent group. It is also presently preferred that $R^b$ be H (hydrido), and that the 20'-hydroxyvinca derivative be a derivative of vinblastine.

A particularly preferred vinblastine derivative (also sometimes referred to herein as a C20'-substituted vinblastine urea) corresponds in structure to structural Formula B in which R is a

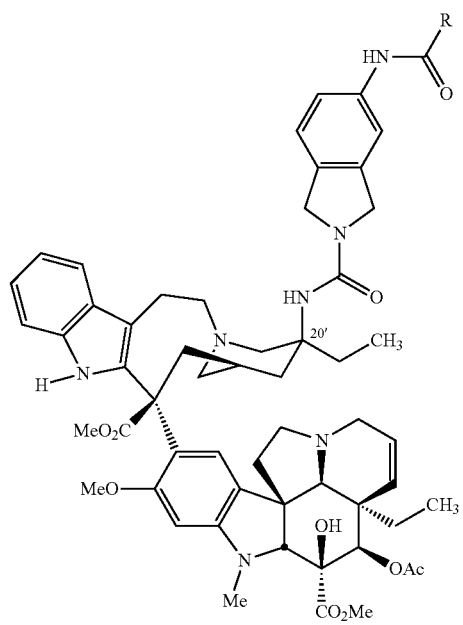

B substituent illustrated by one or more of the five generic structural formulas above, of more specifically having one or more of the specific structural formulas shown below

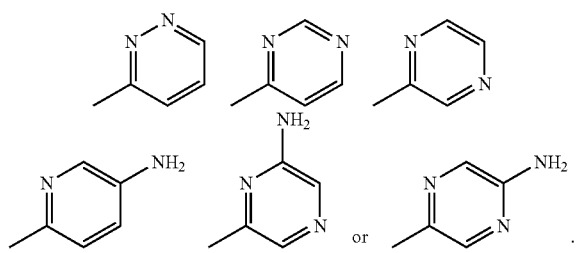

Another contemplated aspect of the invention is a pharmaceutical composition that comprises a cancerous cell proliferation-inhibiting amount of a 20'-hydroxy-vinca derivative compound of structural Formula A, such as a compound of structural Formula B, or a pharmaceutically acceptable salt of a compound of either formula dissolved or dispersed in a physiologically acceptable carrier.

A method of inhibiting the growth of cancerous cells is another aspect of the contemplated invention. In accordance with this aspect, cancerous cells such as leukemia or carcinoma cells are contacted with a cancerous cell proliferation-inhibiting amount of a 20'-hydroxy-vinca derivative compound of structural Formula A, such as a compound of structural Formula B, or a pharmaceutically acceptable salt of a compound either formula. That contacting is typically carried out a plurality of times. That contacting can be carried out in vivo or in vitro.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or hexenyl. Exemplary hydrocarbyl groups contain a chain of 1 to about 6 carbon atoms, and preferably 1 to about 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, hexenyl, hexadienyl and the like. Examples of alkynyl radicals include ethynyl, 2-propynyl, 3-propynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, tert-butoxy, cyclohexenyloxy groups and the like.

As a skilled worker will understand, a substituent that cannot exist such as a $C_1$ alkenyl group is not intended to be encompassed by the word "hydrocarbyl", although such substituents with two or more carbon atoms are intended.

The term "cyclohydrocarbyl" or "carbocyclic", alone or in combination, means a hydrocarbyl radical that contains 3 to about 8 carbon atoms, preferably about 3 to about 6 carbon atoms, and is cyclic. Examples of such cyclohydrocarbyl radicals include cyclopropyl, cyclobutyl, cyclopentenyl, cyclohexyl, cycloheptynyl and the like.

DETAILED DESCRIPTION OF THE INVENTION

Approaches to improving the properties of natural products typically involve efforts to simplify or edit their structures through semi-synthetic modifications, diverted total synthesis [Wilson et al., *J. Org. Chem.* 2006, 71, 8329], or late-stage functionalization [Reviews: (a) Szpilman et al., *Angew. Chem. Int. Ed.* 2010, 49, 9592; and (b) Hong, *J. Chem. Eur. J.* 2014, 20, 10204]. Such efforts often strive to identify the imbedded pharmacophore, remove or introduce key functional groups to enhance target binding affinity, improve physiochemical properties, incorporate stabilizing modifications, or introduce conformational constraints. Rarely, if ever, does one consider adding molecular complexity to the core structure as has been done here.

In part, that reluctance can be attributed to the perceived added challenge that might accompany the more elaborate compound synthesis. The synthetically-derived ultra-potent derivatives are exemplified by the 20'-substituted vinblastines that are described hereinafter. These ultra-potent 20'-hydroxy-vinca derivatives are about 100-fold more active than the natural product, represent 20'-hydroxy-vinca analogues that are typically accessible by chemical synthesis in three steps from commercially available and relatively inexpensive materials (catharanthine, $16/g; and vindoline, $36/g) based on methodology introduced by the inventor and co-workers, and are presently inaccessible by classical natural product derivatization, late-stage functionalization, or biosynthetic methods.

The newly discovered ultra-potent 20'-hydroxy-vinca derivative compounds described herein, which also display much higher tubulin binding affinities, likely further disrupt the target tubulin head-to-tail c/P dimer-dimer interaction by virtue of the strategic placement of the added rigid and extended C20' urea along the adjacent continuing protein-protein interface. In instances when the therapeutic properties of a natural product are directly related to its emergence in Nature and has undergone evolutionary optimization by natural selection as may be the case with vinblastine, it may not be easily subjected to optimization by structural simplifications. In such cases, added molecular complexity can be used to enhance target binding and functional biological activity, and approaches such as the one illustrated herein targeting a protein-protein interaction can represent an appealing and general approach to achieving such objectives.

Thus, in one aspect, the present invention contemplates a 20'-hydroxy-vinca derivative compound of structural Formula A,

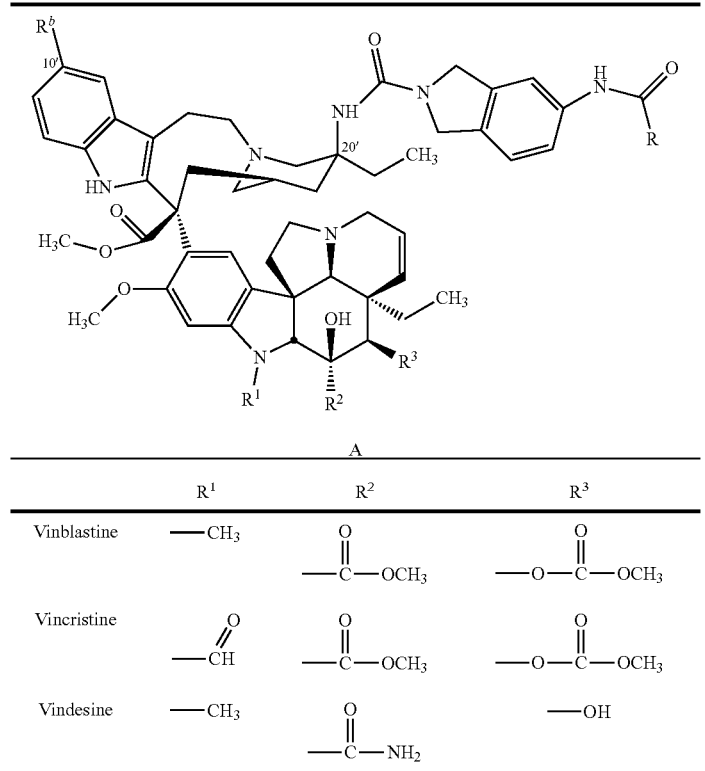

| | $R^1$ | $R^2$ | $R^3$ |
|---|---|---|---|
| Vinblastine | —CH$_3$ | —C(O)—OCH$_3$ | —O—C(O)—OCH$_3$ |
| Vincristine | —CH(O) | —C(O)—OCH$_3$ | —O—C(O)—OCH$_3$ |
| Vindesine | —CH$_3$ | —C(O)—NH$_2$ | —OH |

A wherein R is a substituent of the formula

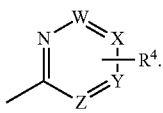

In the structural formula of the R substituent 6-membered aromatic ring structure immediately above, N is nitrogen and one of W, X, Y and Z can also be nitrogen (N). When not nitrogen, W, X, Y and Z are CH or one of W, X, Y, Z is CR$^4$, where R$^4$ is hydrido or an electron donating substituent. R$^b$ in the first structural formula is F or H. It is preferred that one of W, X, Y and Z be nitrogen so that there are two ring nitrogens in a preferred 6-membered ring R substituent.

Whether there are two ring nitrogens in the 6-membered ring R substituent or only one ring nitrogen, another of W, X, Y, Z is CR$^4$, where R$^4$ is hydrido (H) or an electron donating substituent. Illustrative R$^4$ electron donating substituent groups are selected from the group consisting of one or more of a C$_1$-C$_4$ hydrocarbyl, amino, mono-C$_1$-C$_4$ hydrocarbylamino, di-C$_1$-C$_4$ hydrocarbylamino and C$_1$-C$_4$ hydrocarbyloxy group.

An electron donating substituent group typically has a Hammett sigma value that is less than zero, the arbitrary value set for hydrogen, and is thus a negative number. Hammett sigma values are well known in organic chemistry and those values for para-position substituents reflect both electron donation or withdrawal via an inductive effect, but also are understood to reflect a resonance effect. It is noted that a para-position sigma value is utilized herein for defining an electron donating substituent group regardless of the actual position of the substituent on the aromatic ring. For Hammett sigma values see, for example, U.S. Pat. Nos. 7,473,477, 5,811,521, 4,746,651, and 4,548,905. A list of Hammett sigma values can be found in J. Hine, *Physical Organic Chemistry*, 2$^{nd}$ ed., McGraw-Hill Book Co., Inc., New York page 87 (1962) and at the web site: wiredchemist.com/chemistry/data/harmett_sigma_constants.

Examining the one or two ring nitrogen-containing substituent groups, R, more closely, it is first noted that one nitrogen is at the 2-position of the 6-membered aromatic ring. A second nitrogen, when present, can be at any other position in the ring except for the 1-position. The R group ring is bonded at its 1-position to the carbonyl group of the amido function that links substituent R to the isoindoline. The nitrogen atom of the isoindoline group is the distal nitrogen of the urea group bonded at the 20' position of the vinca compound. A contemplated R group substituent has a structural formula of one or more of those shown below

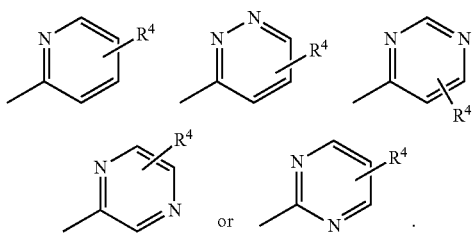

Structural formulas for particularly preferred R groups are shown below.

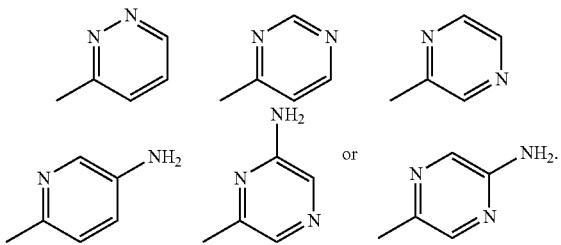

As is seen from the above structural formulas, amino (—NH$_2$) is a particularly preferred R$^4$ substituent. The Hammett sigma value for a para-position amino group according to the Hine text, above, is −0.66.

A contemplated compound of structural Formula A above can have a fluorine atom (F) at the 10' position or a hydrido group at that position (R$^b$). The preparation of 10'-F-substituted 20'-hydroxy-vinca derivative compounds is taught in the inventor's U.S. Pat. No. 8,940,754, whose teachings are incorporated by reference. Broadly, that patent teaches reaction of 10-fluorocatharanthine (a 10-fluorinated derivative of Compound 2 that was shown previously) is reacted with vindoline (3) to begin the synthesis of an appropriate vinblastine derivative.

Pharmaceutical Composition and Methods

A contemplated 20'-hydroxy-vinca derivative compound can also be used in the manufacture of a medicament (pharmaceutical composition) that is useful at least for inhibiting the proliferation (growth) of hematologic cancer cells such as leukemia or lymphoma cells, as well as cells of carcinomas, sarcomas, melanomas, neuromas and the like. A contemplated compound, medicament or pharmaceutical composition containing the same inhibits that growth by contacting those cancerous cells in vitro, or in vivo as in a subject in need thereof, as is a parent vinca alkaloid compound. When so used, pharmaceutically acceptable salts, buffers and the like are present that collectively are referred to as pharmaceutically acceptable diluents as compared to those that can be present in a composition that is not intended for pharmaceutical use, as in an in vitro assay.

A compound of the invention can be provided for use by itself, or as a pharmaceutically acceptable salt. The contemplated compounds are amines. Parental vinblastine has reported pKa values of 5.4 and 7.4, whereas vincristine has reported pKa values of 6.04 and 7.67. [*The Merck Index*, 13$^{th}$ ed. Merck & Co., Whitehouse Station, N J, 2001, pages 1778-1779.] Both compounds are sold commercially as their sulfate salts. Vindesine is reported to have pka values of 6.04 and 7.67 [*The Merck Index*, 12$^{th}$ ed., Merck and Co., Whitehouse Station, N J, 1996, page 1704]. Vindesine is also commercially available as the sulfate salt.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As is seen from the data that follow, a contemplated compound is active in in vitro assay studies at picomolar to nanomolar amounts. When used in an assay such as an in vitro assay, a contemplated compound is present in the composition in an amount that is sufficient to provide a concentration of about 0.05 nM to about 100 nM, preferably about 1 nM to about 50 nM to a contact cells to be assayed.

A contemplated pharmaceutical composition contains a cancerous cell proliferation-inhibiting amount of a contemplated 20'-hydroxy-vinca derivative compound or a pharmaceutically acceptable salt thereof dissolved or dispersed in a physiologically (pharmaceutically) acceptable carrier. That amount is typically about the same amount to a little less than the amount of a parental vinca alkaloid used to treat the same cancer. Such a composition can be administered to mammalian cells in vitro as in a cell culture to contact those cells, or the cells can be contacted in vivo as in a living, host mammal in need.

More usually, anti-neoplastic drugs such as a 20'-hydroxy-vinca derivative compound contemplated here are administered parenterally in vivo in a weight amount per square meter of the recipient's body surface area (bsa). For adults, this amount is typically about 1 to about 20 mg/m$^2$ bsa, and about one-half those amounts for children, with an amount being chosen so that the maximal amount does not cause leukopenia. Children weighing about 10 kg or less are typically dosed at about 0.05 mg/kg.

For example, vinblastine sulfate is typically administered to adults at 3.7 mg/m$^2$ bsa for the first dose, 5.5 mg/m$^2$ bsa for the second weekly dose, 7.4 mg/m$^2$ bsa for the third weekly dose, 9.25 mg/m$^2$ bsa for the fourth weekly dose and 11.1 mg/m$^2$ bsa for the fifth weekly dose. Dosages typically do not exceed 18.5 mg/m$^2$ bsa, and should not be increased if the white-cell count falls to approximately 3000 cells/mm$^3$. Usual dosages for adults are about 5.5 to 7.4 mg/m$^2$ bsa. Dosages of a contemplated 20'-hydroxy-vinca derivative compound or its pharmaceutically acceptable salt typically do not exceed those of the parent compound and are typically less by about 10- to about 100-fold.

A contemplated composition is typically administered in vivo to a subject in need thereof a plurality of times within one month, such as weekly, and can be administered over a period of several months to several years. More usually, a contemplated composition is administered a plurality of times over a course of treatment.

In usual practice, a contemplated 20'-hydroxy-vinca derivative compound is administered to treat the same disease state in the same or lessened amount and at the same intervals as is a parental, 20'-hydroxy-vinca alkaloid. A contemplated 20'-hydroxy-vinca derivative compound can be utilized as a first course of treatment, and is preferably administered if there is relapse after a first or later course of treatment, particularly where multiple drug resistance is shown or suspected (indicated).

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous (which is most preferred), intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Solid dosage forms for oral administration can include capsules, tablets, pills, powders, and granules. The amount of a contemplated compound in a solid dosage form is as discussed previously, an amount sufficient to provide a concentration of about 0.05 nM to about 100 nM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a 20'-hydroxy-vinca derivative compound active component or sterile solution of the active component in solvents comprising water, ethanol, or propylene glycol are examples of liquid compositions suitable for parenteral administration. In some aspects, a contemplated 20'-hydroxy-vinca derivative compound is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

A mammal in need of treatment (a subject) and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain the water, sodium or potassium chloride, and one or more buffer salts such as and acetate and phosphate salts, HEPES [N-(2-hydroxyethyl) piperazine-N'-(2-ethanesulfonic acid)] or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated 20'-hydroxy-vinca derivative compound is administered with one or more other anti-neoplastic compounds. Such joint therapy is well known in the art, with other drugs such as cisplatin, 5-fluorouracil and the like being co-administered. That co-administration is usually physically separate administrations of each compound that are timed so that the two or more active agents can act in concert.

Results and Discussion

Two C20'-substituted vinblastine ureas 8 and 9 were prepared in initial studies that served as starting points. The first of these is the pyrrolidine urea 8, which exhibited improved cell growth inhibition relative to vinblastine. Thus, a series of functionalized or substituted pyrrolidines were incorporated into the C20'-urea through reaction of 20'-aminovinblastine (6), derived from reduction of the hydroazidation product 5, with either p-nitrophenyl chloroformate (1.5 equiv 4-$NO_2$PhOCOCl, 10 equiv $Et_3N$, THF, 23° C., 4 hours) or triphosgene (0.4 equiv, 2.4 equiv i-$Pr_2$NEt, $CH_2Cl_2$, 0° C., 15 minutes) followed by treatment with a secondary amine ($R_2$NH) to afford the product C20'-ureas in good yields (See, Scheme 2, below). The latter procedure that uses triphosgene represents an improvement in the originally reported conditions [Leggans et al., *J. Med. Chem.* 2013, 56, 628], avoiding the purification challenges of removing residual p-nitrophenol from the reaction products. Both sets of conditions create the same intermediate C20'-isocyanate that in turn reacts with the added secondary amine to provide a product urea.

Scheme 2

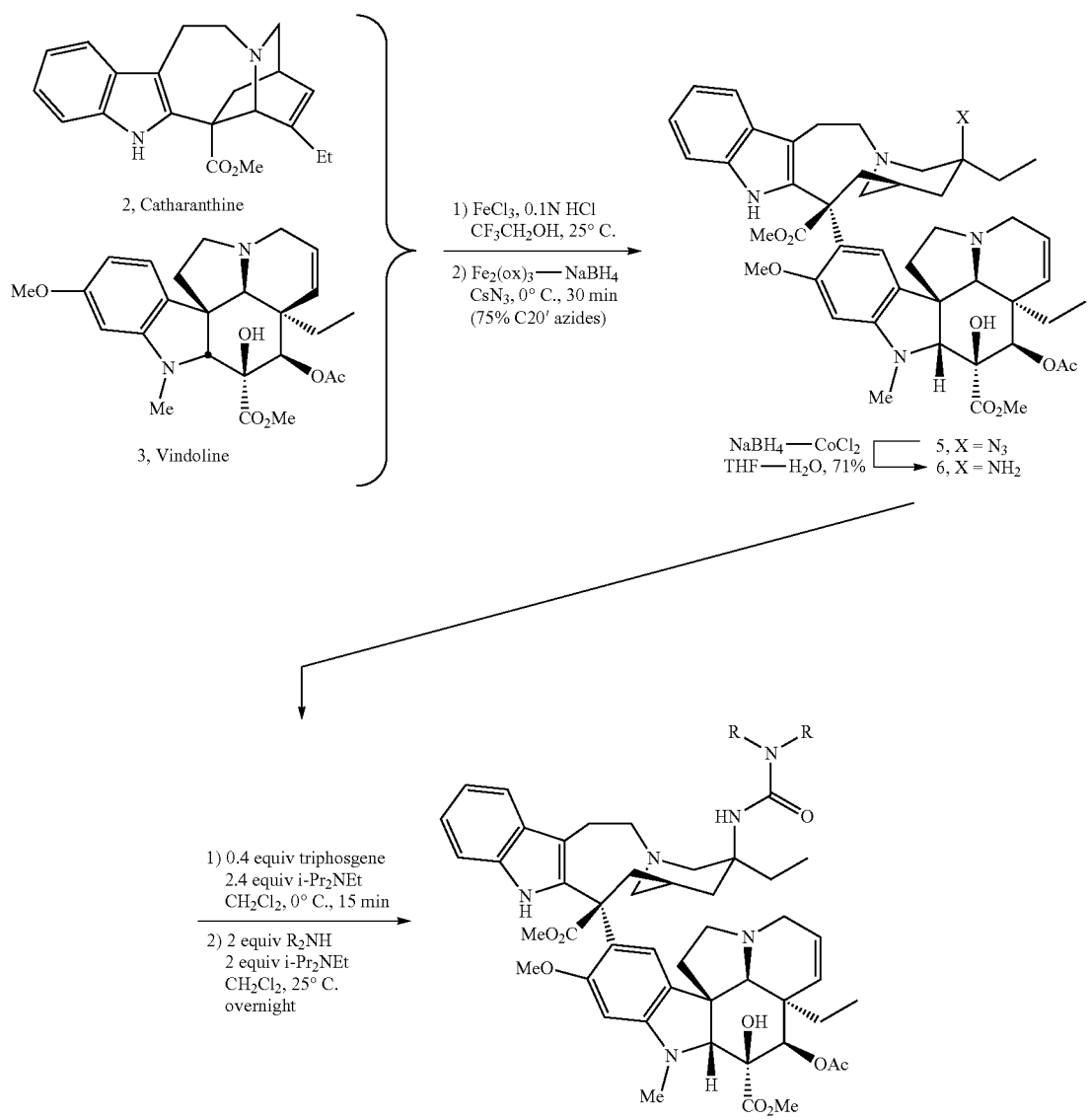

For the comparisons reported herein, the compounds were examined for cell growth inhibition against L1210 (mouse leukemia), HCT116 (human colon cancer), and HCT116/VM46 (resistant human colon cancer) tumor cell lines, the latter of which exhibits resistance (100-fold) to vinblastine through the clinically relevant overexpression of P-glycoprotein (Pgp).

In initial studies [Leggans et al., *J. Med. Chem.* 2013, 56, 628], it was established that the electron rich nature of the urea was responsible in part for their enhanced activity relative to their corresponding carbamate or amide counterparts. As a consequence, the pyrrolidine urea 8 was systematically probed to establish whether β-substituents on the pyrrolidine (10-21) or systematic changes in its structure (22-27) might impact its binding to tubulin and cell growth inhibition properties much like their impact on the pyrrolidine basicity itself. Nearly all such substituted pyrrolidine ureas were less potent than the pyrrolidine urea 8 itself, most showed little preference for the substituent stereochemistry (R vs S), and there did not appear to be a direct correlation of the substituent electronic properties with its impact on the cell growth inhibition activity (Table 1, below). The exceptions to these generalizations are the behavior of 14, bearing the (R)-3-methoxypyrrolidine, and the two isomers of the 3-fluoropyrrolidine urea (17 and 18).

As interesting as these latter observations are, these compounds only approach (14) or slightly surpass (17 and 18) the activity of 8, which bears no substituent. As a consequence, and rather than ascribing productive roles to the substituents, it appears that most detract from the properties of the parent compound 8 and a few (14, 17 and 18) constitute benign substitutions.

TABLE 1

| cell line | | | | IC$_{50}$, nM | | | |
|---|---|---|---|---|---|---|---|
| X = | (pyrrolidine) | (R)-3-NMe$_2$-pyrrolidine | (S)-3-NMe$_2$-pyrrolidine | (R)-3-OH-pyrrolidine | (S)-3-OH-pyrrolidine | (R)-3-OMe-pyrrolidine | (S)-3-OMe-pyrrolidine |
| | 8[a] | 10 | 11 | 12 | 13 | 14 | 15 |
| L1210 | 0.70 | 20 | 14 | 6.8 | 40 | 0.71 | 3.5 |
| HCT116 | 0.72 | 20 | 6.2 | 5.8 | 8.6 | 0.71 | 2.9 |
| HCT116/VM46 | 50 | 500 | 390 | 210 | 650 | 25 | 40 |

| X = | 3-OMe-pyrrolidine | (R)-3-F-pyrrolidine | (S)-3-F-pyrrolidine | 3-Br-pyrrolidine | (R)-3-CN-pyrrolidine | (S)-3-CN-pyrrolidine | 3-pyrroline |
|---|---|---|---|---|---|---|---|
| | 16 | 17 | 18 | 19 | 20 | 21 | 22 |
| L1210 | 3.3 | 0.62 | 0.60 | 3.1 | 3.7 | 5.1 | 0.53 |
| HCT116 | 1.0 | 0.64 | 0.61 | 0.90 | 1.5 | 1.8 | 0.50 |
| HCT116/VM46 | 25 | 7.2 | 20 | 25 | 60 | 60 | 5.7 |

[a]Previously reported in Barker et al., *ACS Med. Chem. Lett.* 2013, 4, 985.

More significant was the impact of adding unsaturation (compound 22). Whereas incremental decreases in cell growth activity were seen with increasing ring size of the urea terminal cyclic amine (8 vs 23-25, 5<6 or 7<8) or with the incorporation of the pyrrolidine in an azabicyclo[2,2,1] heptane (26), the introduction of 7-unsaturation in either the form of a 3,4-double bond (22) or a 3,4-fused phenyl ring (27 and 9) provided compounds that enhanced cell growth inhibition and further reduced the differential in activity between the sensitive and resistant HCT116 cell lines (Table 2, below).

TABLE 2

[Structure of vinblastine analog with X substituent at 20' position]

| cell line | | | IC$_{50}$, nM | | |
|---|---|---|---|---|---|
| X = | pyrrolidine | 2,5-dihydropyrrole | piperidine | azepane | azocane |
|  | 8[a] | 22 | 23[a] | 24 | 25 |
| L1210 | 0.70 | 0.53 | 5.5 | 4.3 | 60 |
| HCT116 | 0.72 | 0.50 | 3.9 | 3.1 | 35 |
| HCT116/VM46 | 50 | 5.7 | 50 | 35 | 330 |

| X = | bicyclic pyrrolidine | benzo-fused azocane | isoindoline | pyrrolo-pyridine | pyrrolo-pyridine |
|---|---|---|---|---|---|
|  | 26 | 27 | 9[a] | 28 | 29 |
| L1210 | 40 | 0.59 | 0.51 | 0.40 | 0.47 |
| HCT116 | 20 | 0.69 | 0.60 | 0.60 | 0.45 |
| HCT116/VM46 | 250 | 6.2 | 7.5 | 10 | 9.5 |

[a]Previously reported in Barker et al., *ACS Med. Chem. Lett.* 2013, 4, 985.

It is possible that this improved activity is derived in part from alterations in the basicity of the pyrrolidine, reductions in destabilizing steric interactions surrounding the pyrrolidine 3,4 position, or through acquisition of additional stabilizing interactions with tubulin and it is most likely the result of a different combination of such features for 22/9 versus 27.

Finally, replacement of the fused benzene in isoindoline 9 with fused pyridines (28 and 29) was not only permitted, but the change provided a further small enhancement in the cell growth inhibition potency. It is especially notable that 22, 9, 28 and 29 all exhibit cell growth inhibition activity in the vinblastine-sensitive tumor cell lines with IC$_{50}$'s of 400-600 pM and that their activity against the vinblastine-resistant tumor cell line (HCT116/VM46) now matches the activity that vinblastine displays against the matched sensitive HCT116 cell line (IC$_{50}$=6.8 nM).

Of these, further modifications of the isoindoline urea 9 were targeted for systematic examination, recognizing the potential for further disruption of the tubulin dimer-dimer interface (Table 3, below). Substitution of the isoindoline was well tolerated and the series displayed a trend where electron-donating substituents (30, 35-39) proved slightly more potent than compounds bearing electron-withdrawing substituents (31-34). Within the former series, further alkylation (37-39) or acylation (40-53) of the aniline 36 was well tolerated. Simple acetylation to provide the acetamide 40 provided a derivative with IC$_{50}$'s of 470-500 pM in the vinblastine sensitive tumor cell lines and N-benzoylation maintained this activity with 50 displaying IC$_{50}$'s of 500-600 pM.

TABLE 3

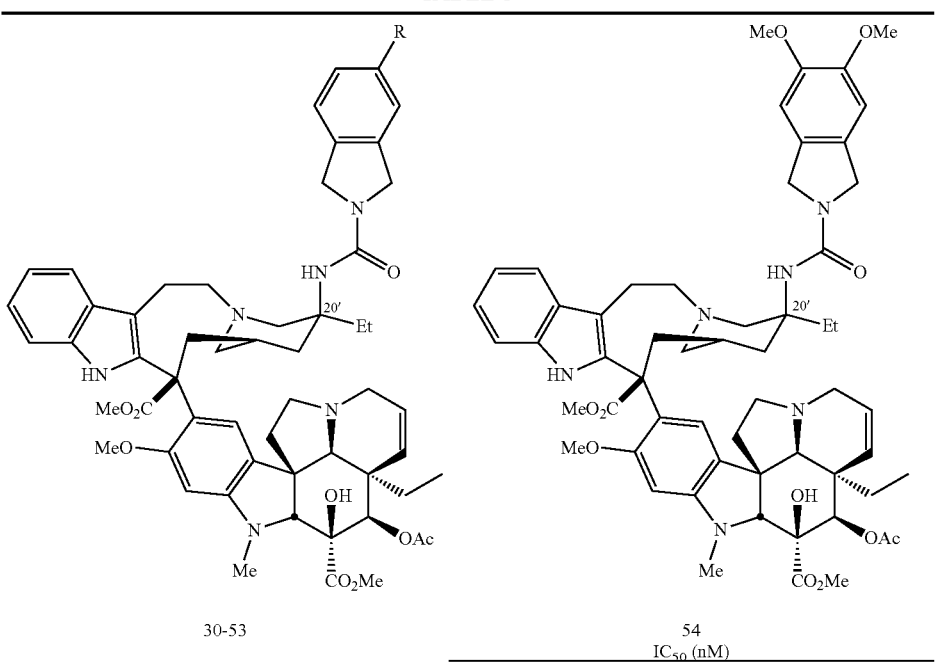

| Compound | L1210 | HCT116 | HCT116/VM46 |
|---|---|---|---|
| 9, R = H[a] | 0.51 | 0.60 | 7.5 |
| 30, R = Me | 0.41 | 0.44 | 5.9 |
| 31, R = F | 0.63 | 0.52 | 5.2 |
| 32, R = Cl | 0.50 | 0.55 | 5.7 |
| 33, R = Br | 0.62 | 0.56 | 6.4 |
| 34, R = CF$_3$ | 0.59 | 0.67 | 6.2 |
| 35, R = OMe[a] | 0.48 | 0.54 | 8.6 |
| 36, R = NH$_2$ | 0.47 | 0.42 | 6.8 |
| 37, R = NHMe | 0.45 | 0.43 | 4.6 |
| 38, R = NMe$_2$ | 0.50 | 0.62 | 3.9 |
| 39, R = NHPr | 0.40 | 0.31 | 4.6 |
| 40, R = NHCOMe | 0.47 | 0.50 | 9.4 |
| 41, R = NHCOPr | 0.46 | 0.54 | 7.7 |
| 42, R = NHCOc—Pr | 0.50 | 0.56 | 16 |
| 43, R = NHCOi—Bu | 0.39 | 0.49 | 6.4 |
| 44, R = NHCOCMe$_3$ | 0.39 | 0.47 | 5.3 |
| 45, R = NHCOn-Hex | 0.44 | 0.62 | 13 |
| 46, R = NHCOCH=CH$_2$ | 0.38 | 0.30 | 7.1 |
| 47, R = NHCOCH=CHMe | 0.42 | 0.38 | 5.9 |
| 48, R = NHCOCH=CMe$_2$ | 0.43 | 0.47 | 7.4 |
| 49, R = NHCOCH=CHPh | 0.50 | 0.70 | 33 |
| 50, R = NHCOPh | 0.54 | 0.62 | 13 |
| 51, R = NHCOPh-4-Ph | 5.9 | 6.3 | 75 |
| 52, R = NHCOPh-4-OCF$_3$ | 4.3 | 5.3 | 75 |
| 53, R = NHCOPh-4-/Pr | 2.9 | 4.2 | 60 |
| 54 | 0.42 | 0.45 | 5.2 |

[a]Previously reported in Barker et al., *ACS Med. Chem. Lett.* 2013, 4, 985.

The site proved remarkably tolerant of steric bulk with even the pivoloyl amide 44 displaying potent activity and it proved capable of accommodating extended rigid acyl groups (e.g., 49). Only bulky or rigid extended substitution on the para position of an N-benzoyl group (51-53) proved to diminish the activity of the now remarkably potent series. Even appending a 4-biphenyl acyl group to the isoindoline aniline provided a compound (51) that, although less potent that either 40 or 50, was still slightly more potent than vinblastine despite being buried in a region of the tubulin binding site previously thought to be sensitive to steric interactions. Finally, disubstitution of the isoindoline was found to be both well tolerated and, in the case examined (54), provided a compound equipotent with 35 and slightly more potent than the parent isoindoline 9.

Even more impressive levels of activity and further improvements in the cell growth inhibition were observed when the benzoyl amide of 50 was replaced with heteroaromatic amides (Table 4, below). A clear trend in activity emerged in the series examined (55-67) to confidently indicate the functionality responsible for and needed to provide the additional stunning enhancements in activity. Although all such compounds were exceptionally potent, those with six-membered heteroaromatic groups with nitrogen in the 2-position relative to the acyl carbonyl routinely displayed the more potent activity (e.g., 55 vs 56; 58, 60 and 61 vs 59), and those with two such nitrogens where at least one of which is in the 2-position displayed stunning potency (58, 60, and 61).

TABLE 4
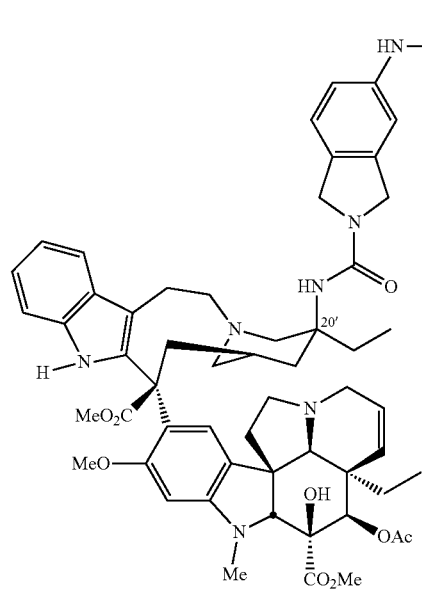
| cell line | | | | IC$_{50}$, nM | | | |
|---|---|---|---|---|---|---|---|
| R = | 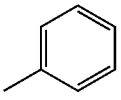 | 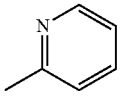 | 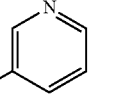 | 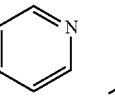 | 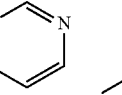 | 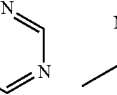 | 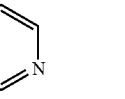 |
|  | 50 | 55 | 56 | 57 | 58 | 59 | 60 |
| L1210 | 0.54 | 0.37 | 0.48 | 0.27 | 0.062 | 0.51 | 0.059 |
| HCT116 | 0.62 | 0.49 | 0.33 | 0.28 | 0.074 | 0.60 | 0.075 |
| HCT116/VM46 | 13 | 3.6 | 6.6 | 10.4 | 0.88 | 8.8 | 0.83 |
|  | 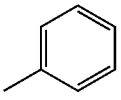 | 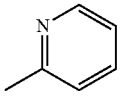 | 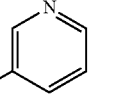 | 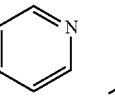 | 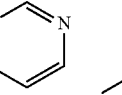 | 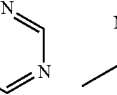 | 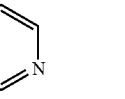 |
|  | 61 | 62 | 63 | 64 | 65 | 66 | 67 |
| L1210 | 0.059 | 0.69 | 0.25 | 0.38 | 0.29 | 0.23 | 0.43 |
| HCT116 | 0.067 | 0.64 | 0.10 | 0.17 | 0.19 | 0.22 | 0.51 |
| HCT116/VM46 | 0.87 | 50 | 5 | 5 | 5 | 4 | 7.6 |
It is likely this enhanced potency reflects an internal hydrogen bond between the heteroaromatic nitrogen at the 2-position and the adjacent amide NH that is observed in the $^1$H NMR of the compounds. This is illustrated in the structural formula shown below.

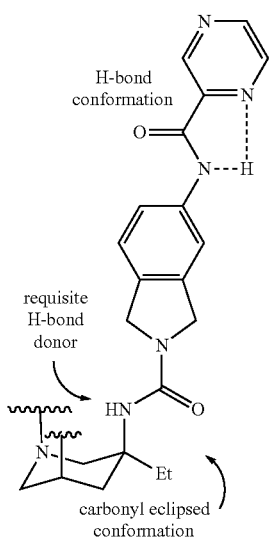

Complementary to this conformational constraint is the preferential adoption of the carbonyl eclipsed conformation of the C20'-urea that fixes the preferred orientation of the C20'-urea.

Compounds 58, 60 and 61 exhibited IC$_{50}$'s of 50-75 pM against the vinblastine sensitive tumor cell lines (L1210 and HCT116), representing increases of 100-fold relative to vinblastine, and sub-nanomolar activity against the vinblastine-resistant tumor cell line (HCT116/VM46, IC$_{50}$'s=830-880 pM), representing increases of 700-fold relative to vinblastine. They are also 10-fold more potent than the C20' urea 9 that lacks a substituent.

Because of their extraordinary potency, two heterocyclic amides (55 and 60) were further functionalized with an aryl amine, which would permit covalent conjugation with targeting modalities that require this ultra-potent activity (e.g., antibodies, folate) for selective delivery to tumors (Table 5). In each case, the aniline derivative maintained the activity of the parent analogue (69 and 70 vs 60) or even further improved its potency (68 vs 55). Clearly, varied opportunities with subtle impacts on activity are available for both the site and appropriate functionalization of such derivatives for the preparation of tumor targeting conjugates for which the released free drug payload remains extraordinarily potent.

With compounds displaying remarkable functional cellular potency, it was sought to determine if the observed improvements in activity correlated with enhanced tubulin binding affinity. The most common method for assessing tubulin binding entails inhibition of tubulin polymerization upon exposure to the candidate compounds. However, and as noted by others, this method is insensitive, rarely correlates with the functional activity, and lacks the resolution to discriminate among a series of compounds. More accurate are methods that measure competitive binding at the vinblastine tubulin binding site and these typically involve measurement of the competitive displacement of radiolabeled vinblastine or fluorescently labeled vinblastine probes.

The competitive displacement of $^3$H-vinblastine has previously been used to assess the tubulin binding of selected members of the vinblastine C20'-ureas. [Leggans et al., *J. Med. Chem.* 2013, 56, 628; and Barker et al., *ACS Med. Chem. Lett.* 2013, 4, 985.] This assay involves filtering co-incubation solutions through DE-81 filter disks, which sequester tubulin and its bound ligands from solution. [(a) Owellen et al., *Biochem. Pharmacol.* 1977, 26, 1213; and (b) Bhattacharyya et al., *Proc. Natl. Acad. Sci. U.S.A.* 1976, 73, 2375.] However, the assay is not ideal due to both the cost associated with using $^3$H-vinblastine and the technical challenges of quantitatively reproducing the assay. This is further complicated by the fact that the manufacture of DE-81 filter paper has now been discontinued.

As a consequence, the commercially available BODIPY-vinblastine fluorescent probe was used to assess tubulin binding and develop its use in a direct competitive binding assay.[15] [(a) Jiang et al., *Cancer Res.* 1998, 58, 5389; (b) Zhang et al., *PloS one* 2009, 4, e4881; (c) Rai et al., *PloS one* 2012, 7, e44311 and (d) Rashid et al., *Biochemistry* 2015, 54, 2149.] BODIPY-vinblastine exhibits a significant increase in fluorescence intensity (FI) upon binding to tubulin and therefore allows simple fluorescent measurements of co-incubation solutions to establish the percent displacement of probe by a competitive binding site ligand.

Tubulin was incubated with BODIPY-vinblastine and a representative range of competitive ligands including vinblastine, 10'-fluorovinblastine (71, a previously reported vinblastine analogue with 10-fold improved functional activity [Gotoh et al., *ACS Med. Chem. Lett.* 2011, 2, 948]), the potent compound 28, and three ultra-potent C20'-urea analogues (58, 60 and 61) reported here. At the concentration tested, vinblastine displaced 31% of the BODIPY-vinblastine bound to tubulin (Table 5). 10'-Fluorovinblastine and 28, which are roughly 10-fold more potent than vinblastine, displayed a higher tubulin affinity, displacing 48-49% of the BODIPY-vinblastine. Remarkably, the three ultra-potent vinblastines (58, 60 and 61), each 100-fold more potent than vinblastine, displaced 100% of the BODIPY-vinblastine, indicating that these ultra-potent C20' ureas possess a much stronger binding affinity for tubulin than vinblastine, 10'-fluorovinblastine and 28.

TABLE 5

| R = | 68 | 69 | 70 |
|---|---|---|---|
| cell line | IC$_{50}$, nM | | |
| L1210 | 0.08 | 0.065 | 0.062 |
| HCT116 | 0.20 | 0.075 | 0.068 |
| HCT116/VM46 | 2.6 | 4.1 | 0.94 |

TABLE 5

| compd | % displacement | IC$_{50}$ (nM, HCT116) |
| --- | --- | --- |
| 1 | 31 ± 9% | 6.8 |
| 71 | 48 ± 7% | 0.8 |
| 28 | 49 ± 15% | 0.6 |
| 58 | 105 ± 5% | 0.07 |
| 60 | 104 ± 12% | 0.07 |
| 61 | 101 ± 4% | 0.07 |

In carrying out this study, tubulin (0.1 mg/mL, 0.91 μM) was incubated with BODIPY-vinblastine (BODIPY-VBL, 1.8 μM) and a vinblastine analogue (18 μM) at 37° C. in PEM buffer containing 850 μM GTP. The BODIPY-VBL fluorescence intensity (FI) (ex: 480 nm, em: 514 nm) of 100 μL aliquots from each incubation were measured in a fluorescence micro-plate reader at 37° C. Control studies were performed with BODIPY-VBL (control 1) in the absence of a competitive ligand (maximum FI enhancement due to tubulin binding) and (control 2) in the absence of tubulin (no FI enhancement due to tubulin binding). % BODIPY-VBL displacement was calculated by the formula (control 2 FI–experiment FI)/(control 2 FI–control 1 FI)× 100. Reported values are the average 4 measurements±the standard deviation.

Although it is not possible to rule out the impact of other features or even introduction of an unrecognized second mechanism of action, this direct correlation of functional cell growth inhibition activity with target tubulin binding affinity and the relative magnitude of the effects suggest that the properties of the potent and ultra-potent C20' ureas are derived predominately, if not exclusively, from on target effects on tubulin.

It is noted that Jordan et al., *Cancer Res* 1985, 45, 2747, studied vinepidine, a synthetic derivative of vincristine, vinblastine, vincristine and vindesine as inhibitors of tubulin addition to the ends of bovine brain microtubules. They found that the four compounds had generally similar potency in inhibiting microtubule assembly, but that vinepidine and vincristine were the most potent followed by vindesine and vinblastine. However, they also found that vinblastine and vindesine were generally more potent than vincristine and vindesine in in vitro cell proliferation studies. Thus, the correlation shown here does not hold in all study systems.

In contrast to initial expectations based on the steric constraints of the tubulin binding site surrounding the vinblastine C20' center depicted in the X-ray co-crystal structure of a tubulin bound complex [Gigant et al., *Nature* 2005, 435, 519], large C20' urea derivatives such as those detailed herein are accommodated, with some exhibiting ultra-potent functional activity in cell-based proliferation assays and remarkable tubulin binding affinity. This raised several key questions that include whether there is room for such substituents in the purported vinblastine binding site.

The binding site for vinblastine is created by and lies at the head-to-tail tubulin α/β dimer-dimer interface. Vinblastine is essentially completely buried in the protein binding site, adopting a T-shaped bound conformation with C3/C4 (bottom of T) lying at the solvent interface and the C20' site (top corner of T) extending deepest into the binding pocket lying at one corner. This binding of vinblastine destabilizes the protein-protein interaction integral to microtubulin assembly.

Inspection of the vinblastine-tubulin X-ray structure reveals that the C20' alcohol extends toward a narrow channel that leads from the buried C20' site to the opposite face of the protein, representing the continuation of the protein-protein interaction defined by the tubulin dimer-dimer interface. Even without adjusting the proteins found in the vinblastine bound X-ray structure, the modeled C20' isoindoline group of 9 extends behind a key peptide loop in β-tubulin that constitutes the top of the vinblastine binding site into this narrow channel, continuing along the tubulin protein-protein interface and presumably is responsible for further disruption of the dimer tubulin-tubulin interaction. A peptide loop on the β-tubulin protein covers the top side of the vinblastine velbanamine subunit including C20' creating a deep and largely hydrophobic pocket for ligand binding. Without adjusting the protein found in the vinblastine bound X-ray structure, the isoindoline group of modeled 9 extends behind the loop peptide into a channel continuing along the tubulin protein-protein interface. Aryl amide substituents on the isoindoline such as those found in 50, 55-67 continue to extend along the tubulin dimer protein-protein interface.

It is likely that the rigid linear C20' urea of the ultra-potent vinblastines described herein extends into and expands this narrow channel, even further disrupts the tubulin α/β head-to-tail dimer-dimer interface, and extends across the full protein-protein interface, contacting solvent on the distal side. Thus, and although the structure of the potent C20' ureas and their optimization may appear unusual on a first inspection, they represent rational structural additions to a specific site on the natural product with appropriate conformational constraints needed to further enhance disruption of the target protein-protein interaction.

More provocatively, the activity of a ultra-potent analogue (IC$_{50}$'s 50-75 pM) suggest that it is not likely or even possible that their cellular functional activity is derived from stoichiometric occupancy of the relatively large number of intracellular tubulin binding sites. Rather, their potency suggests sub-stoichiometric or catalytic occupancy of candidate binding sites is sufficient to disrupt tubulin dynamics and assembly during mitosis. The question these ultra-potent vinblastines pose is whether sub-stoichiometric binding site occupancy is sufficient to trap polymerizing microtubulin in non-productive conformations, or whether such compounds serve catalytically to actively disassemble microtubulin.

In recent studies, the inventor and co-workers reported concise 12 step total syntheses of vinblastine and related natural products [(a) Ishikawa et al., *J. Am. Chem. Soc.* 2008, 130, 420; (b) Ishikawa et al., *J. Am. Chem. Soc.* 2009, 131, 4904; and (c) Gotoh et al., *J. Am. Chem. Soc.* 2012, 134, 13240] based in part on introduction of a powerful single-pot two-step diastereoselective Fe(III)-promoted vindoline/catharanthine coupling and subsequent Fe(III)-NaBH$_4$/air mediated hydrogen atom initiated free radical C20' oxidation that was extended for use of alternative free radical traps.[8] [(a) Leggans et al., *Org. Lett.* 2012, 14, 1428; and (b) Barker et al., *J. Am. Chem. Soc.* 2012, 134, 13588.] This methodology, inspired by the structure of vinblastine, has permitted systematic studies of the effects of deep-seated structural changes within either the lower vindoline or upper catharanthine-derived velbanamine subunits [Sears et al., *Acc. Chem. Res.* 2015, 48, 653].

Supporting Information

General Procedures

All commercial reagents were used without further purification unless otherwise noted. All reactions were performed in oven-dried (200° C.) glassware and under an inert atmosphere of anhydrous Ar unless otherwise noted. Column chromatography was performed with silica gel 60. TLC was performed on EMD Millipore silica gel (250 μm) F254 glass plates and spots visualized by UV. PTLC was performed on EMD Millipore silica gel (250 and 500 μm) F254 glass plates.

Optical rotations were determined on a Rudolph Research Analytical Autopol III automatic polarimeter using the sodium D line (λ=589 nm) at room temperature (23° C.) and are reported as follows: $[\alpha]_D^{23}$, concentration (c=g/100 mL), and solvent.

$^1$H NMR was recorded on a Bruker 500 MHz and 600 MHz spectrometers. Chemical shifts are reported in ppm from an internal standard of residual CHCl$_3$ (δ 7.26 for 1H). Proton chemical data are reported as follows: chemical shift (δ), multiplicity (ovlp=overlapping, br=broad, s=singlet, d=doublet, t=triplet, q=quartet, m=multiplet), coupling constant, and integration.

High resolution mass spectra were obtained on an Agilent ESI-TOF/MS using Agilent ESI-L low concentration tuning mix as internal high resolution calibration standards. The purity of each tested compound (>95%) was determined on an Agilent 1100 LC/MS instrument using a ZORBAX SB-C8 column (3.5 mm, 4.6 mm×50 mm, with a flow rate of 0.75 mL/minute and detection at 220 and 254 nm) with a 10-98% acetonitrile/water/0.1% formic acid gradient.

General Method for the Synthesis of Vinblastine C20'-Ureas

A solution of 20'-aminovinblastine (6, 60 mg, 0.074 mmol) and N,N-diisopropylethylamine (i-Pr$_2$NEt, 23 μL, 0.18 mmol) in anhydrous CH$_2$Cl$_2$ (3 mL) was cooled to 0° C. and treated with a solution of triphosgene (8.7 mg, 0.030 mmol) in anhydrous CH$_2$Cl$_2$ (2 mL). The reaction mixture was stirred for 15 minutes, after which the mixture was taken up in a syringe and portioned into vials (up to 6) containing individual free base secondary amines (2 equiv with respect to 6). Each vial containing the intermediate vinblastine 20'-isocyanate was then treated with i-Pr$_2$NEt (2 equiv with respect to 6). The reactions were allowed to proceed overnight (about 18 hours), after which the mixtures were diluted with EtOAc (10×reaction volume). The diluted reactions were extracted with saturated aq. NaHCO$_3$ and saturated aq. NaCl.

The organic layers were dried over Na$_2$SO$_4$. The products were isolated by PTLC using a 95:5:3 EtOAc:MeOH:NEt$_3$ mobile phase. Note: Just prior to use in urea formations, 2-Boc-N-(acyl)-5-aminoisoindolines were deprotected by treatment with 40% trifluoroacetic acid (TFA) in CH$_2$Cl$_2$. After reacting for 20 minutes, the solvent was removed with a stream of nitrogen and the residues were further dried under high vacuum. The deprotected isoindolines were used without further purification and an extra 5 equiv i-Pr$_2$NEt was added to the urea formation reaction to neutralize residual TFA.

Vinblastine C20' Isocyanate

Yield: 26.1 mg (62%), white solid. $^1$H NMR (500 MHz, CDCl$_3$) δ 9.82 (s, 1H), 8.04 (s, 1H), 7.52 (d, J=7.8 Hz, 1H), 7.23-7.04 (m, 3H), 6.63 (s, 1H), 6.12 (s, 1H), 5.85 (dd, J=10.4, 4.6 Hz, 1H), 5.48 (s, 1H), 5.30 (d, J=10.2 Hz, 1H), 4.00 (t, J=14.2 Hz, 1H), 3.85-3.77 (m, 6H), 3.72 (s, 1H), 3.69-3.51 (m, 4H), 3.49-3.24 (m, 4H), 3.24-3.09 (m, 2H), 2.98 (d, J=13.6 Hz, 1H), 2.88-2.75 (m, 2H), 2.70 (s, 3H), 2.44 (q, J=10.2 Hz, 1H), 2.36 (d, J=13.7 Hz, 1H), 2.25 (d, J=15.3 Hz, 1H), 2.17 (dt, J=15.1, 8.3 Hz, 1H), 2.11 (s, 3H), 1.87-1.75 (m, 2H), 1.71-1.58 (m, 2H), 1.49-1.39 (m, 1H), 1.39-1.29 (m, 2H), 0.96 (t, J=7.4 Hz, 3H), 0.83 (t, J=7.4 Hz, 3H), 0.80-0.71 (m, 1H). HRESI-TOF m/z 836.4230 (C$_{47}$H$_{57}$N$_5$O$_9$+H$^+$, required 836.4229). $[\alpha]_D^{23}$ +27 (c 0.7, CHCl$_3$).

Compound 10

Yield: 5.5 mg (53%), white solid. $^1$H NMR (500 MHz, CDCl$_3$) δ 9.80 (s, 1H), 8.00 (s, 1H), 7.50 (d, J=8.0 Hz, 1H), 7.20-7.07 (m, 3H), 6.61 (s, 1H), 6.09 (s, 1H), 5.85 (dd, J=10.4, 4.5 Hz, 1H), 5.47 (s, 1H), 5.30 (d, J=10.2 Hz, 1H), 4.27 (s, 1H), 3.96-3.83 (m, 2H), 3.83-3.76 (m, 7H), 3.74 (s, 1H), 3.68 (t, J=9.6 Hz, 1H), 3.58 (s, 3H), 3.56-3.50 (m, 1H), 3.37 (dd, J=16.2, 5.1 Hz, 2H), 3.33-3.10 (m, 6H), 2.82 (d, J=16.1 Hz, 2H), 2.71 (s, 3H), 2.66 (s, 1H), 2.60 (d, J=13.8 Hz, 1H), 2.49-2.36 (m, 2H), 2.30 (s, 6H), 2.24-2.14 (m, 3H), 2.11 (s, 3H), 1.85-1.71 (m, 4H), 1.49-1.40 (m, 1H), 1.38-1.21 (m, 3H), 0.85-0.72 (m, 7H). HRESI-TOF m/z 950.5385 (C$_{53}$H$_{71}$N$_7$O$_9$+H$^+$, required 950.5386). $[\alpha]_D^{23}$ −3 (c 0.2, CHCl$_3$).

Compound 11

Yield: 5.6 mg, (54%), white solid. $^1$H NMR (500 MHz, CDCl$_3$) δ 9.81 (s, 1H), 7.99 (s, 1H), 7.50 (d, J=8.2 Hz, 1H), 7.19-7.07 (m, 3H), 6.62 (s, 1H), 6.10 (s, 1H), 5.90-5.82 (m, 1H), 5.47 (s, 1H), 5.30 (d, J=10.1 Hz, 1H), 4.23 (s, 1H), 3.98-3.84 (m, 3H), 3.82-3.79 (m, 6H), 3.78-3.75 (m, 1H), 3.74 (s, 1H), 3.57 (s, 3H), 3.50-3.42 (m, 1H), 3.37 (dd, J=16.3, 4.9 Hz, 2H), 3.33-3.12 (m, 6H), 2.83 (d, J=16.0 Hz, 2H), 2.71 (s, 3H), 2.67 (s, 1H), 2.59 (d, J=14.1 Hz, 1H), 2.49-2.38 (m, 2H), 2.32 (s, 6H), 2.18 (d, J=7.3 Hz, 3H), 2.11 (s, 3H), 1.87-1.76 (m, 3H), 1.71-1.64 (m, 2H), 1.39-1.27 (m, 3H), 0.84-0.74 (m, 7H). HRESI-TOF m/z 950.5351 (C$_{53}$H$_{71}$N$_7$O$_9$+H$^+$, required 950.5386). $[\alpha]_D^{23}$ +2 (c 0.2, CHCl$_3$).

Compound 12

Yield: 5.4 mg (35%), white solid. $^1$H NMR (600 MHz, CDCl$_3$) δ 9.77 (s, 1H), 7.96 (s, 1H), 7.50 (d, J=7.5 Hz, 1H), 7.19-7.06 (m, 3H), 6.65 (s, 1H), 6.08 (s, 1H), 5.86 (dd, J=10.0, 4.4 Hz, 1H), 5.48 (s, 1H), 5.31 (d, J=10.2 Hz, 1H), 4.46 (s, 1H), 4.29 (s, 1H), 3.94 (t, J=12.6 Hz, 1H), 3.87-3.81 (m, 1H), 3.80 (s, 3H), 3.78 (s, 3H), 3.75 (s, 1H), 3.70-3.62 (m, 1H), 3.59-3.53 (m, 5H), 3.46-3.35 (m, 3H), 3.31 (td, J=9.1, 4.3 Hz, 1H), 3.26-3.17 (m, 3H), 3.13-3.05 (m, 2H), 2.81 (d, J=15.8 Hz, 1H), 2.71 (s, 3H), 2.62 (d, J=13.0 Hz, 1H), 2.44 (q, J=9.2 Hz, 1H), 2.32 (d, J=12.3 Hz, 1H), 2.24-2.16 (m, 1H), 2.14-2.05 (m, 7H), 1.85-1.76 (m, 3H), 1.57-1.51 (m, 2H), 1.47-1.35 (m, 4H), 1.16-1.11 (m, 1H), 0.85-0.81 (m, 4H), 0.78 (t, J=6.9 Hz, 3H). HRESI-TOF m/z 923.4909 (C$_{51}$H$_{66}$N$_6$O$_{10}$+H$^+$ required 923.4913). $[\alpha]_D^{23}$ −3 (c 0.3, CHCl$_3$).

Compound 13

Yield: 5.4 mg (35%), white solid. $^1$H NMR (600 MHz, CDCl$_3$) δ 9.77 (s, 1H), 7.98 (s, 1H), 7.51 (d, J=7.7 Hz, 1H), 7.23-7.05 (m, 3H), 6.64 (s, 1H), 6.08 (s, 1H), 5.86 (dd, J=10.1, 4.2 Hz, 1H), 5.48 (s, 1H), 5.31 (d, J=10.2 Hz, 1H), 4.55 (s, 1H), 4.31 (s, 1H), 3.90 (t, J=13.2 Hz, 1H), 3.80 (s, 3H), 3.77 (s, 3H), 3.75 (s, 1H), 3.71-3.58 (m, 5H), 3.55 (s, 3H), 3.41-3.28 (m, 4H), 3.22 (s, 3H), 3.14-3.02 (m, 2H), 2.81 (d, J=16.1 Hz, 1H), 2.71 (s, 3H), 2.62 (d, J=13.3 Hz, 1H), 2.44 (q, J=10.0 Hz, 1H), 2.28 (d, J=12.8 Hz, 1H), 2.24-2.17 (m, 1H), 2.11 (s, 3H), 2.04-2.01 (m, 2H), 1.85-1.76 (m, 2H), 1.57-1.52 (m, 2H), 1.47-1.39 (m, 3H), 1.38-1.34 (m, 1H), 0.84-0.80 (m, 4H), 0.77 (t, J=6.8 Hz, 3H). HRESI-TOF m/z 923.4907 (C$_{51}$H$_{66}$N$_6$O$_{10}$+H$^+$, required 923.4913). $[\alpha]_D^{23}$ −54 (c 0.3, CHCl$_3$).

Compound 14

Yield: 6.9 mg (43%), white solid. $^1$H NMR (600 MHz, CDCl$_3$) δ 9.83 (s, 1H), 8.00 (s, 1H), 7.49 (s, 1H), 7.23-7.04 (m, 3H), 6.62 (s, 1H), 6.10 (s, 1H), 5.86 (dd, J=9.5, 3.7 Hz, 1H), 5.46 (s, 1H), 5.30 (d, J=10.2 Hz, 1H), 4.23 (s, 1H), 4.01 (s, 1H), 3.96-3.91 (m, 3H), 3.84-3.77 (m, 7H), 3.74 (s, 1H), 3.66-3.52 (m, 8H), 3.40-3.37 (m, 1H), 3.37-3.34 (m, 1H), 3.33-3.28 (m, 5H), 3.24-3.12 (m, 3H), 2.83 (d, J=16.0 Hz, 1H), 2.71 (s, 3H), 2.64-2.54 (m, 1H), 2.52-2.34 (m, 2H), 2.29-2.14 (m, 2H), 2.14-2.06 (m, 5H), 1.91-1.73 (m, 4H), 1.39-1.30 (m, 2H), 1.29-1.22 (m, 1H), 0.87-0.70 (m, 7H). HRESI-TOF m/z 937.5067 ($C_{52}H_{68}N_6O_{10}$+H$^+$ required 937.5069). $[\alpha]_D^{23}$ +5 (c 0.3, CHCl$_3$).

Compound 15

Yield: 6.8 mg (43%), white solid. $^1$H NMR (600 MHz, CDCl$_3$) δ 9.83 (s, 1H), 8.01 (s, 1H), 7.50 (s, 1H), 7.24-7.01 (m, 3H), 6.62 (s, 1H), 6.10 (s, 1H), 5.86 (d, J=5.8 Hz, 1H), 5.46 (s, 1H), 5.30 (d, J=10.2 Hz, 1H), 4.25 (s, 1H), 4.02 (s, 1H), 3.95-3.88 (m, 1H), 3.83-3.77 (m, 7H), 3.74 (s, 1H), 3.70-3.66 (m, 1H), 3.63-3.50 (m, 7H), 3.45-3.33 (m, 6H), 3.31-3.27 (m, 1H), 3.26-3.11 (m, 3H), 2.83 (d, J=16.2 Hz, 1H), 2.71 (s, 3H), 2.63-2.54 (m, 1H), 2.51-2.33 (m, 2H), 2.27-2.13 (m, 2H), 2.13-2.05 (m, 5H), 1.91-1.74 (m, 3H), 1.48-1.29 (m, 3H), 1.28-1.22 (m, 1H), 0.90-0.66 (m, 7H). HRESI-TOF m/z 937.5064 ($C_{52}H_{68}N_6O_{10}$+H$^+$ required 937.5069). $[\alpha]_D^{23}$ +9 (c 0.3, CHCl$_3$)

Compound 17

Yield 6.7 mg (61%), white solid. $^1$H NMR (500 MHz, CDCl$_3$) δ 9.81 (s, 1H), 8.00 (s, 1H), 7.50 (d, J=7.7 Hz, 1H), 7.21-7.06 (m, 3H), 6.63 (s, 1H), 6.10 (s, 1H), 5.85 (dd, J=10.2, 4.1 Hz, 1H), 5.47 (s, 1H), 5.38-5.21 (m, 2H), 4.27 (s, 1H), 3.96-3.84 (m, 2H), 3.80 (d, J=1.5 Hz, 8H), 3.76-3.69 (m, 2H), 3.68-3.62 (m, 1H), 3.62-3.56 (m, 4H), 3.41-3.33 (m, 2H), 3.30 (td, J=10.1, 9.6, 4.8 Hz, 1H), 3.25-3.11 (m, 4H), 2.82 (d, J=16.3 Hz, 1H), 2.71 (s, 3H), 2.66 (s, 1H), 2.60 (d, J=13.6 Hz, 1H), 2.44 (td, J=10.1, 6.5 Hz, 1H), 2.38 (d, J=12.5 Hz, 1H), 2.22-2.14 (m, 2H), 2.11 (s, 3H), 1.87-1.69 (m, 4H), 1.46-1.40 (m, 1H), 1.37-1.31 (m, 1H), 1.28-1.25 (m, 1H), 0.84-0.74 (m, 7H). HRESI-TOF m/z 925.4841 ($C_{51}H_{65}FN_6O_9$+H$^+$, required 925.4870). $[\alpha]_D^{23}$ −0.9 (c 0.2, CHCl$_3$).

Compound 18

Yield: 6.8 mg, (62%), white solid. $^1$H NMR (500 MHz, CDCl$_3$) δ 9.80 (s, 1H), 7.99 (s, 1H), 7.50 (d, J=7.7 Hz, 1H), 7.20-7.07 (m, 3H), 6.63 (s, 1H), 6.10 (s, 1H), 5.85 (dd, J=10.3, 4.2 Hz, 1H), 5.47 (s, 1H), 5.39-5.17 (m, 2H), 4.30 (s, 1H), 3.93-3.82 (m, 2H), 3.81-3.72 (m, 10H), 3.71-3.61 (m, 2H), 3.58 (s, 3H), 3.42-3.33 (m, 2H), 3.30 (dq, J=9.3, 4.4 Hz, 1H), 3.26-3.10 (m, 4H), 2.82 (d, J=15.9 Hz, 1H), 2.71 (s, 3H), 2.66 (s, 1H), 2.59 (d, J=13.5 Hz, 1H), 2.44 (td, J=10.4, 6.7 Hz, 1H), 2.37 (d, J=13.7 Hz, 1H), 2.24-2.16 (m, 2H), 2.11 (s, 3H), 1.87-1.70 (m, 4H), 1.43 (dt, J=13.7, 7.5 Hz, 1H), 1.34 (dd, J=14.5, 7.4 Hz, 1H), 1.27 (d, J=5.6 Hz, 1H), 0.85-0.74 (m, 7H). HRESI-TOF m/z 925.4843 ($C_{51}H_{65}FN_6O_9$+H$^+$, required 925.4870). $[\alpha]_D^{23}$ +1.8 (c 0.5, CHCl$_3$).

Compound 20

Yield: 5.3 mg (52%), white solid. $^1$H NMR (500 MHz, CDCl$_3$) δ 9.78 (s, 1H), 7.99 (s, 1H), 7.50 (d, J=7.7 Hz, 1H), 7.19-7.06 (m, 3H), 6.64 (s, 1H), 6.09 (s, 1H), 5.85 (dd, J=10.3, 4.3 Hz, 1H), 5.47 (s, 1H), 5.30 (d, J=10.3 Hz, 1H), 4.29 (s, 1H), 3.93 (dd, J=10.0, 7.4 Hz, 1H), 3.89-3.82 (m, 1H), 3.80 (s, 6H), 3.77-3.73 (m, 2H), 3.73-3.61 (m, 3H), 3.57 (s, 3H), 3.38 (dd, J=16.1, 4.1 Hz, 2H), 3.33-3.27 (m, 1H), 3.25-3.06 (m, 5H), 2.82 (d, J=16.1 Hz, 1H), 2.71 (s, 3H), 2.66 (s, 1H), 2.60 (d, J=13.6 Hz, 1H), 2.49-2.31 (m, 4H), 2.24-2.14 (m, 2H), 2.11 (s, 3H), 1.87-1.75 (m, 3H), 1.70 (dt, J=15.4, 7.1 Hz, 1H), 1.54-1.48 (m, 1H), 1.39-1.31 (m, 1H), 1.25-1.19 (m, 1H), 0.87-0.72 (m, 7H). HRESI-TOF m/z 932.4887 ($C_{52}H_{65}N_7O_9$+H$^+$, required 932.4916). $[\alpha]_D^{23}$ −0.7 (c 0.2, CHCl$_3$).

Compound 21

Yield: 5.9 mg (58%), white solid. $^1$H NMR (500 MHz, CDCl$_3$) δ 9.78 (s, 1H), 7.97 (s, 1H), 7.50 (d, J=7.8 Hz, 1H), 7.20-7.07 (m, 3H), 6.63 (s, 1H), 6.09 (s, 1H), 5.86 (dd, J=10.6, 4.3 Hz, 1H), 5.47 (s, 1H), 5.31 (d, J=10.4 Hz, 1H), 4.29 (s, 1H), 4.00 (dd, J=10.0, 7.8 Hz, 1H), 3.90-3.82 (m, 1H), 3.80 (s, 6H), 3.77-3.73 (m, 2H), 3.71-3.61 (m, 3H), 3.57 (s, 3H), 3.38 (d, J=11.9 Hz, 2H), 3.33-3.27 (m, 1H), 3.25-3.05 (m, 5H), 2.82 (d, J=15.9 Hz, 1H), 2.71 (s, 3H), 2.66 (s, 1H), 2.61 (d, J=13.5 Hz, 1H), 2.49-2.40 (m, 2H), 2.38-2.29 (m, 2H), 2.22-2.13 (m, 2H), 2.11 (s, 3H), 1.86-1.76 (m, 3H), 1.72-1.64 (m, 1H), 1.56-1.50 (m, 1H), 1.40-1.32 (m, 1H), 1.22 (dd, J=14.5, 5.6 Hz, 1H), 0.85-0.75 (m, 7H). HRESI-TOF m/z 932.4892 ($C_{52}H_{65}N_7O_9$+H$^+$, required 932.4916). $[\alpha]_D^{23}$ +3 (c 0.4, CHCl$_3$).

Compound 22

Yield: 10.1 mg (85%), white solid. $^1$H NMR (500 MHz, CDCl$_3$) δ 9.82 (s, 1H), 7.99 (s, 1H), 7.49 (d, J=7.8 Hz, 1H), 7.20-7.03 (m, 3H), 6.63 (s, 1H), 6.10 (s, 1H), 5.94-5.74 (m, 3H), 5.47 (s, 1H), 5.30 (d, J=10.2 Hz, 1H), 4.40-4.25 (m, 4H), 4.24 (s, 1H), 3.90 (d, J=14.0 Hz, 2H), 3.80 (s, 3H), 3.79 (s, 3H), 3.74 (s, 1H), 3.58 (s, 3H), 3.37 (dd, J=15.8, 5.1 Hz, 2H), 3.32-3.27 (m, 1H), 3.26-3.11 (m, 4H), 2.82 (d, J=16.2 Hz, 1H), 2.71 (s, 3H), 2.60 (d, J=13.7 Hz, 1H), 2.49-2.35 (m, 2H), 2.28-2.13 (m, 2H), 2.10 (s, 3H), 1.90-1.75 (m, 3H), 1.72 (d, J=14.8 Hz, 1H), 1.39-1.21 (m, 4H), 0.84-0.74 (m, 7H). HRESI-TOF m/z 905.4807 ($C_{51}H_{64}N_6O_9$+H$^+$, required 905.4807). $[\alpha]_D^{23}$ −0.5 (c 0.3, CHCl$_3$).

Compound 24

Yield: 17.5 mg (65%), white solid. $^1$H NMR (600 MHz, CDCl$_3$) δ 9.84 (s, 1H), 8.02 (s, 1H), 7.51 (d, J=7.8 Hz, 1H), 7.20-7.03 (m, 3H), 6.62 (s, 1H), 6.10 (s, 1H), 5.85 (ddd, J=10.2, 5.0, 1.6 Hz, 1H), 5.47 (s, 1H), 5.30 (dt, J=10.1, 2.0 Hz, 1H), 4.37 (s, 1H), 4.01-3.84 (m, 2H), 3.81-3.78 (m, 6H), 3.73 (s, 1H), 3.62-3.54 (m, 5H), 3.54-3.47 (m, 2H), 3.40-3.34 (m, 2H), 3.32-3.22 (m, 3H), 3.19-3.10 (m, 2H), 2.83 (d, J=16.1 Hz, 1H), 2.71 (s, 3H), 2.66 (s, 1H), 2.58 (d, J=13.8 Hz, 1H), 2.49-2.36 (m, 2H), 2.25-2.14 (m, 2H), 2.10 (s, 3H), 1.90 (dd, J=13.9, 7.4 Hz, 1H), 1.83 (td, J=11.2, 6.0 Hz, 3H), 1.79-1.72 (m, 3H), 1.66-1.59 (m, 3H), 1.55 (dt, J=7.6, 3.8 Hz, 2H), 1.37-1.26 (m, 4H), 0.81 (t, J=7.4 Hz, 3H), 0.75 (t, J=7.4 Hz, 4H). HRESI-TOF m/z 935.5267 ($C_{53}H_{70}N_6O_9$+H$^+$ required 935.5277). $[\alpha]_D^{23}$ +0.7 (c 0.4, CHCl$_3$).

Compound 25

Yield: 4.9 mg (49%), white solid. $^1$H NMR (500 MHz, CDCl$_3$) δ 9.82 (s, 1H), 8.01 (s, 1H), 7.51 (d, J=7.7 Hz, 1H), 7.19-7.07 (m, 3H), 6.62 (s, 1H), 6.10 (s, 1H), 5.85 (dd, J=10.5, 4.4 Hz, 1H), 5.47 (s, 1H), 5.30 (d, J=10.5 Hz, 1H), 4.37 (s, 1H), 3.89 (t, J=12.5 Hz, 1H), 3.85-3.75 (m, 7H), 3.74 (s, 1H), 3.59 (s, 3H), 3.55-3.49 (m, 3H), 3.40-3.33 (m, 2H), 3.33-3.21 (m, 3H), 3.20-3.11 (m, 2H), 2.83 (d, J=15.8 Hz, 1H), 2.71 (s, 3H), 2.66 (s, 1H), 2.59 (d, J=13.4 Hz, 1H), 2.50-2.35 (m, 2H), 2.25-2.13 (m, 2H), 2.11 (s, 3H), 1.92 (dd, J=13.7, 7.5 Hz, 1H), 1.87-1.73 (m, 5H), 1.72-1.59 (m, 6H), 1.38-1.24 (m, 6H), 0.81 (t, J=7.4 Hz, 3H), 0.76 (t, J=7.4 Hz, 3H). HRESI-TOF m/z 949.5416 ($C_{54}H_{72}N_6O_9$+H$^+$, required 949.5439). $[\alpha]_D^{23}$ +6 (c 0.2, CHCl$_3$).

Compound 26

Yield: 10.7 mg (87%), white solid. $^1$H NMR (500 MHz, CDCl$_3$) δ 9.83 (s, 1H), 8.03 (s, 1H), 7.50 (d, J=7.8 Hz, 1H), 7.18-7.07 (m, 3H), 6.61 (s, 1H), 6.11 (s, 1H), 5.84 (dd, J=10.4, 4.5 Hz, 1H), 5.47 (s, 1H), 5.29 (d, J=10.2 Hz, 1H), 4.50 (s, 1H), 4.29 (s, 2H), 3.88-3.78 (m, 8H), 3.73 (s, 1H), 3.60 (s, 3H), 3.40-3.24 (m, 5H), 3.19-3.11 (m, 2H), 2.82 (d, J=16.1 Hz, 1H), 2.71 (s, 3H), 2.58 (d, J=13.8 Hz, 1H), 2.48-2.35 (m, 2H), 2.25 (d, J=14.4 Hz, 1H), 2.17 (dt, J=15.0, 8.3 Hz, 1H), 2.10 (s, 3H), 1.89 (d, J=7.3 Hz, 4H), 1.87-1.73 (m, 4H), 1.68 (d, J=14.6 Hz, 2H), 1.46 (d, J=7.4 Hz, 4H), 1.39-1.24 (m, 5H), 0.81 (t, J=7.3 Hz, 3H), 0.78-0.72 (m, 4H). HRESI-TOF m/z 933.5119 ($C_{53}H_{68}N_6O_9$+H$^+$, required 933.5120). $[\alpha]_D^{23}$ +2 (c 0.4, CHCl$_3$).

Compound 27

Yield: 11.6 mg (90%), white solid. $^1$H NMR (500 MHz, CDCl$_3$) δ 9.83 (s, 1H), 8.03 (s, 1H), 7.49 (d, J=7.9 Hz, 1H), 7.17-7.07 (m, 1H), 6.62 (s, 1H), 6.11 (s, 1H), 5.85 (dd, J=10.5, 4.6 Hz, 1H), 5.47 (s, 1H), 5.29 (d, J=10.1 Hz, 1H), 4.54 (s, 1H), 3.89-3.78 (m, 8H), 3.74 (s, 1H), 3.72-3.65 (m, 4H), 3.52 (s, 3H), 3.37 (dd, J=16.0, 3.9 Hz, 2H), 3.32-3.22 (m, 3H), 3.14 (d, J=12.0 Hz, 2H), 3.10-2.99 (m, 4H), 2.82 (d, J=16.0 Hz, 1H), 2.71 (s, 3H), 2.62 (d, J=13.8 Hz, 1H), 2.49-2.36 (m, 2H), 2.29 (d, J=14.0 Hz, 1H), 2.23-2.14 (m, 1H), 2.10 (s, 3H), 1.87-1.75 (m, 4H), 1.35-1.25 (m, 4H), 0.82-0.77 (m, 4H), 0.75 (t, J=7.4 Hz, 3H). HRESI-TOF m/z 983.5278 (C$_{57}$H$_{70}$N$_6$O$_9$+H$^+$, required 983.5277). [α]$_D^{23}$ −0.6 (c 0.4, CHCl$_3$).

Compound 28

Yield: 10.4 mg (52%), white solid. $^1$H NMR (500 MHz, CDCl$_3$) δ 9.80 (s, 1H), 8.62 (s, 1H), 8.52 (d, J=5.1 Hz, 1H), 7.98 (s, 1H), 7.47 (d, J=7.8 Hz, 1H), 7.29 (d, J=5.1 Hz, 1H), 7.17-7.04 (m, 3H), 6.64 (s, 1H), 6.11 (s, 1H), 5.85 (dd, J=10.4, 4.4 Hz, 1H), 5.47 (s, 1H), 5.30 (d, J=10.2 Hz, 1H), 5.05-4.82 (m, 4H), 4.43 (s, 1H), 3.96 (t, J=13.7 Hz, 1H), 3.90-3.83 (m, 1H), 3.82 (s, 3H), 3.80 (s, 3H), 3.75 (s, 1H), 3.52 (s, 3H), 3.42-3.34 (m, 2H), 3.34-3.27 (m, 1H), 3.25-3.12 (m, 4H), 2.82 (d, J=16.1 Hz, 1H), 2.72 (s, 3H), 2.63 (d, J=13.6 Hz, 1H), 2.50-2.43 (m, 1H), 2.40 (d, J=16.0 Hz, 1H), 2.27 (d, J=14.2 Hz, 1H), 2.23-2.15 (m, 1H), 2.11 (s, 3H), 1.89-1.73 (m, 4H), 1.50-1.40 (m, 1H), 1.39-1.26 (m, 3H), 0.84-0.76 (m, 7H). HRESI-TOF m/z 956.4915 (C$_{54}$H$_{65}$N$_7$O$_9$+H$^+$, required 956.4916). [α]$_D^{23}$ −8 (c 0.4, CHCl$_3$).

Compound 29

Yield: 11.0 mg (55%), white solid. $^1$H NMR (500 MHz, CDCl$_3$) δ 9.83 (s, 1H), 8.49 (dd, J=4.9, 1.5 Hz, 1H), 8.00 (s, 1H), 7.67-7.60 (m, 1H), 7.52-7.43 (m, 1H), 7.20 (dd, J=7.7, 4.9 Hz, 1H), 7.17-7.02 (m, 3H), 6.64 (s, 1H), 6.12 (s, 1H), 5.92-5.78 (m, 1H), 5.48 (s, 1H), 5.29 (d, J=10.1 Hz, 1H), 5.01-4.84 (m, 4H), 4.45 (s, 1H), 3.99 (t, J=13.7 Hz, 1H), 3.87 (d, J=13.7 Hz, 1H), 3.81 (s, 3H), 3.80 (s, 3H), 3.74 (s, 1H), 3.53 (s, 3H), 3.42-3.35 (m, 2H), 3.30 (td, J=9.6, 4.4 Hz, 1H), 3.27-3.12 (m, 4H), 2.82 (d, J=16.1 Hz, 1H), 2.71 (s, 3H), 2.66-2.62 (m, 1H), 2.48-2.38 (m, 2H), 2.28 (d, J=14.3 Hz, 1H), 2.24-2.15 (m, 1H), 2.10 (s, 3H), 1.85-1.78 (m, 4H), 1.45 (dq, J=14.0, 6.7 Hz, 1H), 1.37-1.27 (m, 3H), 0.83-0.78 (m, 7H). HRESI-TOF m/z 956.4915 (C$_{54}$H$_{65}$N$_7$O$_9$+H$^+$, required 956.4916). [α]$_D^{23}$ −6 (c 0.4, CHCl$_3$).

Compound 30

Yield: 10.4 mg (59%), white solid. $^1$H NMR (500 MHz, CDCl$_3$) δ 9.91 (s, 1H), 8.08 (s, 1H), 7.56 (d, J=7.8 Hz, 1H), 7.27 (d, J=7.8 Hz, 1H), 7.25-7.06 (m, 5H), 6.71 (s, 1H), 6.20 (s, 1H), 5.93 (dd, J=10.1, 4.4 Hz, 1H), 5.56 (s, 1H), 5.37 (d, J=10.1 Hz, 1H), 5.01-4.84 (m, 4H), 4.48 (s, 1H), 4.03 (t, J=13.4 Hz, 1H), 3.95 (d, J=12.1 Hz, 1H), 3.90 (s, 3H), 3.88 (s, 3H), 3.82 (s, 1H), 3.59 (s, 3H), 3.51-3.42 (m, 2H), 3.42-3.19 (m, 5H), 2.90 (d, J=16.1 Hz, 1H), 2.80 (s, 3H), 2.71 (d, J=13.8 Hz, 1H), 2.57-2.46 (m, 2H), 2.43 (s, 3H), 2.38 (d, J=13.4 Hz, 1H), 2.32-2.23 (m, 1H), 2.19 (s, 3H), 1.99-1.83 (m, 4H), 1.61-1.47 (m, 1H), 1.48-1.30 (m, 3H), 0.95-0.81 (m, 7H). HRESI-TOF m/z 969.5119 (C$_{56}$H$_{68}$N$_6$O$_9$+H$^+$, required 969.5120). [α]$_D^{23}$ −0.7 (c 0.4, CHCl$_3$).

Compound 31

Yield: 7.4 mg (63%), white solid. $^1$H NMR (500 MHz, CDCl$_3$) δ 9.82 (s, 1H), 7.99 (s, 1H), 7.47 (d, J=7.7 Hz, 1H), 7.16-7.05 (m, 3H), 7.04-6.91 (m, 2H), 6.63 (s, 1H), 6.11 (s, 1H), 5.85 (dd, J=9.9, 3.8 Hz, 1H), 5.47 (s, 1H), 5.29 (d, J=10.1 Hz, 1H), 4.95-4.74 (m, 4H), 4.40 (s, 1H), 3.95 (t, J=13.9 Hz, 1H), 3.86 (d, J=12.3 Hz, 1H), 3.82 (s, 3H), 3.80 (s, 3H), 3.74 (s, 1H), 3.52 (s, 3H), 3.42-3.34 (m, 2H), 3.33-3.28 (m, 1H), 3.28-3.11 (m, 4H), 2.82 (d, J=16.3 Hz, 1H), 2.72 (s, 3H), 2.63 (d, J=13.8 Hz, 1H), 2.49-2.36 (m, 2H), 2.28 (d, J=13.8 Hz, 1H), 2.24-2.14 (m, 1H), 2.11 (s, 3H), 1.87-1.76 (m, 4H), 1.38-1.20 (m, 4H), 0.84-0.76 (m, 7H). HRESI-TOF m/z 973.4869 (C$_{55}$H$_{65}$FN$_6$O$_9$+H$^+$ required 973.4870). [α]$_D^{23}$ −3 (c 0.4, CHCl$_3$).

Compound 32

Yield: 9.7 mg, (53%), white solid. $^1$H NMR (500 MHz, CDCl$_3$) δ 9.82 (s, 1H), 7.99 (s, 1H), 7.47 (d, J=7.9 Hz, 1H), 7.31 (s, 1H), 7.24 (s, 2H), 7.16-7.04 (m, 3H), 6.64 (s, 1H), 6.11 (s, 1H), 5.85 (dd, J=10.2, 4.4 Hz, 1H), 5.47 (s, 1H), 5.30 (d, J=10.3 Hz, 1H), 4.94-4.77 (m, 4H), 4.40 (s, 1H), 3.95 (t, J=13.1 Hz, 1H), 3.85 (d, J=13.9 Hz, 1H), 3.82 (s, 3H), 3.80 (s, 3H), 3.74 (s, 1H), 3.52 (s, 3H), 3.43-3.34 (m, 2H), 3.34-3.26 (m, 1H), 3.25-3.11 (m, 4H), 2.82 (d, J=16.0 Hz, 1H), 2.72 (s, 3H), 2.63 (d, J=13.6 Hz, 1H), 2.50-2.36 (m, 2H), 2.28 (d, J=13.7 Hz, 1H), 2.23-2.15 (m, 2H), 2.11 (s, 3H), 1.88-1.73 (m, 4H), 1.50-1.34 (m, 2H), 0.84-0.76 (m, 7H). HRESI-TOF m/z 989.4572 (C$_{55}$H$_{65}$ClN$_6$O$_9$+H$^+$, required 989.4574). [α]$_D^{23}$ −0.7 (c 0.2, CHCl$_3$).

Compound 33

Yield: 6.9 mg (56%), white solid. $^1$H NMR (500 MHz, CDCl$_3$) δ 9.82 (s, 1H), 7.98 (s, 1H), 7.50-7.45 (m, 2H), 7.40 (d, J=8.1 Hz, 1H), 7.19 (d, J=8.1 Hz, 1H), 7.16-7.04 (m, 3H), 6.64 (s, 1H), 6.11 (s, 1H), 5.85 (dd, J=11.0, 4.6 Hz, 1H), 5.48 (s, 1H), 5.33-5.26 (m, 1H), 4.95-4.72 (m, 4H), 4.40 (s, 1H), 3.95 (t, J=13.9 Hz, 1H), 3.85 (d, J=13.2 Hz, 1H), 3.82 (s, 3H), 3.80 (s, 3H), 3.74 (s, 1H), 3.52 (s, 3H), 3.43-3.34 (m, 2H), 3.32-3.27 (m, 1H), 3.26-3.11 (m, 4H), 2.82 (d, J=16.2 Hz, 1H), 2.72 (s, 3H), 2.63 (d, J=13.8 Hz, 1H), 2.50-2.34 (m, 2H), 2.27 (d, J=13.7 Hz, 1H), 2.24-2.15 (m, 1H), 2.11 (s, 3H), 1.88-1.75 (m, 4H), 1.37-1.25 (m, 4H), 0.83-0.75 (m, 7H). HRESI-TOF m/z 1033.4069 (C$_{55}$H$_{65}$BrN$_6$O$_9$+H$^+$, required 1033.4069). [α]$_D^{23}$ −2 (c 0.3, CHCl$_3$).

Compound 34

Yield: 10.2 mg (55%), white solid. $^1$H NMR (500 MHz, CDCl$_3$) δ 9.80 (s, 1H), 7.98 (s, 1H), 7.58 (s, 1H), 7.55 (d, J=8.2 Hz, 1H), 7.47 (d, J=7.8 Hz, 1H), 7.43 (d, J=8.0 Hz, 1H), 7.16-7.11 (m, 1H), 7.11-7.04 (m, 2H), 6.64 (s, 1H), 6.11 (s, 1H), 5.85 (dd, J=10.0, 3.8 Hz, 1H), 5.48 (s, 1H), 5.30 (d, J=10.0 Hz, 1H), 5.02-4.80 (m, 4H), 4.43 (s, 1H), 4.02-3.91 (m, 1H), 3.86 (d, J=14.0 Hz, 1H), 3.82 (s, 3H), 3.80 (s, 3H), 3.75 (s, 1H), 3.52 (s, 3H), 3.38 (dd, J=15.8, 4.9 Hz, 2H), 3.30 (td, J=8.7, 7.7, 3.8 Hz, 1H), 3.26-3.11 (m, 4H), 2.82 (d, J=16.0 Hz, 1H), 2.72 (s, 3H), 2.63 (d, J=13.7 Hz, 1H), 2.49-2.37 (m, 2H), 2.28 (d, J=13.1 Hz, 1H), 2.24-2.14 (m, 1H), 2.11 (s, 3H), 1.89-1.73 (m, 4H), 1.49-1.39 (m, 1H), 1.39-1.26 (m, 3H), 0.84 (d, J=3.3 Hz, 1H), 0.80 (t, J=7.4 Hz, 6H). HRESI-TOF m/z 1023.4837 (C$_{56}$H$_{65}$F$_3$N$_6$O$_9$+H$^+$, required 1023.4838). [α]$_D^{23}$ +0.8 (c 0.2, CHCl$_3$).

Compound 35

Yield: 3.8 mg (37%), white solid. $^1$H NMR (500 MHz, CDCl$_3$) δ 9.83 (s, 1H), 8.00 (s, 1H), 7.48 (d, J=8.1 Hz, 1H), 7.24-7.02 (m, 4H), 6.90-6.78 (m, 2H), 6.63 (s, 1H), 6.11 (s, 1H), 5.85 (dd, J=9.8, 4.0 Hz, 1H), 5.48 (s, 1H), 5.29 (d, J=9.4 Hz, 1H), 4.95-4.74 (m, 3H), 4.39 (s, 1H), 4.02-3.87 (m, 1H), 3.85-3.70 (m, 11H), 3.68-3.56 (m, 1H), 3.50 (s, 2H), 3.43-3.34 (m, 2H), 3.33-3.22 (m, 3H), 3.22-3.12 (m, 2H), 2.82 (d, J=16.5 Hz, 1H), 2.72 (s, 3H), 2.68-2.60 (m, 2H), 2.49-2.37 (m, 2H), 2.29 (d, J=14.3 Hz, 1H), 2.24-2.14 (m, 1H), 2.11 (s, 3H), 1.91-1.73 (m, 3H), 1.64 (d, J=12.5 Hz, 4H), 1.49-1.40 (m, 1H), 1.39-1.26 (m, 4H), 0.83-0.73 (m, 6H). HRESI-TOF m/z 985.5068 (C$_{56}$H$_{68}$N$_6$O$_{10}$+H$^+$, required 985.5075), [α]$_D^{23}$ +1 (c 0.2, CHCl$_3$).

Compound 36

Yield: 9.6 mg (82%), white solid. $^1$H NMR (500 MHz, CDCl$_3$) δ 9.83 (s, 1H), 8.01 (s, 1H), 7.54-7.45 (m, 1H), 7.20-7.02 (m, 4H), 6.69-6.57 (m, 3H), 6.11 (s, 1H), 5.84 (dd, J=10.3, 4.5 Hz, 1H), 5.47 (s, 1H), 5.29 (d, J=10.2 Hz, 1H), 4.85-4.67 (m, 4H), 4.37 (s, 1H), 3.94 (t, J=13.8 Hz, 1H), 3.84 (d, J=16.0 Hz, 1H), 3.81 (s, 3H), 3.80 (s, 3H), 3.74 (s, 1H), 3.66 (s, 2H), 3.50 (s, 3H), 3.43-3.33 (m, 2H), 3.34-3.21 (m, 3H), 3.21-3.10 (m, 2H), 2.82 (d, J=16.1 Hz, 1H), 2.71 (s, 3H), 2.62 (d, J=13.6 Hz, 1H), 2.49-2.34 (m, 2H), 2.33-2.23 (m, 1H), 2.18 (ddd, J=14.7, 9.3, 7.3 Hz, 1H), 2.10 (s, 3H), 1.89-1.74 (m, 4H), 1.38-1.16 (m, 4H), 0.79 (q, J=7.4 Hz, 7H). HRESI-TOF m/z 970.5072 (C$_{55}$H$_{67}$N$_7$O$_9$+H$^+$, required 970.5073). [α]$_D^{23}$ −2 (c 0.3, CHCl$_3$).

Compound 37

Yield: 7.8 mg (65%), white solid. $^1$H NMR (600 MHz, CDCl$_3$) δ 9.85 (s, 1H), 8.01 (s, 1H), 7.48 (d, J=7.9 Hz, 1H), 7.18-7.04 (m, 4H), 6.63 (s, 1H), 6.58-6.50 (m, 2H), 6.11 (s, 1H), 5.84 (dd, J=10.1, 3.9 Hz, 1H), 5.47 (s, 1H), 5.29 (d, J=10.2 Hz, 1H), 4.98-4.64 (m, 4H), 4.38 (s, 1H), 3.94 (t, J=13.2 Hz, 1H), 3.86-3.77 (m, 7H), 3.74 (s, 1H), 3.50 (s, 3H), 3.41-3.33 (m, 2H), 3.33-3.13 (m, 5H), 2.87-2.77 (m, 4H), 2.71 (s, 3H), 2.62 (d, J=13.7 Hz, 1H), 2.50-2.35 (m, 2H), 2.29 (d, J=13.0 Hz, 1H), 2.23-2.13 (m, 1H), 2.10 (s, 3H), 1.90-1.73 (m, 4H), 1.36-1.24 (m, 3H), 0.85-0.75 (m, 7H). HRESI-TOF m/z 984.5231 (C$_{56}$H$_{68}$N$_7$O$_9$+H$^+$, required 984.5229). [α]$_D^{23}$ +3 (c 0.3, CHCl$_3$).

Compound 38

Yield: 8.2 mg (68%), white solid. $^1$H NMR (600 MHz, CDCl$_3$) δ 9.85 (s, 1H), 8.01 (s, 1H), 7.48 (d, J=7.9 Hz, 1H), 7.18-7.11 (m, 2H), 7.11-7.05 (m, 2H), 6.73-6.61 (m, 3H), 6.11 (s, 1H), 5.84 (dd, J=10.2, 3.9 Hz, 1H), 5.47 (s, 1H), 5.29 (d, J=10.2 Hz, 1H), 4.93-4.71 (m, 4H), 4.38 (s, 1H), 3.94 (t, J=13.6 Hz, 1H), 3.86-3.77 (m, 7H), 3.74 (s, 1H), 3.50 (s, 3H), 3.37 (dd, J=16.0, 4.9 Hz, 2H), 3.33-3.12 (m, 5H), 2.93 (s, 6H), 2.82 (d, J=16.2 Hz, 1H), 2.71 (s, 3H), 2.62 (d, J=13.6 Hz, 1H), 2.48-2.36 (m, 2H), 2.30 (d, J=13.5 Hz, 1H), 2.23-2.14 (m, 1H), 2.10 (s, 3H), 1.91-1.71 (m, 4H), 1.58-1.51 (m, 1H), 1.37-1.23 (m, 3H), 0.85-0.73 (m, 7H). HRESI-TOF m/z 998.5386 (C$_{57}$H$_{71}$N$_7$O$_9$+H$^+$ required 998.5386). [α]$_D^{23}$ +2 (c 0.3, CHCl$_3$).

Compound 39

A solution of 36 (16 mg, 0.016 mmol) and propionaldehyde (1.3 µL, 0.017 mmol) in CH$_2$Cl$_2$ (0.5 mL) was treated with sodium triacetoxyborohydride (4.4 mg, 0.021 mmol). After stirring for 2 h, the reaction mixture was loaded directly onto a silica gel PTLC plate and developed with 95:5:3 EtOAc/MeOH/Et$_3$N. The purified product was isolated as a white solid: 11.5 mg, 69%. $^1$H NMR (500 MHz, CDCl$_3$) δ 9.83 (s, 1H), 8.01 (s, 1H), 7.48 (d, J=7.8 Hz, 1H), 7.21-6.94 (m, 4H), 6.63 (s, 1H), 6.54 (s, 2H), 6.22-6.01 (m, 1H), 5.84 (dd, J=10.4, 4.6 Hz, 1H), 5.48 (s, 1H), 5.29 (d, J=10.2 Hz, 1H), 4.91-4.52 (m, 4H), 4.37 (s, 1H), 4.02-3.88 (m, 1H), 3.89-3.76 (m, 7H), 3.74 (s, 1H), 3.50 (s, 3H), 3.43-3.34 (m, 2H), 3.31-3.11 (m, 5H), 3.11-3.01 (m, 2H), 2.82 (d, J=16.1 Hz, 1H), 2.71 (s, 3H), 2.62 (d, J=14.0 Hz, 1H), 2.50-2.36 (m, 2H), 2.29 (d, J=14.1 Hz, 1H), 2.24-2.14 (m, 1H), 2.10 (s, 3H), 1.89-1.74 (m, 4H), 1.71-1.53 (m, 4H), 1.37-1.22 (m, 3H), 1.03-0.90 (m, 3H), 0.86-0.71 (m, 7H). HRESI-TOF m/z 1012.5542 (C$_{58}$H$_{73}$N$_7$O$_9$+H$^+$, required 1012.5542). [α]$_D^{23}$ −0.5 (c 0.5, CHCl$_3$).

Compound 40

Compound 36 (16 mg, 0.016 mmol) was treated Ac$_2$O (800 µL) and catalytic HOAc (4 µL). The reaction was allowed to proceed for 1 h and was then quenched by the slow addition of saturated aqueous NaHCO$_3$. The aqueous solution was extracted with CH$_2$Cl$_2$ and the organic layers were combined and dried over Na$_2$SO$_4$. The product was purified by PTLC (SiO$_2$, 95:5:3 EtOAc:MeOH:NEt$_3$ mobile phase). The product was isolated as a white solid: 7.5 mg, (46%). $^1$H NMR (500 MHz, CDCl$_3$) δ 9.82 (s, 1H), 8.00 (s, 1H), 7.66 (s, 1H), 7.47 (d, J=8.0 Hz, 1H), 7.25-7.19 (m, 2H), 7.18-7.00 (m, 4H), 6.63 (s, 1H), 6.12 (s, 1H), 5.84 (dd, J=10.6, 4.6 Hz, 1H), 5.48 (s, 1H), 5.29 (d, J=10.3 Hz, 1H), 4.94-4.76 (m, 4H), 4.39 (s, 1H), 4.00-3.90 (m, 1H), 3.91-3.85 (m, 1H), 3.82 (s, 3H), 3.80 (s, 3H), 3.74 (s, 1H), 3.51 (s, 3H), 3.41-3.34 (m, 2H), 3.33-3.10 (m, 6H), 2.82 (d, J=16.2 Hz, 1H), 2.71 (s, 3H), 2.63 (d, J=14.6 Hz, 1H), 2.48-2.36 (m, 2H), 2.28 (d, J=12.5 Hz, 1H), 2.16 (s, 3H), 2.10 (s, 3H), 1.89-1.73 (m, 4H), 1.48-1.39 (m, 1H), 1.36-1.25 (m, 3H), 0.84-0.75 (m, 7H). HRESI-TOF m/z 1012.5177 (C$_{57}$H$_{69}$N$_7$O$_{10}$+H$^+$, required 1012.5178). [α]$_D^{23}$ −0.9 (c 0.5, CHCl$_3$).

Compound 41

A solution of 36 (0.7 mg, 0.007 mmol) and i-Pr$_2$NEt (1.5 µL, 0.0086 mmol) in CH$_2$Cl$_2$ (250 µL) was treated with a solution of propionyl chloride (0.80 mg, 0.0086 mmol) in CH$_2$Cl$_2$ (250 µL). The reaction was allowed to proceed overnight, after which time the mixture was loaded directly onto a PTLC plate and developed with 95:5:3 EtOAc: MeOH:NEt$_3$. The product was isolated as a white solid: 6.1 mg (83%). $^1$H NMR (500 MHz, CDCl$_3$) δ 9.82 (s, 1H), 8.00 (s, 1H), 7.70 (s, 1H), 7.48 (s, 1H), 7.23 (d, J=8.0 Hz, 2H), 7.20-7.04 (m, 4H), 6.63 (s, 1H), 6.11 (s, 1H), 5.94-5.77 (m, 1H), 5.47 (s, 1H), 5.34-5.23 (m, 1H), 5.00-4.70 (m, 4H), 4.39 (s, 1H), 3.95 (s, 1H), 3.87-3.79 (m, 7H), 3.74 (s, 1H), 3.51 (s, 3H), 3.37 (dd, J=15.7, 5.1 Hz, 2H), 3.33-3.04 (m, 5H), 2.82 (d, J=16.2 Hz, 1H), 2.72 (s, 3H), 2.66-2.59 (m, 1H), 2.52-2.34 (m, 4H), 2.28 (d, J=13.3 Hz, 1H), 2.23-2.14 (m, 1H), 2.10 (s, 3H), 1.92-1.71 (m, 4H), 1.38-1.28 (m, 2H), 1.28-1.22 (m, 5H), 0.96-0.85 (m, 1H), 0.83-0.75 (m, 6H). HRESI-TOF m/z 1026.5330 (C$_{58}$H$_{71}$N$_7$O$_{10}$+H$^+$, required 1026.5335). [α]$_D^{23}$ −3 (c 0.3, CHCl$_3$).

Compound 42

Yield: 7.9 mg (54%), white solid. $^1$H NMR (600 MHz, CDCl$_3$) δ 9.84 (s, 1H), 8.00 (s, 1H), 7.68 (s, 1H), 7.47 (s, 2H), 7.25-7.20 (m, 1H), 7.20-7.05 (m, 3H), 6.63 (s, 1H), 6.11 (s, 1H), 5.94-5.80 (m, 1H), 5.47 (s, 1H), 5.29 (d, J=10.2 Hz, 1H), 4.98-4.70 (m, 4H), 4.38 (s, 1H), 4.02-3.88 (m, 1H), 3.86-3.77 (m, 7H), 3.75 (s, 1H), 3.50 (s, 2H), 3.42-3.33 (m, 2H), 3.33-3.14 (m, 4H), 3.10 (q, J=7.3 Hz, 2H), 2.82 (d, J=16.0 Hz, 1H), 2.72 (s, 3H), 2.65-2.58 (m, 1H), 2.53-2.34 (m, 2H), 2.28 (d, J=14.1 Hz, 1H), 2.23-2.14 (m, 1H), 2.10 (s, 3H), 1.93-1.71 (m, 4H), 1.54-1.42 (m, 2H), 1.36-1.26 (m, 3H), 1.07 (dt, J=6.7, 3.5 Hz, 2H), 0.90-0.73 (m, 10H). HRESI-TOF m/z 1038.5331 (C$_{59}$H$_{71}$N$_7$O$_{10}$+H$^+$, required 1038.5335). [α]$_D^{23}$ −1 (c 0.3, CHCl$_3$).

Compound 43

A solution of 36 (0.7 mg, 0.007 mmol) and i-Pr$_2$NEt (1.5 µL, 0.0086 mmol) in CH$_2$Cl$_2$ (250 µL) was treated with a solution of iso-butyryl chloride (0.92 mg, 0.0086 mmol) in CH$_2$Cl$_2$ (250 µL). The reaction was allowed to proceed overnight, after which the mixture was loaded directly onto a PTLC plate and developed with 95:5:3 EtOAc:MeOH: NEt$_3$. The product was isolated as a white solid: 5.5 mg (74%). $^1$H NMR (500 MHz, CDCl$_3$) δ 9.82 (s, 1H), 8.00 (s, 1H), 7.70 (s, 1H), 7.47 (s, 1H), 7.26-7.16 (m, 3H), 7.16-7.03 (m, 3H), 6.63 (s, 1H), 6.11 (s, 1H), 5.85 (dd, J=9.0, 3.9 Hz, 1H), 5.47 (s, 1H), 5.29 (d, J=9.8 Hz, 1H), 4.94-4.76 (m, 4H), 4.39 (s, 1H), 4.00-3.89 (m, 1H), 3.84-3.78 (m, 7H), 3.74 (s, 1H), 3.50 (s, 3H), 3.37 (dd, J=16.1, 5.2 Hz, 2H), 3.31-3.14 (m, 4H), 3.09 (q, J=7.0 Hz, 2H), 2.82 (d, J=16.0 Hz, 1H), 2.72 (s, 3H), 2.65-2.59 (m, 1H), 2.55-2.35 (m, 3H), 2.28 (d, J=11.7 Hz, 1H), 2.22-2.14 (m, 1H), 2.10 (s, 3H), 1.89-1.73

(m, 4H), 1.37-1.28 (m, 2H), 1.27-1.22 (m, 8H), 0.86-0.74 (m, 7H). HRESI-TOF m/z 1040.5489 ($C_{59}H_{73}N_7O_{10}$+H$^+$, required 1040.5491). $[\alpha]_D^{23}$ −3 (c 0.2, CHCl$_3$).

Compound 44

A solution of 36 (0.7 mg, 0.007 mmol) and i-Pr$_2$NEt (1.5 μL, 0.0086 mmol) in CH$_2$Cl$_2$ (250 μL) was treated with a solution of trimethylacetyl chloride (1.0 mg, 0.0086 mmol) in CH$_2$Cl$_2$ (250 μL). The reaction was allowed to proceed overnight, after which the mixture was loaded directly onto a PTLC plate and developed with 95:5:3 EtOAc:MeOH:NEt$_3$. The product was isolated as a white solid: 5.5 mg (73%). $^1$H NMR (500 MHz, CDCl$_3$) δ 9.82 (s, 1H), 8.00 (s, 1H), 7.70 (s, 1H), 7.47 (d, J=8.5 Hz, 1H), 7.33 (s, 1H), 7.26-7.22 (m, 3H), 7.21-7.04 (m, 3H), 6.63 (s, 1H), 6.11 (s, 1H), 5.92-5.80 (m, 1H), 5.47 (s, 1H), 5.29 (d, J=9.6 Hz, 1H), 4.95-4.70 (i, 4H), 4.39 (s, 1H), 4.01-3.87 (m, 1H), 3.84-3.78 (m, 7H), 3.74 (s, 1H), 3.50 (s, 3H), 3.37 (dd, J=17.0, 5.3 Hz, 2H), 3.33-3.04 (m, 5H), 2.82 (d, J=16.2 Hz, 1H), 2.72 (s, 3H), 2.66-2.59 (m, 1H), 2.54-2.36 (m, 2H), 2.28 (d, J=16.8 Hz, 1H), 2.23-2.13 (m, 1H), 2.10 (s, 3H), 1.89-1.69 (m, 4H), 1.34-1.28 (m, 12H), 0.84-0.74 (m, 7H). HRESI-TOF m/z 1054.5647 ($C_{60}H_{75}N_7O_{10}$+H$^+$, required 1054.5648). $[\alpha]_D^{23}$ −6 (c 0.2, CHCl$_3$).

Compound 45

A solution of 36 (0.7 mg, 0.007 mmol) and i-Pr$_2$NEt (1.5 μL, 0.0086 mmol) in CH$_2$Cl$_2$ (250 μL) was treated with a solution of n-hexanoyl chloride (1.2 mg, 0.0086 mmol) in CH$_2$Cl$_2$ (250 μL). The reaction was allowed to proceed overnight, after which the mixture was loaded directly onto a PTLC plate and developed with 95:5:3 EtOAc:MeOH:NEt$_3$. The product was isolated as a white solid: 5.0 mg (66%). $^1$H NMR (500 MHz, CDCl$_3$) δ 9.82 (s, 1H), 8.01 (d, J=9.2 Hz, 1H), 7.69 (s, 1H), 7.47 (d, J=6.0 Hz, 1H), 7.23 (d, J=8.5 Hz, 2H), 7.19-6.99 (m, 4H), 6.63 (s, 1H), 6.11 (s, 1H), 5.85 (d, J=7.2 Hz, 1H), 5.47 (s, 1H), 5.29 (d, J=9.8 Hz, 1H), 4.95-4.67 (m, 4H), 4.39 (s, 1H), 3.94 (t, J=13.3 Hz, 1H), 3.81 (d, J=11.3 Hz, 7H), 3.74 (s, 1H), 3.51 (s, 3H), 3.37 (dd, J=16.0, 4.7 Hz, 2H), 3.33-3.12 (m, 4H), 3.09 (q, J=6.8 Hz, 1H), 2.82 (d, J=15.8 Hz, 1H), 2.72 (s, 3H), 2.63 (d, J=14.3 Hz, 1H), 2.50-2.24 (m, 4H), 2.18 (dt, J=14.3, 7.3 Hz, 1H), 2.10 (s, 3H), 1.88-1.67 (m, 5H), 1.50-1.27 (m, 8H), 0.90 (t, J=6.4 Hz, 4H), 0.79 (t, J=6.9 Hz, 7H). HRESI-TOF m/z 1068.5801 ($C_{60}H_{75}N_7O_{10}$+H$^+$, required 1068.5804). $[\alpha]_D^{23}$ −12 (c 0.2, CHCl$_3$).

Compound 46

A solution of 36 (0.7 mg, 0.007 mmol) and i-Pr$_2$NEt (1.5 μL, 0.0086 mmol) in CH$_2$Cl$_2$ (250 μL) was treated with a solution of acryloyl chloride (0.78 mg, 0.0086 mmol) in CH$_2$Cl$_2$ (250 μL). The reaction was allowed to proceed overnight, after which the mixture was loaded directly onto a PTLC plate and developed with 95:5:3 EtOAc:MeOH:NEt$_3$. The product was isolated as a white solid: 5.2 mg (71%). $^1$H NMR (500 MHz, CDCl$_3$) δ 9.82 (s, 1H), 8.00 (s, 1H), 7.76 (s, 1H), 7.50-7.44 (m, 1H), 7.40-7.32 (m, 2H), 7.25-7.04 (m, 4H), 6.63 (s, 1H), 6.42 (d, J=17.2 Hz, 1H), 6.24 (dd, J=16.8, 10.3 Hz, 1H), 6.11 (s, 1H), 5.85 (dd, J=9.7, 3.8 Hz, 1H), 5.76 (d, J=10.1 Hz, 1H), 5.47 (s, 1H), 5.29 (d, J=10.3 Hz, 1H), 4.96-4.74 (m, 4H), 4.39 (s, 1H), 4.01-3.89 (m, 1H), 3.89-3.76 (m, 8H), 3.74 (s, 1H), 3.51 (s, 3H), 3.37 (dd, J=16.0, 5.3 Hz, 2H), 3.33-3.12 (m, 5H), 3.08 (q, J=7.3 Hz, 1H), 2.82 (d, J=15.9 Hz, 1H), 2.72 (s, 3H), 2.65-2.59 (m, 1H), 2.50-2.35 (m, 2H), 2.28 (d, J=12.5 Hz, 1H), 2.23-2.13 (m, 1H), 2.10 (s, 3H), 1.90-1.70 (m, 4H), 1.37-1.28 (m, 3H), 0.83-0.76 (m, 7H). HRESI-TOF m/z 1024.5173 ($C_{60}H_{75}N_7O_{10}$+H$^+$ required 1024.5178). $[\alpha]_D^{23}$ −14 (c 0.2, CHCl$_3$).

Compound 47

Yield: 10.2 mg (69%), white solid. $^1$H NMR (600 MHz, CDCl$_3$) δ 9.84 (s, 1H), 8.00 (s, 1H), 7.74 (s, 1H), 7.47 (d, J=7.9 Hz, 1H), 7.35-7.27 (m, 2H), 7.23 (d, J=8.2 Hz, 1H), 7.20-7.04 (m, 3H), 7.03-6.93 (m, 1H), 6.63 (s, 1H), 6.11 (s, 1H), 5.94 (dt, J=15.1, 1.7 Hz, 1H), 5.89-5.80 (m, 1H), 5.47 (s, 1H), 5.29 (d, J=10.4 Hz, 1H), 4.96-4.69 (m, 4H), 4.39 (s, 1H), 4.00-3.88 (m, 1H), 3.85-3.77 (m, 7H), 3.74 (s, 1H), 3.51 (s, 3H), 3.42-3.32 (m, 2H), 3.32-3.09 (m, 5H), 2.82 (d, J=16.1 Hz, 1H), 2.71 (s, 3H), 2.64-2.55 (m, 1H), 2.51-2.35 (m, 2H), 2.34-2.23 (m, 1H), 2.23-2.14 (m, 1H), 2.10 (s, 3H), 1.90 (dd, J=7.0, 1.7 Hz, 3H), 1.87-1.72 (m, 4H), 1.49-1.41 (m, 1H), 1.37-1.26 (m, 3H), 0.83-0.75 (m, 7H). HRESI-TOF m/z 1038.5342 ($C_{59}H_{71}N_7O_{10}$+H$^+$, required 1038.5335). $[\alpha]_D^{23}$ +17 (c 0.5, CHCl$_3$).

Compound 48

Yield: 11.3 mg (76%), white solid. $^1$H NMR (600 MHz, CDCl$_3$) δ 9.84 (s, 1H), 8.00 (s, 1H), 7.74 (s, 1H), 7.47 (d, J=7.9 Hz, 1H), 7.26-7.18 (m, 2H), 7.18-7.03 (m, 4H), 6.63 (s, 1H), 6.11 (s, 1H), 5.92-5.78 (m, 1H), 5.75-5.64 (m, 1H), 5.47 (s, 1H), 5.29 (dt, J=10.1, 2.0 Hz, 1H), 4.92-4.75 (m, 4H), 4.38 (s, 1H), 4.00-3.89 (m, 1H), 3.85-3.78 (m, 7H), 3.74 (s, 1H), 3.51 (s, 3H), 3.43-3.34 (m, 2H), 3.33-3.11 (m, 5H), 2.82 (dt, J=16.1, 2.1 Hz, 1H), 2.71 (s, 3H), 2.65-2.59 (m, 1H), 2.50-2.35 (m, 2H), 2.32-2.24 (m, 1H), 2.21 (d, J=1.3 Hz, 3H), 2.20-2.14 (m, 1H), 2.10 (s, 3H), 1.89 (s, 3H), 1.87-1.74 (m, 4H), 1.52-1.43 (m, 1H), 1.37-1.25 (m, 3H), 0.84-0.75 (n, 7H). HRESI-TOF m/z 1052.5490 ($C_{60}H_{73}N_7O_{10}$+H$^+$, required 1052.5491). $[\alpha]_D^{23}$ +9 (c 0.5, CHCl$_3$).

Compound 49

Yield: 9.4 mg (60%), white solid. $^1$H NMR (600 MHz, CDCl$_3$) δ 9.84 (s, 1H), 8.00 (s, 1H), 7.80 (s, 1H), 7.74 (d, J=15.5 Hz, 1H), 7.62 (s, 1H), 7.58-7.50 (m, 2H), 7.47 (d, J=7.8 Hz, 1H), 7.43-7.32 (m, 4H), 7.26-7.23 (m, 1H), 7.20-7.03 (m, 3H), 6.63 (s, 1H), 6.57 (d, J=15.5 Hz, 1H), 6.11 (s, 1H), 5.85 (dd, J=10.8, 5.1 Hz, 1H), 5.47 (s, 1H), 5.29 (dt, J=10.1, 2.1 Hz, 1H), 4.97-4.72 (m, 4H), 4.41 (s, 1H), 3.94 (d, J=23.2 Hz, 1H), 3.87-3.76 (m, 7H), 3.74 (s, 1H), 3.52 (s, 3H), 3.42-3.33 (m, 2H), 3.33-3.09 (m, 5H), 2.82 (dt, J=16.1, 2.1 Hz, 1H), 2.71 (s, 3H), 2.64-2.57 (m, 1H), 2.51-2.36 (m, 2H), 2.33-2.23 (m, 1H), 2.23-2.14 (m, 1H), 2.10 (s, 3H), 1.90-1.71 (m, 4H), 1.50-1.40 (m, 1H), 1.35-1.24 (m, 3H), 0.85-0.75 (m, 7H). HRESI-TOF m/z 1000.5495 ($C_{64}H_{73}N_7O_{10}$+H$^+$, required 1000.5491). $[\alpha]_D^{23}$ +13 (c 0.4, CHCl$_3$).

Compound 50

A solution of 36 (16 mg, 0.016 mmol) in CH$_2$Cl$_2$ (0.5 mL) was treated with benzoyl chloride (2 μL, 0.018 mmol) and Et$_3$N (2.5 μL, 0.018 mmol). The reaction was allowed to proceed for 1 h before the mixture was loaded directly onto a PTLC plate (SiO$_2$) and developed with a 95:5:3 EtOAc:MeOH:NEt$_3$. The purified product was isolated as a white solid: 9.2 mg (54%). $^1$H NMR (500 MHz, CDCl$_3$) δ 9.82 (s, 1H), 8.00 (s, 1H), 7.91-7.83 (m, 3H), 7.81 (s, 1H), 7.60-7.52 (m, 1H), 7.52-7.46 (m, 3H), 7.41 (d, J=7.7 Hz, 1H), 7.30 (d, J=8.9 Hz, 1H), 7.16-7.03 (m, 3H), 6.64 (s, 1H), 6.12 (s, 1H), 5.84 (dd, J=9.2, 3.8 Hz, 1H), 5.48 (s, 1H), 5.29 (d, J=10.5 Hz, 1H), 5.01-4.79 (m, 4H), 4.41 (s, 1H), 4.02-3.91 (m, 1H), 3.91-3.85 (m, 1H), 3.82 (s, 3H), 3.80 (s, 3H), 3.74 (s, 1H), 3.52 (s, 3H), 3.43-3.34 (m, 2H), 3.33-3.12 (m, 5H), 2.82 (d, J=17.1 Hz, 1H), 2.72 (s, 3H), 2.62 (s, 1H), 2.50-2.36 (m, 2H), 2.30 (d, J=14.1 Hz, 1H), 2.24-2.15 (m, 1H), 2.10 (s, 3H), 1.92-1.75 (m, 4H), 1.39-1.23 (m, 3H), 0.88-0.74 (m, 7H). HRESI-TOF m/z 1074.5334 ($C_{62}H_{71}N_7O_{10}$+H$^+$, required 1074.5335). $[\alpha]_D^{23}$ −0.3 (c 0.4, CHCl$_3$).

Compound 51

Yield: 7.0 mg (43%), white solid. $^1$H NMR (600 MHz, CDCl$_3$) δ 9.84 (s, 1H), 8.04-7.82 (m, 5H), 7.77-7.68 (m, 2H), 7.68-7.59 (m, 2H), 7.55-7.37 (m, 5H), 7.31 (d, J=8.2 Hz, 1H), 7.22-7.03 (m, 3H), 6.64 (s, 1H), 6.12 (s, 1H), 5.92-5.77 (m, 1H), 5.48 (s, 1H), 5.30 (d, J=10.2 Hz, 1H), 5.02-4.74 (m, 4H), 4.42 (s, 1H), 4.05-3.88 (m, 1H), 3.87-3.77 (m, 7H), 3.75 (s, 1H), 3.53 (s, 3H), 3.43-3.33 (m, 2H), 3.33-3.08 (m, 5H), 2.83 (d, J=16.1 Hz, 1H), 2.72 (s, 3H), 2.66-2.60 (m, 1H), 2.50-2.37 (m, 2H), 2.30 (d, J=13.9 Hz, 1H), 2.24-2.14 (m, 1H), 2.11 (s, 3H), 1.91-1.70 (m, 4H), 1.51-1.43 (m, 1H), 1.37-1.27 (m, 3H), 0.85-0.77 (m, 7H). HRESI-TOF m/z 1150.5638 (C$_{68}$H$_{75}$N$_7$O$_{10}$+H$^+$, required 1150.5648). [α]$_D^{23}$ +0.8 (c 0.3, CHCl$_3$).

Compound 52

Yield: 10.5 mg (64%), white solid. $^1$H NMR (600 MHz, CDCl$_3$) δ 9.83 (s, 1H), 8.08-7.85 (m, 4H), 7.79 (s, 1H), 7.54-7.37 (m, 2H), 7.34-7.28 (m, 3H), 7.20-7.03 (m, 3H), 6.63 (s, 1H), 6.11 (s, 1H), 5.93-5.75 (m, 1H), 5.47 (s, 1H), 5.35-5.19 (m, 1H), 4.99-4.70 (m, 4H), 4.41 (s, 1H), 4.05-3.90 (m, 1H), 3.90-3.77 (m, 7H), 3.75 (s, 1H), 3.52 (s, 3H), 3.37 (dd, J=16.3, 5.2 Hz, 2H), 3.33-3.05 (m, 5H), 2.82 (d, J=16.0 Hz, 1H), 2.72 (s, 3H), 2.63 (d, J=16.7 Hz, 1H), 2.53-2.35 (m, 2H), 2.35-2.25 (m, 1H), 2.24-2.14 (m, 1H), 2.10 (s, 3H), 1.96-1.68 (m, 4H), 1.52-1.41 (m, 1H), 1.35-1.22 (m, 3H), 0.89-0.72 (m, 7H). HRESI-TOF m/z 1158.5155 (C$_{63}$H$_{70}$F$_3$N$_7$O$_{11}$+H$^+$, required 1158.5158). [α]$_D^{23}$ +6 (c 0.5, CHCl$_3$).

Compound 53

Yield: 10.3 mg (65%), white solid. $^1$H NMR (600 MHz, CDCl$_3$) δ 9.84 (s, 1H), 8.00 (s, 1H), 7.91-7.73 (m, 4H), 7.48 (d, J=7.7 Hz, 1H), 7.39 (d, J=8.2 Hz, 1H), 7.35-7.32 (m, 2H), 7.29 (d, J=8.3 Hz, 1H), 7.20-7.01 (m, 3H), 6.63 (s, 1H), 6.12 (s, 1H), 5.90-5.79 (m, 1H), 5.47 (s, 1H), 5.33-5.25 (m, 1H), 4.97-4.76 (m, 4H), 4.40 (s, 1H), 4.04-3.89 (m, 1H), 3.87-3.76 (m, 7H), 3.75 (s, 1H), 3.52 (s, 3H), 3.42-3.33 (m, 2H), 3.33-3.06 (m, 5H), 2.97 (hept, J=6.9 Hz, 1H), 2.82 (d, J=16.1 Hz, 1H), 2.72 (s, 3H), 2.65-2.57 (m, 1H), 2.51-2.35 (m, 2H), 2.35-2.24 (m, 1H), 2.23-2.13 (m, 1H), 2.10 (s, 3H), 1.93-1.70 (m, 4H), 1.46 (s, 1H), 1.37-1.25 (m, 9H), 0.87-0.73 (m, 7H). HRESI-TOF m/z 1116.5804 (C$_{65}$H$_{77}$N$_7$O$_{10}$+H$^+$, required 1116.5804). [α]$_D^{23}$ +21 (c 0.5, CHCl$_3$).

Compound 54

Yield: 7.6 mg (62%), white solid. $^1$H NMR (500 MHz, CDCl$_3$) δ 9.82 (s, 1H), 8.01 (s, 1H), 7.48 (d, J=7.8 Hz, 1H), 7.21-7.00 (m, 3H), 6.81 (s, 2H), 6.63 (s, 1H), 6.11 (s, 1H), 5.93-5.76 (m, 1H), 5.47 (s, 1H), 5.29 (d, J=10.1 Hz, 1H), 4.82 (q, J=12.1 Hz, 4H), 4.39 (s, 1H), 3.97-3.89 (m, 1H), 3.87 (s, 6H), 3.81 (d, J=7.2 Hz, 7H), 3.74 (s, 1H), 3.49 (s, 3H), 3.42-3.33 (m, 2H), 3.33-3.14 (m, 5H), 2.82 (d, J=16.5 Hz, 1H), 2.71 (s, 3H), 2.68-2.60 (m, 2H), 2.49-2.36 (m, 2H), 2.30 (d, J=15.2 Hz, 1H), 2.20 (dq, J=15.0, 8.2, 7.7 Hz, 1H), 2.10 (s, 3H), 1.87-1.76 (m, 3H), 1.30 (ddd, J=26.4, 12.7, 6.3 Hz, 4H), 0.79 (t, J=7.3 Hz, 7H). HRESI-TOF m/z 1015.5178 (C$_{57}$H$_{70}$N$_6$O$_{11}$+H$^+$, required 1015.5175). [α]$_D^{23}$ −3 (c 0.4, CHCl$_3$).

Compound 55

Yield: 8.6 mg (76%), white solid. $^1$H NMR (500 MHz, CDCl$_3$) δ 10.07 (s, 1H), 9.83 (s, 1H), 8.64-8.57 (m, 1H), 8.29 (dt, J=7.9, 1.1 Hz, 1H), 8.01 (s, 1H), 7.95 (s, 1H), 7.91 (td, J=7.7, 1.7 Hz, 1H), 7.56 (d, J=8.2 Hz, 1H), 7.52-7.44 (m, 2H), 7.32 (d, J=8.2 Hz, 1H), 7.18-7.03 (m, 3H), 6.64 (s, 1H), 6.12 (s, 1H), 5.84 (dd, J=10.2, 4.8 Hz, 1H), 5.48 (s, 1H), 5.29 (d, J=10.2 Hz, 1H), 4.99-4.76 (m, 4H), 4.41 (s, 1H), 3.96 (t, J=13.6 Hz, 1H), 3.90-3.77 (m, 7H), 3.74 (s, 1H), 3.52 (s, 3H), 3.43-3.33 (m, 2H), 3.34-3.08 (m, 5H), 2.82 (d, J=16.2 Hz, 1H), 2.72 (s, 3H), 2.65-2.59 (m, 1H), 2.49-2.36 (m, 2H), 2.34-2.25 (m, 1H), 2.24-2.14 (m, 1H), 2.10 (s, 3H), 1.91-1.70 (m, 4H), 1.54-1.44 (m, 1H), 1.41-1.26 (m, 3H), 0.86-0.74 (m, 7H). HRESI-TOF m/z 1075.5281 (C$_{61}$H$_{70}$N$_8$O$_{10}$+H$^+$, required 1075.5287). [α]$_D^{23}$ −7 (c 0.3, CHCl$_3$).

Compound 56

Yield: 5.5 mg (49%), white solid. $^1$H NMR (500 MHz, CDCl$_3$) δ 9.82 (s, 1H), 9.09 (d, J=2.3 Hz, 1H), 8.77 (dd, J=4.9, 1.6 Hz, 1H), 8.21 (dt, J=8.0, 2.0 Hz, 1H), 8.01 (s, 1H), 7.95 (s, 1H), 7.79 (s, 1H), 7.53-7.38 (m, 3H), 7.31 (d, J=8.2 Hz, 1H), 7.19-7.01 (m, 3H), 6.63 (s, 1H), 6.12 (s, 1H), 5.85 (dd, J=10.4, 4.8 Hz, 1H), 5.47 (s, 1H), 5.29 (d, J=10.2 Hz, 1H), 4.99-4.79 (m, 4H), 4.41 (s, 1H), 4.06-3.91 (m, 1H), 3.90-3.77 (m, 7H), 3.75 (s, 1H), 3.53 (s, 3H), 3.37 (dd, J=16.4, 5.3 Hz, 2H), 3.33-3.07 (m, 5H), 2.82 (d, J=16.1 Hz, 1H), 2.72 (s, 3H), 2.66-2.58 (m, 1H), 2.50-2.34 (m, 2H), 2.35-2.25 (m, 1H), 2.23-2.14 (m, 1H), 2.10 (s, 3H), 1.97-1.71 (m, 4H), 1.51-1.44 (m, 1H), 1.37-1.25 (m, 3H), 0.86-0.73 (m, 7H). HRESI-TOF m/z 1075.5287 (C$_{61}$H$_{70}$N$_8$O$_{10}$+H$^+$, required 1075.5287). [α]$_D^{23}$ −3 (c 0.2, CHCl$_3$).

Compound 57

Yield: 7.2 mg (64%), white solid. $^1$H NMR (500 MHz, CDCl$_3$) δ 9.81 (s, 1H), 8.80 (d, J=5.4 Hz, 2H), 8.01 (s, 1H), 7.94 (s, 1H), 7.80 (s, 1H), 7.71 (d, J=5.5 Hz, 2H), 7.48 (d, J=8.1 Hz, 1H), 7.42 (d, J=8.3 Hz, 1H), 7.32 (d, J=8.2 Hz, 1H), 7.19-7.03 (m, 3H), 6.64 (s, 1H), 6.12 (s, 1H), 5.90-5.78 (m, 1H), 5.47 (s, 1H), 5.29 (d, J=10.2 Hz, 1H), 4.99-4.75 (m, 4H), 4.41 (s, 1H), 4.03-3.87 (m, 1H), 3.87-3.76 (m, 7H), 3.75 (s, 1H), 3.52 (s, 3H), 3.45-3.33 (m, 2H), 3.33-3.06 (m, 5H), 2.82 (d, J=16.2 Hz, 1H), 2.72 (s, 3H), 2.65-2.59 (m, 1H), 2.52-2.35 (m, 2H), 2.29 (d, J=17.0 Hz, 1H), 2.24-2.14 (m, 1H), 2.10 (s, 3H), 1.97-1.73 (m, 4H), 1.51-1.44 (m, 1H), 1.37-1.26 (m, 3H), 0.85-0.75 (m, 7H). HRESI-TOF m/z 1075.5287 (C$_{61}$H$_{70}$N$_8$O$_{10}$+H$^+$, required 1075.5287). [α]$_D^{23}$ −1 (c 0.2, CHCl$_3$)

Compound 58

Yield: 18.1 mg (93%), pale yellow solid. $^1$H NMR (600 MHz, CDCl$_3$) δ 9.91 (s, 1H), 9.84 (s, 1H), 9.30 (d, J=1.4 Hz, 1H), 9.04 (d, J=5.0 Hz, 1H), 8.21 (dd, J=5.1, 1.4 Hz, 1H), 8.00 (s, 1H), 7.92 (s, 1H), 7.57 (d, J=8.2 Hz, 1H), 7.48 (d, J=8.0 Hz, 1H), 7.34 (d, J=8.2 Hz, 1H), 7.18-7.03 (m, 3H), 6.64 (s, 1H), 6.12 (s, 1H), 5.85 (dd, J=10.5, 4.8 Hz, 1H), 5.47 (s, 1H), 5.29 (d, J=10.2 Hz, 1H), 5.00-4.80 (m, 4H), 4.42 (s, 1H), 3.96 (t, J=13.5 Hz, 1H), 3.91-3.77 (m, 7H), 3.75 (s, 1H), 3.53 (s, 3H), 3.44-3.33 (m, 2H), 3.33-3.12 (m, 5H), 2.82 (d, J=16.1 Hz, 1H), 2.72 (s, 3H), 2.64 (d, J=13.9 Hz, 1H), 2.50-2.35 (m, 2H), 2.30 (d, J=14.1 Hz, 1H), 2.24-2.14 (m, 1H), 2.11 (s, 3H), 1.92-1.73 (m, 4H), 1.52-1.43 (m, 1H), 1.38-1.20 (m, 3H), 0.86-0.74 (m, 7H). HRESI-TOF m/z 1076.5238 (C$_{60}$H$_{69}$N$_9$O$_{10}$+H$^+$, required 1076.5240). [α]$_D^{23}$ −14 (c 0.8, CHCl$_3$).

Compound 59

Yield: 15.5 mg (80%), white solid. $^1$H NMR (600 MHz, CDCl$_3$) δ 9.83 (s, 1H), 9.34 (s, 1H), 9.23 (s, 2H), 8.44 (s, 1H), 8.05 (s, 1H), 7.79 (s, 1H), 7.46 (dd, J=16.6, 8.1 Hz, 2H), 7.29 (d, J=8.3 Hz, 1H), 7.15-7.05 (m, 3H), 6.63 (s, 1H), 6.11 (s, 1H), 5.91-5.80 (m, 1H), 5.46 (s, 1H), 5.29 (d, J=10.2 Hz, 1H), 4.97-4.78 (m, 4H), 4.42 (s, 1H), 3.96 (t, J=13.7 Hz, 1H), 3.87-3.76 (m, 7H), 3.74 (s, 1H), 3.51 (s, 3H), 3.42-3.33 (m, 2H), 3.32-3.11 (m, 5H), 2.82 (d, J=16.0 Hz, 1H), 2.71 (s, 3H), 2.62 (d, J=13.7 Hz, 1H), 2.48-2.36 (m, 2H), 2.28 (d, J=14.5 Hz, 1H), 2.22-2.14 (m, 1H), 2.10 (s, 3H), 1.89-1.71 (m, 4H), 1.50-1.42 (m, 1H), 1.37-1.24 (m, 3H), 0.89-0.74 (m, 7H). HRESI-TOF m/z 1076.5241 (C$_{60}$H$_{69}$N$_9$O$_{10}$+H$^+$, required 1076.5240). [α]$_D^{23}$ −24 (c 0.7, CHCl$_3$).

Compound 60

Yield: 6.7 mg (59%), white solid. $^1$H NMR (500 MHz, CDCl$_3$) δ 9.82 (s, 1H), 9.70 (s, 1H), 9.51 (d, J=1.5 Hz, 1H), 8.81 (d, J=2.5 Hz, 1H), 8.58 (dd, J=2.5, 1.5 Hz, 1H), 8.00 (s, 1H), 7.92 (s, 1H), 7.55 (d, J=8.3 Hz, 1H), 7.52-7.44 (m, 1H), 7.33 (d, J=8.3 Hz, 1H), 7.10 (dq, J=16.1, 7.9 Hz, 3H), 6.64 (s, 1H), 6.12 (s, 1H), 5.85 (dd, J=10.4, 4.8 Hz, 1H), 5.47 (s, 1H), 5.29 (d, J=10.2 Hz, 1H), 4.98-4.79 (m, 4H), 4.42 (s, 1H), 4.03-3.91 (m, 1H), 3.85-3.77 (m, 7H), 3.75 (s, 1H), 3.53 (s, 3H), 3.37 (dd, J=16.3, 5.7 Hz, 2H), 3.34-3.12 (m, 5H), 2.82 (d, J=16.2 Hz, 1H), 2.72 (s, 3H), 2.65-2.58 (m, 1H), 2.51-2.35 (m, 2H), 2.35-2.25 (m, 1H), 2.24-2.13 (m, 1H), 2.10 (s, 3H), 1.90-1.71 (m, 4H), 1.52-1.44 (m, 1H), 1.33 (dd, J=14.5, 7.2 Hz, 3H), 0.82-0.79 (m, 7H). HRESI-TOF m/z 1076.5242 ($C_{60}H_{69}N_9O_{10}$+H$^+$, required 1076.5240). $[\alpha]_D^{23}$ −10 (c 0.3, CHCl$_3$).

Compound 61

Yield: 8.2 mg (36%), white solid. $^1$H NMR (600 MHz, CDCl$_3$) δ 10.14 (s, 1H), 9.83 (s, 1H), 9.34 (dd, J=5.0, 1.7 Hz, 1H), 8.42 (dd, J=8.4, 1.7 Hz, 1H), 8.00 (s, 1H), 7.93 (s, 1H), 7.74 (dd, J=8.4, 5.0 Hz, 1H), 7.58 (d, J=8.6 Hz, 1H), 7.48 (d, J=8.0 Hz, 1H), 7.35 (d, J=8.2 Hz, 1H), 7.20-7.01 (m, 3H), 6.64 (s, 1H), 6.12 (s, 1H), 5.85 (ddd, J=10.3, 5.0, 1.6 Hz, 1H), 5.48 (s, 1H), 5.29 (dt, J=9.8, 2.0 Hz, 1H), 4.99-4.79 (m, 4H), 4.42 (s, 1H), 3.97 (t, J=14.1 Hz, 1H), 3.92-3.86 (m, 1H), 3.83 (s, 3H), 3.80 (s, 3H), 3.75 (s, 1H), 3.54 (s, 3H), 3.43-3.34 (m, 2H), 3.34-3.06 (m, 5H), 2.83 (d, J=16.1 Hz, 1H), 2.72 (s, 3H), 2.66-2.60 (m, 1H), 2.49-2.36 (m, 2H), 2.30 (d, J=15.2 Hz, 1H), 2.24-2.15 (m, 1H), 2.11 (s, 3H), 1.89-1.73 (m, 5H), 1.38-1.27 (m, 3H), 0.85-0.71 (m, 7H). HRESI-TOF m/z 1076.5248 ($C_{60}H_{69}N_9O_{10}$+H$^+$, required 1076.5240). $[\alpha]_D^{23}$ −10 (c 0.3, CHCl$_3$).

Compound 62

Yield: 6.6 mg (29%), white solid. $^1$H NMR (600 MHz, CDCl$_3$) δ 9.83 (s, 1H), 9.66 (s, 1H), 9.37 (dd, J=5.3, 1.2 Hz, 1H), 8.65 (s, 1H), 8.04 (s, 1H), 8.00-7.89 (m, 1H), 7.81 (s, 1H), 7.57-7.43 (m, 2H), 7.30 (d, J=8.2 Hz, 1H), 7.18-7.01 (m, 3H), 6.63 (s, 1H), 6.11 (s, 1H), 5.85 (ddd, J=10.2, 5.0, 1.6 Hz, 1H), 5.46 (s, 1H), 5.29 (d, J=10.2 Hz, 1H), 4.94-4.78 (m, 4H), 4.42 (s, 1H), 4.04-3.90 (m, 1H), 3.85-3.77 (m, 7H), 3.75 (s, 1H), 3.51 (s, 3H), 3.44-3.34 (m, 2H), 3.32-3.22 (m, 3H), 3.16 (d, J=12.0 Hz, 1H), 3.05 (q, J=7.4 Hz, 1H), 2.82 (d, J=16.0 Hz, 1H), 2.71 (s, 3H), 2.63 (d, J=13.7 Hz, 1H), 2.51-2.37 (m, 2H), 2.29 (d, J=14.1 Hz, 1H), 2.24-2.15 (m, 1H), 2.10 (s, 3H), 1.90-1.71 (m, 4H), 1.51-1.42 (m, 1H), 1.36-1.27 (m, 3H), 0.85-0.75 (m, 7H). HRESI-TOF m/z 1076.5242 ($C_{60}H_{69}N_9O_{10}$+H$^+$, required 1076.5240). $[\alpha]_D^{23}$ −4 (c 0.3, CHCl$_3$).

Compound 63

Yield: 9.7 mg (43%), white solid. $^1$H NMR (600 MHz, CDCl$_3$) δ 9.84 (s, 1H), 7.98 (s, 1H), 7.96 (s, 1H), 7.84 (s, 1H), 7.77 (s, 1H), 7.48 (d, J=7.9 Hz, 1H), 7.42 (d, J=8.1 Hz, 1H), 7.31 (d, J=8.2 Hz, 1H), 7.18-7.04 (m, 3H), 6.64 (s, 1H), 6.12 (s, 1H), 5.85 (ddd, J=10.2, 5.0, 1.6 Hz, 1H), 5.48 (s, 1H), 5.29 (dt, J=10.1, 2.0 Hz, 1H), 5.02-4.76 (m, 4H), 4.41 (s, 1H), 3.96 (t, J=13.5 Hz, 1H), 3.91-3.84 (m, OH), 3.82 (s, 3H), 3.80 (s, 3H), 3.75 (s, 1H), 3.53 (s, 3H), 3.41-3.34 (m, 2H), 3.34-3.26 (m, 1H), 3.27-3.20 (m, 2H), 3.17 (d, J=12.1 Hz, 2H), 2.82 (dt, J=16.2, 2.1 Hz, 1H), 2.72 (s, 3H), 2.63 (d, J=13.8 Hz, 1H), 2.49-2.36 (m, 2H), 2.29 (d, J=14.1 Hz, 1H), 2.24-2.15 (m, 1H), 2.11 (s, 3H), 1.89-1.73 (m, 2H), 1.50-1.41 (m, 1H), 1.37-1.24 (m, 2H), 0.83-0.73 (m, 7H). HRESI-TOF m/z 1065.5077 ($C_{59}H_{68}N_8O_{11}$+H$^+$, required 1065.5080). $[\alpha]_D^{23}$ −6 (c 0.4, CHCl$_3$).

Compound 64

Yield: 5.4 mg (49%), white solid. $^1$H NMR (500 MHz, CDCl$_3$) δ 9.81 (s, 1H), 8.04-7.94 (m, 3H), 7.85 (s, 1H), 7.82-7.74 (m, 1H), 7.48-7.38 (m, 2H), 7.31 (d, J=8.3 Hz, 1H), 7.22-7.05 (m, 3H), 6.71-6.52 (m, 1H), 6.12 (s, 1H), 5.89-5.83 (m, 1H), 5.50-5.40 (m, 1H), 5.30 (d, J=10.2 Hz, 1H), 4.94-4.79 (m, 4H), 4.38 (s, 1H), 3.99-3.89 (m, 1H), 3.87-3.77 (m, 7H), 3.76 (s, 1H), 3.72-3.51 (m, 5H), 3.43-3.25 (m, 4H), 3.10 (q, J=7.1, 6.4 Hz, 1H), 2.83 (d, J=18.5 Hz, 1H), 2.73 (s, 3H), 2.67-2.62 (m, 1H), 2.58-2.36 (m, 3H), 2.23-2.13 (m, 1H), 2.11 (s, 3H), 1.91-1.71 (m, 4H), 1.51-1.44 (m, 1H), 1.38-1.25 (m, 3H), 0.92-0.74 (m, 7H). HRESI-TOF m/z 1065.5085 ($C_{59}H_{68}N_8O_{11}$+H$^+$, required 1065.5080). $[\alpha]_D^{23}$ −10 (c 0.3, CHCl$_3$).

Compound 65

Yield: 10.4 mg (47%), white solid. $^1$H NMR (600 MHz, CDCl$_3$) δ 9.83 (s, 1H), 7.99 (s, 2H), 7.96 (s, 1H), 7.84 (s, 1H), 7.77 (s, 1H), 7.48 (d, J=7.9 Hz, 1H), 7.42 (d, J=8.3 Hz, 1H), 7.31 (d, J=8.3 Hz, 1H), 7.18-7.04 (m, 3H), 6.63 (s, 1H), 6.12 (s, 1H), 5.85 (ddd, J=10.2, 5.0, 1.6 Hz, 1H), 5.47 (s, 1H), 5.29 (dt, J=10.2, 2.0 Hz, 1H), 4.98-4.80 (m, 4H), 4.41 (s, 1H), 3.95 (t, J=13.7 Hz, 1H), 3.92-3.85 (m, 1H), 3.82 (s, 3H), 3.80 (s, 3H), 3.75 (s, 1H), 3.53 (s, 3H), 3.42-3.35 (m, 2H), 3.33-3.13 (m, 5H), 2.86-2.79 (m, 1H), 2.72 (s, 3H), 2.64 (d, J=13.5 Hz, 1H), 2.48-2.38 (m, 2H), 2.30 (d, J=13.7 Hz, 1H), 2.22-2.15 (m, 1H), 2.11 (s, 3H), 1.86-1.74 (m, 5H), 1.37-1.26 (m, 3H), 0.85-0.77 (m, 7H). HRESI-TOF m/z 1065.5100 ($C_{59}H_{68}N_8O_{11}$+H$^+$, required 1065.5080). $[\alpha]_D^{23}$ −6 (c 0.4, CHCl$_3$).

Compound 66

Yield: 6.3 mg (56%), white solid. $^1$H NMR (500 MHz, CDCl$_3$) δ 9.89 (s, 1H), 8.18 (s, 1H), 8.08 (s, 1H), 7.89 (s, 1H), 7.59 (s, 1H), 7.58-7.46 (m, 2H), 7.37 (d, J=8.2 Hz, 1H), 7.32 (d, J=3.4 Hz, 1H), 7.17 (d, J=7.8 Hz, 3H), 6.72 (s, 1H), 6.68-6.62 (m, 1H), 6.20 (s, 1H), 6.02-5.88 (m, 1H), 5.62-5.46 (m, 1H), 5.38 (d, J=10.3 Hz, 1H), 5.02-4.85 (m, 4H), 4.47 (s, 1H), 4.10-3.99 (m, 1H), 3.95-3.85 (m, 7H), 3.84 (s, 1H), 3.68-3.55 (m, 3H), 3.51-3.15 (m, 7H), 2.91 (d, J=16.1 Hz, 1H), 2.81 (s, 3H), 2.74-2.69 (m, 1H), 2.59-2.47 (m, 2H), 2.42-2.36 (m, 1H), 2.31-2.22 (m, 1H), 2.19 (s, 3H), 1.97-1.82 (m, 4H), 1.59-1.52 (m, 1H), 1.46-1.32 (m, 3H), 1.02-0.82 (m, 7H). HRESI-TOF m/z 1064.5133 ($C_{60}H_{69}N_7O_{11}$+H$^+$, required 1064.5128). $[\alpha]_D^{23}$ −4 (c 0.3, CHCl$_3$).

Compound 67

Yield: 7.1 mg (64%), white solid. $^1$H NMR (500 MHz, CDCl$_3$) δ 9.81 (s, 1H), 8.06 (s, 1H), 8.00 (s, 1H), 7.75 (s, 1H), 7.67-7.54 (m, 1H), 7.53-7.44 (m, 2H), 7.38 (d, J=8.0 Hz, 1H), 7.27 (s, 1H), 7.21-7.05 (m, 3H), 6.73 (s, 1H), 6.63 (s, 1H), 6.11 (s, 1H), 5.95-5.79 (m, 1H), 5.53-5.40 (m, 1H), 5.30 (d, J=10.3 Hz, 1H), 4.93-4.75 (m, 4H), 4.39 (s, 1H), 4.00-3.90 (m, 1H), 3.87-3.77 (m, 7H), 3.75 (s, 1H), 3.51 (s, 3H), 3.42-3.33 (m, 2H), 3.33-3.06 (m, 5H), 2.82 (d, J=16.5 Hz, 1H), 2.72 (s, 3H), 2.66-2.61 (m, 1H), 2.51-2.36 (m, 2H), 2.33-2.26 (m, 1H), 2.23-2.15 (m, 1H), 2.10 (s, 3H), 1.89-1.74 (m, 4H), 1.49-1.44 (m, 1H), 1.37-1.27 (m, 3H), 0.92-0.75 (m, 7H). HRESI-TOF m/z 1064.5128 ($C_{60}H_{69}N_7O_{11}$+H$^+$, required 1064.5128). $[\alpha]_D^{23}$ −6 (c 0.3, CHCl$_3$).

Compound 68

Yield: 7.6 mg (54%), white solid. $^1$H NMR (500 MHz, CDCl$_3$) δ 9.83 (s, 1H), 9.43 (s, 1H), 8.90 (d, J=1.4 Hz, 1H), 8.00 (s, 1H), 7.94-7.81 (m, 2H), 7.48 (d, J=7.1 Hz, 2H), 7.29 (d, J=8.3 Hz, 1H), 7.18-7.02 (m, 3H), 6.64 (s, 1H), 6.12 (s, 1H), 5.85 (dd, J=10.4, 4.7 Hz, 1H), 5.48 (s, 1H), 5.29 (d, J=10.3 Hz, 1H), 5.04 (s, 2H), 4.88 (p, J=13.7 Hz, 4H), 4.41 (s, 1H), 3.96 (t, J=13.7 Hz, 1H), 3.86-3.78 (m, 7H), 3.74 (s, 1H), 3.52 (s, 3H), 3.43-3.34 (m, 2H), 3.33-3.14 (m, 5H), 2.82 (d, J=16.2 Hz, 1H), 2.72 (s, 3H), 2.62 (s, 1H), 2.43 (dd, J=22.3, 11.1 Hz, 2H), 2.29 (d, J=13.9 Hz, 1H), 2.19 (dt, J=14.9, 7.7 Hz, 1H), 2.10 (s, 3H), 1.89-1.74 (m, 4H), 1.43-1.24 (m, 4H), 0.80 (t, J=7.3 Hz, 7H). HRESI-TOF m/z 1091.5345 ($C_{60}H_{70}N_{10}O_{10}$+H$^+$ required 1091.5349). $[\alpha]_D^{23}$ −7 (c 0.4, CHCl$_3$).

Compound 69

Yield: 8.8 mg (58%), white solid. $^1$H NMR (500 MHz, CDCl$_3$) δ 9.82 (s, 1H), 9.53 (s, 1H), 8.80 (s, 1H), 8.18 (s, 1H), 8.00 (s, 1H), 7.89 (s, 1H), 7.56-7.43 (m, 2H), 7.30 (d, J=8.2 Hz, 1H), 7.18-7.02 (m, 3H), 6.64 (s, 1H), 6.12 (s, 1H), 5.85 (dd, J=10.4, 4.7 Hz, 1H), 5.48 (s, 1H), 5.29 (d, J=10.2 Hz, 1H), 5.00-4.81 (m, 4H), 4.78 (s, 2H), 4.41 (s, 1H), 3.96 (t, J=13.7 Hz, 1H), 3.88-3.77 (m, 7H), 3.75 (s, 1H), 3.52 (s, 3H), 3.44-3.34 (m, 2H), 3.34-3.12 (m, 5H), 2.82 (d, J=16.2 Hz, 1H), 2.72 (s, 3H), 2.66-2.60 (m, 1H), 2.52-2.35 (m, 2H), 2.29 (d, J=14.0 Hz, 1H), 2.24-2.13 (m, 1H), 2.10 (s, 3H), 1.90-1.72 (m, 4H), 1.43-1.24 (m, 4H), 0.83-0.76 (m, 7H). HRESI-TOF m/z 1091.5345 ($C_{60}H_{70}N_{10}O_{10}$+H$^+$, required 1091.5349). $[\alpha]_D^{23}$ −15 (c 0.4, CHCl$_3$).

Compound 70

Yield: 10.1 mg (48%), white solid. $^1$H NMR (500 MHz, CDCl$_3$) δ 9.91-9.74 (m, 2H), 8.05 (d, J=8.5 Hz, 1H), 8.04-7.95 (m, 2H), 7.91 (s, 1H), 7.56-7.43 (m, 2H), 7.28 (d, J=0.8.4 Hz, 1H), 7.18-7.00 (m, 4H), 6.64 (s, 1H), 6.12 (s, 1H), 5.90-5.78 (m, 1H), 5.48 (s, 1H), 5.29 (d, J=10.2 Hz, 1H), 4.98-4.77 (m, 4H), 4.41 (s, 1H), 4.10 (s, 2H), 3.96 (t, J=13.6 Hz, 1H), 3.89-3.76 (m, 7H), 3.74 (s, 1H), 3.51 (s, 3H), 3.46-3.33 (m, 2H), 3.33-3.13 (m, 5H), 2.82 (d, J=16.2 Hz, 1H), 2.72 (s, 3H), 2.65-2.60 (m, 1H), 2.50-2.36 (m, 2H), 2.29 (d, J=14.1 Hz, 1H), 2.19 (dt, J=15.0, 8.2 Hz, 1H), 2.10 (s, 3H), 1.89-1.73 (m, 4H), 1.48 (s, 1H), 1.37-1.25 (m, 3H), 0.84-0.76 (m, 7H). HRESI-TOF m/z 1090.5378 ($C_{47}H_{57}N_5O_9$+H$^+$, required 1090.5396). $[\alpha]_D^{23}$ −5 (c 0.8, CHCl$_3$).

Cell Growth Inhibition Assay

Compounds were tested for their cell growth inhibition of L1210 (ATCC no. CCL-219, mouse lymphocytic leukemia) cells, HCT116 (ATCC no. CCL-247, human colorectal carcinoma) cells, and HCT116/VM46 (a vinblastine-resistant strain of HCT116) cells in culture. A population of cells (>1×10$^6$ cells/mL as determined with a hemocytometer) was diluted with an appropriate amount of Dulbecco's Modified Eagle Medium (DMEM, Gibco) containing 10% fetal bovine serum (FBS, Gibco) to a final concentration of 30000 cells/mL.

To each well of a 96-well plate (Corning Costar), 100 μL of the cell media solution was added with a multichannel pipet. The cultures were incubated at 37° C. in an atmosphere of 5% CO$_2$ and 95% humidified air for 24 hours. The test compounds were added to the plate as follows: test substances were diluted in DMSO to a concentration of 1 mM and 10-fold serial dilutions were performed on a separate 96-well plate. Fresh culture medium (100 μL) was added to each well of cells to constitute 200 μL of medium per well followed by 2 μL of each test agent. Compounds were tested in duplicate (n=2-18 times) at six concentrations between 0-1000 nM or 0-10000 nM. Following addition, cultures were incubated for an additional 72 hours.

A phosphatase assay was used to establish the IC$_{50}$ values as follows: the media in each cell was removed and 100 μL of phosphatase solution (100 mg phosphatase substrate in 30 mL of 0.1 M NaOAc, pH 5.5, 0.1% Triton X-100 buffer) was added to each well. The plates were incubated at 37° C. for either 5 minutes (L1210) or 15 minutes (HCT116 and HCT116/VM46). After the given incubation time, 50 μL of 0.1 N NaOH was added to each well and the absorption at 405 nm was determined using a 96 well plate reader. As the absorption is directly proportional to the number of living cells, the IC$_{50}$ values were calculated and the reported values represent of the average of 4-36 determinations (SD±10%).

BODIPY-Vinblastine/Tubulin Competitive Displacement Assay

100 μL of 1 mg/mL tubulin in PEM and 25 μL of 72 μM BODIPY-VBL in DMSO were added to 850 μL of buffer (PEM+1 mM GTP). The solution was incubated at 37° C. for 15 minutes, after which 25 μL of 720 μM competitive ligand in DMSO was added. The solution was incubated for an additional 60 minutes at 37° C., after which 100 μL aliquots of each incubation were transferred into the wells of a 96-well plate (warmed to 37° C. in the plate reader). The BODIPY-vinblastine fluorescence intensity was measured (Ex 480 nm, Em 514 nm, Cutoff 495 nm) at 37° C. Control measurements were performed with BODIPY-VBL (control 1) in the absence of a competitive ligand (maximum FI enhancement due to tubulin binding) and (control 2) in the absence of tubulin (no FI enhancement due to tubulin binding). % BODIPY-VBL displacement was calculated by the formula (Control 2 FI−Experiment FI)/(Control 2 FI−Control 1 FI)×100. PEM: 80 mM PIPES-K pH 6.8, 2 mM MgSO$_4$, 0.5 mM EGTA pH 6.8.

Synthesis of Isoindolines not Commercially Available

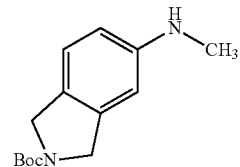 [SMILES: CNc1ccc2c(c1)CN(C(=O)OC(C)(C)C)C2]

tert-Butyl 5-(Methylamino)isoindoline-2-carboxylate

2-Boc-5-Aminoisoidoline (50 mg, 0.21 mmol) was added to a solution of NaOMe in MecOH (4 mL of 0.26 M, 1.05 mmol). This solution was then combined with a solution of paraformaldehyde (9.5 mg, 0.32 mmol) in MeOH (2 mL). The solution was stirred overnight (about 18 hours) at room temperature, after which time NaBH$_4$ (8 mg, 0.21 mmol) was added and the reaction mixture was heated at reflux for 5 hours. After cooling to room temperature, the reaction was quenched with the addition of saturated aq. NH$_4$Cl (1 mL), then diluted with water (about 20 mL) and extracted with CH$_2$Cl$_2$. The organic extracts were dried over Na$_2$SO$_4$. After removal of the solvent, the product was purified by flash chromatography (SiO$_2$, 15-45% EtOAc/hexanes gradient). Yield: 25.6 mg (52%), pale yellow oil, Mixture of rotamers. $^1$H NMR (400 MHz, CDCl$_3$) δ 7.04 and 6.09 (d, J=8.3 Hz, 1H), 6.73-6.45 (m, 2H), 4.72-4.47 (m, 4H), 3.52 (s, 1H), 1.50 (s, 9H). $^{13}$C NMR (151 MHz, CDCl$_3$) δ 148.0, 138.5, 123.6, 123.3, 113.6, 113.5, 107.1, 107.0, 79.7, 52.6, 52.3, 52.0, 51.6, 31.9, 31.8, 28.71, 28.67. HRESI-TOF m/z 249.1597 ($C_{14}H_{20}N_2O_2$+H$^+$, required 249.1597).

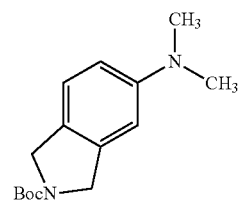 [SMILES: CN(C)c1ccc2c(c1)CN(C(=O)OC(C)(C)C)C2]

tert-Butyl 5-(Dimethylamino)isoindoline-2-carboxylate

A solution of 2-Boc-5-aminoisoidoline (50 mg, 0.21 mmol) and paraformaldehyde (64 mg, 2.1 mmol) in MeOH (1 mL) and HOAc (1 mL) was treated with NaCNBH$_3$ (72 mg, 1.05 mmol). The reaction was allowed to proceed for 6 hours, after which the mixture was diluted with water (about 20 mL). The pH value was adjusted to about 12 by the addition of concentrated aq. NaOH before the solution was extracted with CH$_2$Cl$_2$. The organic extracts were combined and dried over Na$_2$SO$_4$. Following removal of the solvent, the product was purified by flash chromatography (SiO$_2$, 20% EtOAc/hexanes). Yield: 35.6 mg (65%), pale yellow oil, mixture of rotamers. $^1$H NMR (400 MHz, CDCl$_3$) δ 7.13 and 7.08 (d, J=8.4 Hz, 1H), 6.82-6.46 (m, 2H), 4.77-4.45 (m, 4H), 3.06-2.85 (m, 6H), 1.51 (s, 9H). $^{13}$C NMR (151 MHz, CDCl$_3$) δ 154.2, 154.1, 150.0, 138.0, 137.6, 122.7, 122.4, 111.9, 106.1, 79.0, 52.2, 51.8, 51.3, 51.0, 40.6, 28.1. HRESI-TOF m/z 263.1755 (C$_{15}$H$_{22}$N$_2$O$_2$+H$^+$, required 263.1754).

General Method for the Synthesis of N-(Acyl)-5-aminoisoindolines

A solution of 2-Boc-5-aminoisoindoline (20 mg, 0.085 mmol) and a carboxylic acid (0.102 mmol) in DMF (1 mL) was treated with 1-[bis(dimethylamino)methylene]-1H-1,2,3-triazolo[4,5-b]pyridinium 3-oxid hexafluorophosphate (HATU; 39 mg, 0.102 mmol) and i-Pr$_2$NEt (17 μL, 0.102 mmol). The reaction was allowed to proceed overnight (about 18 hours), after which the solution was diluted with EtOAc (about 20 mL). The diluted reaction was extracted twice with saturated aq. NaHCO$_3$ and once with saturated aq. NaCl. The organic layer was dried over Na$_2$SO$_4$. The products were purified by flash chromatography (SiO$_2$) using an EtOAc/hexanes solvent gradient.

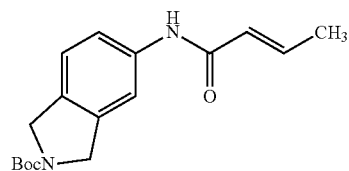 [SMILES: C/C=C/C(=O)Nc1ccc2c(c1)CN(C(=O)OC(C)(C)C)C2]

tert-Butyl (E)-5-(But-2-enamido)isoindoline-2-carboxylate

Yield: 20.1 mg (78%), white solid, mixture of rotamers. $^1$H NMR (600 MHz, CDCl$_3$) δ 7.75-7.55 (m, 1H), 7.51 (s, 1H), 7.42-7.22 (m, 1H), 7.17 and 7.14 (d, J=8.2 Hz, 1H), 7.05-6.92 (m, 1H), 5.97 and 5.95 (d, J=1.7 Hz, 1H), 4.79-4.40 (m, 4H), 1.90 (dd, J=6.9, 1.7 Hz, 3H), 1.51 (s, 9H). $^{13}$C NMR (151 MHz, CDCl$_3$) δ 164.2, 154.7, 141.8, 137.7, 125.5, 123.2, 123.0, 119.4, 114.5, 79.9, 52.5, 52.2, 52.1, 51.8, 28.7, 18.0. HRESI-TOF m/z 303.1702 (C$_{17}$H$_{22}$N$_2$O$_3$+H$^+$, required 303.1703).

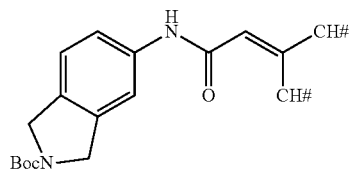

tert-Butyl 5-(3-Methylbut-2-enamido)isoindoline-2-carboxylate

Yield: 22.7 mg (85%), white solid, mixture of rotamers. $^1$H NMR (600 MHz, CDCl$_3$) δ 7.76-7.57 (m, 1H), 7.36 (s, 1H), 7.33-7.21 (m, 1H), 7.18 and 7.15 (d, J=1.7 Hz, 1H), 5.79-5.67 (m, 1H), 4.76-4.51 (m, 4H), 2.24 (d, J=1.2 Hz, 3H), 1.92 (d, J=1.3 Hz, 3H), 1.53 (s, 9H). $^{13}$C NMR (151 MHz, CDCl$_3$) δ 165.2, 154.7, 137.8, 123.1, 122.9, 119.2, 118.7, 114.3, 79.9, 52.5, 52.2, 52.1, 51.8, 28.7, 27.6, 20.1. HRESI-TOF m/z 317.1859 (C$_{18}$H$_{24}$N$_2$O$_3$+H$^+$, required 317.1860).

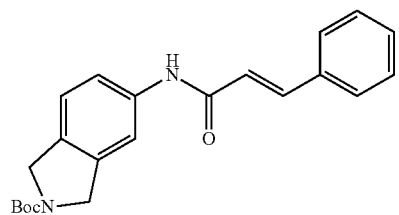 [SMILES: CC(C)(C)OC(=O)N1Cc2ccc(NC(=O)/C=C/c3ccccc3)cc2C1]

tert-Butyl 5-Cinnamamidoisoindoline-2-carboxylate

Yield: 24.8 mg (91%), white solid, mixture of rotamers. $^1$H NMR (600 MHz, CDCl$_3$) δ 7.95 (s, 1H), 7.78-7.70 (m, 2H), 7.55-7.28 (m, 6H), 7.22-7.10 (m, 1H), 6.61 and 6.59 (s, 1H), 4.73-4.50 (m, 4H), 1.52 (s, 9H). $^{13}$C NMR (151 MHz, CDCl$_3$) δ 164.3, 154.7, 142.5, 137.7, 134.7, 130.1, 129.0, 128.1, 123.2, 121.0, 119.5, 114.6, 79.9, 52.2, 52.1, 51.9, 28.7. HRESI-TOF m/z 340.1657 (C$_{19}$H$_{21}$N$_3$O$_3$+H$^+$, required 340.1656)

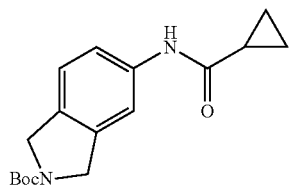 [SMILES: CC(C)(C)OC(=O)N1Cc2ccc(NC(=O)C3CC3)cc2C1]

tert-Butyl 5-(Cyclopropanecarboxamido)isoindoline-2-carboxylate

Yield: 23.2 mg (90%), white solid mixture of rotamers. $^1$H NMR (400 MHz, CDCl$_3$) δ 7.76 (s, 1H), 7.68-7.52 (m, 1H), 7.38-7.21 (m, 1H), 7.21-7.07 (m, 1H), 4.79-4.46 (m, 4H), 1.52 (s, 10H), 1.09 (p, J=4.2 Hz, 2H), 0.85 (dq, J=7.3, 4.0 Hz, 2H). $^{13}$C NMR (151 MHz, CDCl$_3$) δ 172.2, 154.7, 137.8, 123.1, 123.0, 119.1, 114.4, 79.9, 52.5, 52.2, 52.1, 51.8, 28.7, 15.8, 8.1. HRESI-TOF m/z 303.1703 (C$_{17}$H$_{22}$N$_2$O$_3$+H$^+$, required 303.1703).

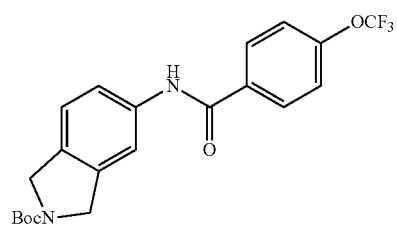 [SMILES: CC(C)(C)OC(=O)N1Cc2ccc(NC(=O)c3ccc(OC(F)(F)F)cc3)cc2C1]

tert-Butyl 5-(4-(Trifluoromethoxy)benzamido)isoindoline-2-carboxylate

Yield: 32.4 mg (90%), white solid, mixture of rotamers. $^1$H NMR (400 MHz, CDCl$_3$) δ 8.15 (s, 1H), 7.91 (d, J=8.6 Hz, 2H), 7.73-7.64 (m, 1H), 7.54-7.31 (m, 1H), 7.31-7.24 (m, 2H), 7.20 (d, J=8.3 Hz, 1H), 4.62 (s, 4H), 1.51 (s, 9H). $^{13}$C NMR (151 MHz, CDCl$_3$) δ 164.8, 154.6, 151.8, 137.3, 133.4, 129.2, 123.3, 123.2, 120.9, 119.9, 115.1, 80.0, 52.5, 52.2, 51.8, 28.7. HRESI-TOF m/z 423.1525 (C$_{21}$H$_{21}$F$_3$N$_2$O$_4$+H$^+$, required 423.1526).

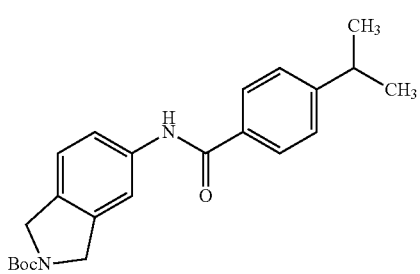 [SMILES: CC(C)c1ccc(C(=O)Nc2ccc3c(c2)CN(C(=O)OC(C)(C)C)C3)cc1]

tert-Butyl 5-(4-Isopropylbenzamido)isoindoline-2-carboxylate

Yield: 27.5 mg (85%), white solid, mixture of rotamers. $^1$H NMR (600 MHz, CDCl$_3$) δ 8.00 (s, 1H), 7.82-7.77 (m, 2H), 7.77-7.62 (m, 1H), 7.49-7.33 (m, 1H), 7.34-7.29 (m, 2H), 7.25-7.15 (m, 1H), 4.76-4.49 (m, 4H), 2.96 (hept, J=6.9 Hz, 1H), 1.52 (s, 9H), 1.27 (d, J=6.9 Hz, 6H). $^{13}$C NMR (151 MHz, CDCl$_3$) δ 165.9, 154.6, 153.4, 137.7, 132.5, 127.3, 127.0, 123.2, 123.1, 119.7, 119.6, 114.9, 114.8, 79.9, 52.5, 52.2, 52.1, 51.8, 34.3, 28.7, 28.6, 23.8, 23.86. HRESI-TOF m/z 381.2171 (C$_{23}$H$_{28}$N$_2$O$_3$+H$^+$, required 381.2173).

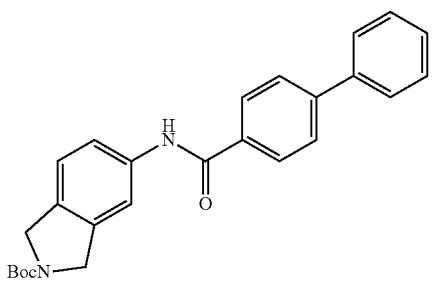 [SMILES: CC(C)(C)OC(=O)N1Cc2ccc(NC(=O)c3ccc(-c4ccccc4)cc3)cc2C1]

tert-Butyl 5-([1,1'-Biphenyl]-4-carboxamido)isoindoline-2-carboxylate

Yield: 32.1 mg (91%), white solid. $^1$H NMR (500 MHz, CDCl$_3$) δ 8.04-7.85 (m, 3H), 7.81-7.72 (m, 1H), 7.71-7.67 (m, 2H), 7.66-7.58 (m, 2H), 7.52-7.44 (m, 2H), 7.44-7.38 (m, 1H), 7.23 (s, 1H), 4.81-4.55 (m, 4H), 1.53 (s, 9H). $^{13}$C NMR (126 MHz, CDCl$_3$) δ 165.6, 154.7, 144.9, 140.0, 137.5, 133.6, 129.1, 128.3, 127.7, 127.6, 127.4, 119.7, 114.9, 79.9, 52.5, 52.3, 52.2, 51.9, 28.7. HRESI-TOF m/z 415.2015 (C$_{26}$H$_{26}$N$_2$O$_3$+H$^+$, required 415.2016).

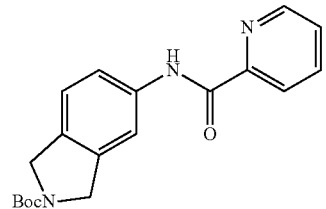 [SMILES: CC(C)(C)OC(=O)N1Cc2ccc(NC(=O)c3ccccn3)cc2C1]

tert-Butyl 5-(Picolinamido)isoindoline-2-carboxylate

Yield: 25.4 mg (88%), white solid, mixture of rotamers. $^1$H NMR (600 MHz, CDCl$_3$) δ 10.05 (s, 1H), 8.74-8.45 (m, 1H), 8.29 (d, J=7.8 Hz, 1H), 7.91 (td, J=7.7, 1.7 Hz, 1H), 7.87 and 7.83 (s, 1H), 7.64-7.44 (m, 2H), 7.24 (dd, J=26.7, 8.1 Hz, 1H), 4.78-4.57 (m, 4H), 1.52 (s, 9H). $^{13}$C NMR (151 MHz, CDCl$_3$) δ 162.1, 154.6, 149.8, 148.1, 138.6, 138.2, 137.9, 137.3, 133.3, 133.0, 126.6, 123.3, 123.1, 122.5, 119.2, 119.1, 114.2, 114.0, 79.9, 79.8, 52.5, 52.3, 52.2, 51.9, 28.7. HRESI-TOF m/z 340.1657 (C$_{19}$H$_{21}$N$_3$O$_3$+H$^+$, required 340.1656).

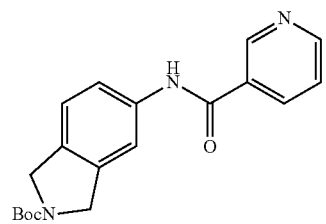 [SMILES: CC(C)(C)OC(=O)N1Cc2ccc(NC(=O)c3cccnc3)cc2C1]

tert-Butyl 5-(Nicotinamido)isoindoline-2-carboxylate

Yield: 27.0 mg (94%), white solid, mixture of rotamers. $^1$H NMR (600 MHz, CDCl$_3$) δ 9.09 (s, 1H), 8.74 (dt, J=4.8, 2.4 Hz, 1H), 8.51-8.33 (m, 1H), 8.21 (d, J=8.0 Hz, 1H), 7.78-7.61 (m, 1H), 7.53-7.33 (m, 2H), 7.25-7.17 (m, 1H), 4.69-4.56 (m, 4H), 1.51 (s, 9H). $^{13}$C NMR (151 MHz, CDCl$_3$) δ 164.2, 154.6, 152.61, 152.59, 148.12, 148.09, 138.60, 138.58, 138.2, 138.13, 137.16, 137.14, 135.5, 134.05, 134.03, 133.67, 133.64, 130.84, 130.81, 123.7, 123.4, 123.2, 120.1, 120.1, 115.3, 115.1, 80.00, 79.98, 52.5, 52.18, 52.14, 51.8, 28.7. HRESI-TOF m/z 340.1655 (C$_{19}$H$_{21}$N$_3$O$_3$+H$^+$, required 340.1656).

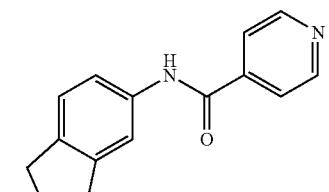

tert-Butyl 5-(Isonicotinamido)isoindoline-2-carboxylate

Yield: 24.1 mg (84%), white solid, mixture of rotamers. $^1$H NMR (600 MHz, CDCl$_3$) δ 8.82-8.69 (m, 2H), 8.37 (d, J=13.4 Hz, 1H), 7.83-7.60 (m, 3H), 7.54-7.32 (m, 1H), 7.26-7.19 (m, 1H), 4.69-4.55 (m, 4H), 1.51 (d, J=1.5 Hz, 9H). $^{13}$C NMR (151 MHz, CDCl$_3$) δ 164.0, 154.6, 150.8, 142.13, 142.10, 138.7, 138.2, 137.0, 136.9, 134.3, 133.9, 123.4, 123.2, 121.1, 120.0, 119.9, 115.2, 115.1, 80.1, 80.0, 52.5, 52.2, 52.1, 51.8, 28.7. HRESI-TOF m/z 340.1656 (C$_{19}$H$_{21}$N$_3$O$_3$+H$^+$, required 340.1656).

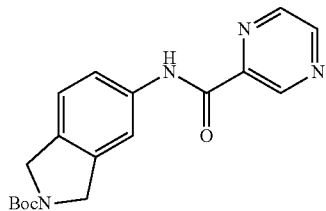 [SMILES: CC(C)(C)OC(=O)N1Cc2ccc(NC(=O)c3cnccn3)cc2C1]

tert-Butyl 5-(Pyrazine-2-carboxamido)isoindoline-2-carboxylate

Yield: 24.8 mg (86%), white solid, mixture of rotamers. $^1$H NMR (600 MHz, CDCl$_3$) δ 9.69 (s, 1H), 9.51 (s, 1H), 8.81 (d, J=2.4 Hz, 1H), 8.63-8.53 (m, 1H), 7.90-7.75 (m, 1H), 7.63-7.42 (m, 1H), 7.28-7.22 (m, 1H), 4.76-4.60 (m, 4H), 1.52 (d, J=2.2 Hz, 9H). $^{13}$C NMR (151 MHz, CDCl$_3$) δ 160.8, 154.6, 147.7, 144.8, 144.4, 142.5, 138.7, 138.3, 136.79, 136.76, 133.9, 133.6, 123.5, 123.3, 119.3, 114.4, 114.3, 79.9, 79.9, 52.5, 52.2, 52.1, 51.9, 28.7. HRESI-TOF m/z 341.1606 (C$_{18}$H$_{20}$N$_4$O$_3$+H$^+$, required 341.1608).

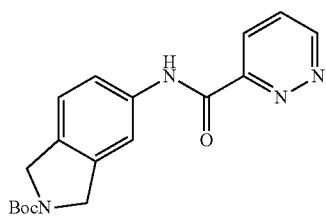 [SMILES: CC(C)(C)OC(=O)N1Cc2ccc(NC(=O)c3cccnn3)cc2C1]

tert-Butyl 5-(Pyridazine-3-carboxamido)isoindoline-2-carboxylate

Yield: 23.7 mg (82%), white solid, mixture of rotamers. $^1$H NMR (600 MHz, CDCl$_3$) δ 10.13 (s, 1H), 9.39 (s, 1H), 8.45 (d, J=8.4 Hz, 1H), 7.94-7.72 (m, 2H), 7.55 (t, J=6.3 Hz, 1H), 7.31-7.24 (m, 1H), 4.75-4.60 (m, 4H), 1.52 (s, 9H). $^{13}$C NMR (151 MHz, CDCl$_3$) δ 160.2, 154.6, 153.2, 136.7, 134.1, 128.4, 126.0, 123.5, 123.3, 119.4, 114.6, 114.3, 79.9, 52.5, 52.3, 52.2, 51.9, 28.7. HRESI-TOF m/z 341.1607 (C$_{18}$H$_{20}$N$_4$O$_3$+H$^+$, required 341.1608).

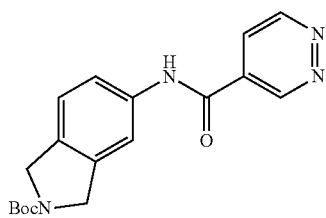 [SMILES: CC(C)(C)OC(=O)N1Cc2ccc(NC(=O)c3ccnnc3)cc2C1]

tert-Butyl 5-(Pyridazine-4-carboxamido)isoindoline-2-carboxylate

Yield: 21.5 mg (62%), white solid. $^1$H NMR (600 MHz, CDCl$_3$) δ 9.71 (s, 1H), 9.53-9.13 (m, 2H), 8.05 (s, 1H), 7.75 and 7.67 (s, 1H), 7.53 and 7.44 (d, J=8.2 Hz, 1H), 7.21 (t, J=9.3 Hz, 1H), 4.84-4.42 (m, 4H), 1.50 (s, 9H). $^{13}$C NMR (151 MHz, CDCl$_3$) δ 162.1, 154.7, 138.6, 138.1, 136.8, 134.6, 134.2, 123.5, 123.3, 120.4, 120.3, 115.5, 115.4, 80.2, 52.5, 52.2, 51.8, 28.7. HRESI-TOF m/z 341.1607 (C$_{18}$H$_{20}$N$_4$O$_3$+H$^+$, required 341.1608).

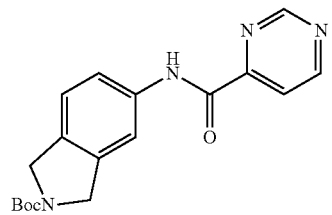

tert-Butyl 5-(Pyrimidine-4-carboxamido)isoindoline-2-carboxylate

Yield: 26.2 mg (91%), white solid, mixture of rotamers. $^1$H NMR (600 MHz, CDCl$_3$) δ 9.92 (s, 1H), 9.33 (s, 1H), 9.07 (d, J=5.0 Hz, 1H), 8.25 (dd, J=5.0, 1.4 Hz, 1H), 7.85 (s, 1H), 7.67-7.45 (m, 1H), 7.28 (s, 1H), 4.75-4.65 (m, 4H), 1.54 (s, 9H). $^{13}$C NMR (151 MHz, CDCl$_3$) δ 160.2, 159.6, 157.6, 156.4, 154.6, 136.5, 123.4, 119.4, 118.8, 114.4, 80.0, 52.3, 52.0, 28.7. HRESI-TOF m/z 341.1607 (C$_{18}$H$_{20}$N$_4$O$_3$+H$^+$, required 341.1608).

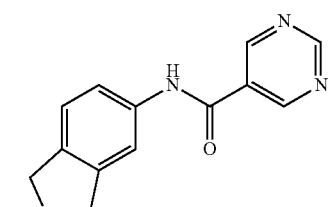

tert-Butyl-Pyrimidine-5-carboxamido)isoindoline-2-carboxylate

Yield: 25.0 mg (87%), white solid, mixture of rotamers. $^1$H NMR (600 MHz, CDCl$_3$) δ 9.35 (s, 1H), 9.30 (s, 2H), 8.70-8.55 (m, 1H), 7.75-7.60 (m, 1H), 4.51-7.39 (m, 1H), 7.25-7.16 (m, 1H), 4.76-4.51 (m, 4H), 1.51 (s, 9H). $^{13}$C NMR (151 MHz, CDCl$_3$) δ 161.8, 160.2, 156.0, 154.7, 138.2, 136.7, 128.7, 123.5, 123.3, 115.3, 80.1, 52.5, 52.2, 51.8, 28.7. HRESI-TOF m/z 341.1608 (C$_{18}$H$_{20}$N$_4$O$_3$+H$^+$, required 341.1608).

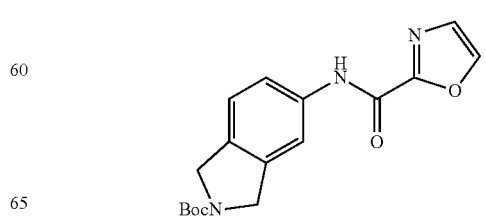

tert-Butyl 5-(Oxazole-2-carboxamido)isoindoline-2-carboxylate

Yield: 17.3 mg (62%), white solid, mixture of rotamers. $^1$H NMR (600 MHz, acetone-$d_6$) δ 9.61 (s, 1H), 8.30 (s, 1H), 7.86-7.69 (m, 2H), 7.62 (dt, J=8.2, 2.3 Hz, 1H), 7.26 (dd, J=11.4, 8.2 Hz, 1H), 4.70-4.38 (m, 4H), 1.45 (s, 9H). $^{13}$C NMR (151 MHz, acetone-$d_6$) δ 155.8, 154.7, 153.7, 146.7, 138.6, 131.0, 123.9, 120.6, 115.5, 79.6, 53.0, 52.8 52.6, 52.4, 38.7, 28.7. HRESI-TOF m/z 352.1266 ($C_{17}H_{19}N_3O_4$+Na$^+$, required 352.1268)

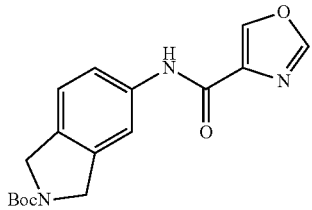

tert-Butyl 5-(Oxazole-4-carboxamido)isoindoline-2-carboxylate

Yield: 17.0 mg (61%), white solid, mixture of rotamers. $^1$H NMR (600 MHz, CDCl$_3$) δ 8.05 (s, 1H), 7.97 (s, 1H), 7.84 (s, 1H), 7.75-7.60 (m, 1H), 7.51-7.31 (m, 1H), 7.26-7.19 (m, 1H), 4.74-4.56 (m, 4H), 1.51 (d, J=1.2 Hz, 9H). $^{13}$C NMR (151 MHz, CDCl$_3$) δ 154.7, 154.6, 151.5, 145.5, 138.8, 138.4, 136.28, 136.25, 134.3, 134.0, 131.4, 123.5, 123.3, 119.7, 119.6, 114.9, 114.8, 80.01, 79.98, 52.5, 52.2, 52.1, 51.8, 28.7. HRESI-TOF m/z 330.1449 ($C_{17}H_{19}N_3O_4$+H$^+$, required 330.1449).

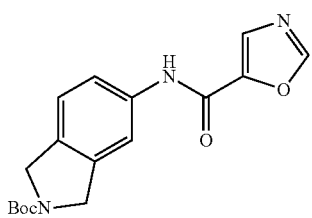 [SMILES: CC(C)(C)OC(=O)N1Cc2ccc(NC(=O)c3cnco3)cc2C1]

tert-Butyl 5-(Oxazole-5-carboxamido)isoindoline-2-carboxylate

Yield: 26.8 mg (95%), white solid, mixture of rotamers. $^1$H NMR (600 MHz, acetone-$d_6$) δ 9.75 (s, 1H), 8.44 (s, 1H), 8.05-7.81 (m, 2H), 7.76 (dt, J=8.6, 2.3 Hz, 1H), 7.40 (dd, J=10.9, 8.2 Hz, 1H), 4.87-4.54 (m, 4H), 1.59 (s, 9H). $^{13}$C NMR (151 MHz, acetone-$d_6$) δ 155.9, 154.8, 153.8, 146.8, 138.6, 131.1, 123.9, 120.6, 115.6, 79.7, 53.0, 52.8, 52.7, 52.4, 38.8, 28.7. HRESI-TOF m/z 352.1270 ($C_{17}H_{19}N_3O_4$+Na$^+$, required 352.1268).

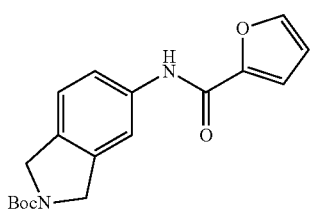 [SMILES: CC(C)(C)OC(=O)N1Cc2ccc(NC(=O)c3ccco3)cc2C1]

tert-Butyl 5-(Furan-2-carboxamido)isoindoline-2-carboxylate

Yield: 25.6 mg (94%), colorless oil, mixture of rotamers. $^1$H NMR (600 MHz, CDCl$_3$) δ 8.14 (s, 1H), 7.77-7.63 (m, 1H), 7.52-7.49 (m, 1H), 7.49-7.31 (m, 1H), 7.25-7.17 (m, 2H), 6.62-6.50 (m, 1H), 4.79-4.51 (m, 4H), 1.51 (d, J=1.8 Hz, 9H). $^{13}$C NMR (151 MHz, CDCl$_3$) δ 154.6, 147.8, 144.4, 138.6, 138.2, 136.93, 136.90, 133.6, 133.2, 123.3, 123.2, 119.40, 119.35, 115.5, 114.6, 114.5, 112.8, 79.90, 79.87, 52.5, 52.2, 52.1, 51.8, 28.7. HRESI-TOF m/z 329.1494 ($C_{18}H_{20}N_2O_4$+H$^+$, required 329.1496).

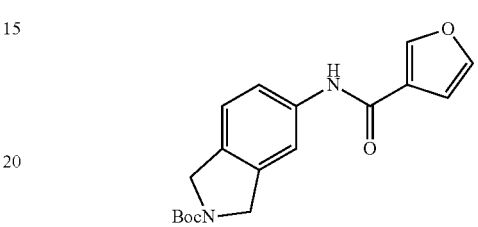

tert-Butyl 5-(Furan-3-carboxamido)isoindoline-2-carboxylate

Yield: 26.0 mg (92%), white solid, mixture of rotamers. $^1$H NMR (600 MHz, CDCl$_3$) δ 8.05 (s, 1H), 7.89 (d, J=10.5 Hz, 1H), 7.71-7.53 (m, 1H), 7.47-7.45 (m, 1H), 7.45-7.27 (m, 1H), 7.17 (dd, J=14.0, 8.2 Hz, 1H), 4.65-4.58 (m, 4H), 1.51 (d, J=1.7 Hz, 9H). $^{13}$C NMR (151 MHz, CDCl$_3$) δ 161.0, 154.7, 145.39, 145.37, 144.1, 138.5, 138.0, 137.3, 137.2, 133.5, 133.2, 123.2, 123.10, 123.06, 119.9, 119.8, 115.1, 115.0, 108.6, 79.98, 79.95, 52.5, 52.2, 52.1, 51.8, 28.7. HRESI-TOF m/z 329.1498 ($C_{18}H_{20}N_2O_4$+H$^+$, required 329.1496).

tert-Butyl 5-(5-Aminopicolinamido)isoindoline-2-carboxylate

Yield: 31.8 mg (98%), white solid, mixture of rotamers. $^1$H NMR (600 MHz, CDCl$_3$) δ 9.80 (s, 1H), 8.07 (d, J=8.5 Hz, 1H), 8.00 (t, J=3.2 Hz, 1H), 7.85 and 7.81 (s, 1H), 7.60-7.42 (m, 1H), 7.22 (dd, J=26.9, 8.3 Hz, 1H), 7.08 (dd, J=8.5, 2.7 Hz, 1H), 4.70-4.60 (m, 4H), 4.10 (s, 2H), 1.52 (s, 9H). $^{13}$C NMR (151 MHz, CDCl$_3$) δ 162.7, 154.7, 145.4, 140.3, 138.5, 137.8, 135.0, 132.7, 123.7, 123.2, 123.0, 121.4, 118.99, 118.95, 114.0, 113.8, 79.8, 52.6, 52.3, 52.2, 51.9, 28.7. HRESI-TOF m/z 355.1766 ($C_{19}H_{22}N_4O_3$+H$^+$, required 355.1765).

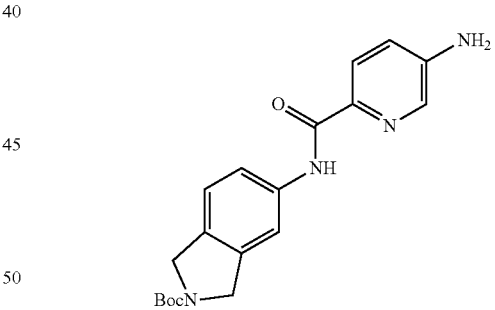

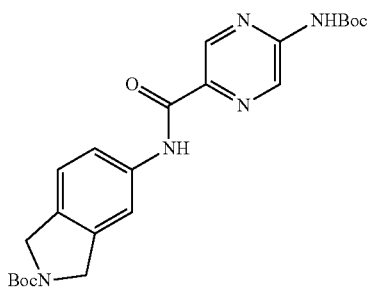 [SMILES: CC(C)(C)OC(=O)Nc1cnc(C(=O)Nc2ccc3c(c2)CN(C(=O)OC(C)(C)C)C3)cn1]

tert-Butyl 5-(5-((tert-Butyloxycarbonyl)amino)pyrazine-2-carboxamido)isoindoline-2-carboxylate The product precipitates from the reaction solution as a white solid and was isolated by filtration, rinsing with cold EtOAc. Further purification by flash chromatography was not necessary. Yield: 54.6 mg (94%), white solid. $^1$H NMR (400 MHz, CDCl$_3$) δ 9.58 (s, 1H), 9.30 (s, 1H), 9.11 (s, 1H), 8.18-7.97 (m, 1H), 7.82 (d, J=10.3 Hz, 1H), 7.59-7.45 (m, 1H), 7.22 (s, 1H), 4.85-4.53 (m, 4H), 1.59 (s, 9H), 1.52 (s, 9H). $^{13}$C NMR (151 MHz, CDCl$_3$) δ 161.0, 154.7, 151.6, 150.8, 142.6, 139.0, 137.1, 132.9, 123.4, 123.2, 119.3, 114.4, 114.2, 82.9, 79.9, 52.5, 52.3, 52.2, 51.9, 28.4. HRESI-TOF m/z 456.2240 (C$_{23}$H$_{29}$N$_5$O$_5$+H$^+$, required 456.2241).

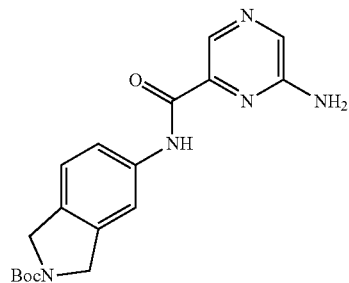 [SMILES: CC(C)(C)OC(=O)N1Cc2ccc(NC(=O)c3cncc(N)n3)cc2C1]

tert-Butyl 5-(6-Aminopyrazine-2-carboxamido)isoindoline-2-carboxylate

Yield: 56.2 mg (95%), white solid. $^1$H NMR (600 MHz, CDCl$_3$) δ 9.53 (s, 1H), 8.80 (s, 1H), 8.18 (s, 1H), 7.90-7.69 (m, 1H), 7.62-7.37 (m, 1H), 7.25-7.18 (m, 1H), 4.84 (s, 2H), 4.74-4.57 (m, 4H), 1.52 (d, J=2.1 Hz, 9H). $^{13}$C NMR (151 MHz, CDCl$_3$) δ 161.4, 154.7, 152.5, 141.4, 138.6, 138.2, 137.0, 136.0, 133.7, 133.6, 133.2, 123.3, 123.2, 119.2, 114.3, 114.2, 79.9, 52.5, 52.23, 52.15, 51.9, 28.7. HRESI-TOF m/z 356.1717 (C$_{18}$H$_{21}$N$_5$O$_3$+H$^+$, required 356.1717).

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A 20'-hydroxy-vinca derivative of structural Formula A or a pharmaceutically acceptable

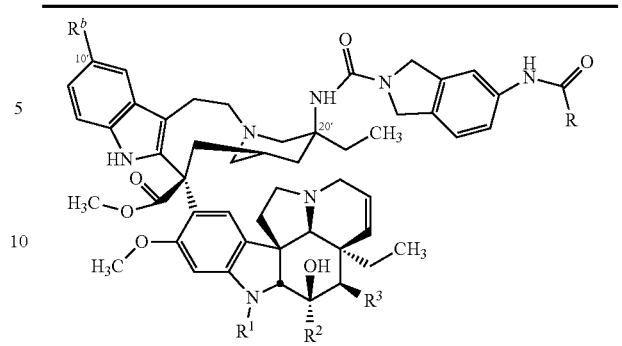

A

| | R$^1$ | R$^2$ | R$^3$ |
|---|---|---|---|
| Vinblastine | —CH$_3$ | —C(=O)—OCH$_3$ | —O—C(=O)—OCH$_3$ |
| Vincristine | —CH=O | —C(=O)—OCH$_3$ | —O—C(=O)—OCH$_3$ |
| Vindesine | —CH$_3$ | —C(=O)—NH$_2$ | —OH | salt thereof, wherein R is a substituent of the formula

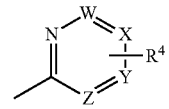

in which N is nitrogen and one of W, X, Y and Z can also be nitrogen (N), and when not nitrogen, W, X, Y and Z are CH or one of W, X, Y, Z is CR$^4$, and R$^4$ is hydrido or an electron donating substituent, and
R$^b$ is F or H.

2. The 20'-hydroxy-vinca derivative or salt according to claim 1, wherein one of W, X, Y and Z is nitrogen.

3. The 20'-hydroxy-vinca derivative or salt according to claim 2, wherein W is nitrogen.

4. The 20'-hydroxy-vinca derivative or salt according to claim 2, wherein X is nitrogen.

5. The 20'-hydroxy-vinca derivative or salt according to claim 2, wherein Y is nitrogen.

6. The 20'-hydroxy-vinca derivative or salt according to claim 2, wherein Z is nitrogen.

7. The 20'-hydroxy-vinca derivative or salt according to claim 1, wherein R has a structural formula of one or more of

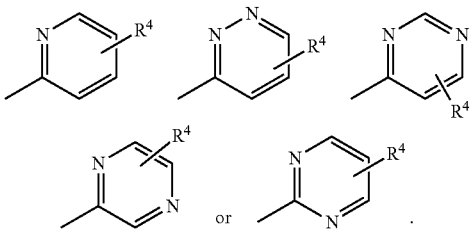

8. The 20'-hydroxy-vinca derivative or salt according to claim 7, wherein $R^4$ is hydrido or is selected from the group consisting of a $C_1$-$C_4$ hydrocarbyl, amino, mono-$C_1$-$C_4$ hydrocarbylamino, di-$C_1$-$C_4$ hydrocarbylamino and $C_1$-$C_4$ hydrocarbyloxy group.

9. The 20'-hydroxy-vinca derivative or salt according to claim 1, wherein $R^b$ is H.

10. The 20'-hydroxy-vinca derivative or salt according to claim 1 that is a derivative of vinblastine.

11. A 20'-substituted vinblastine of structural Formula B, or a pharmaceutically acceptable salt thereof

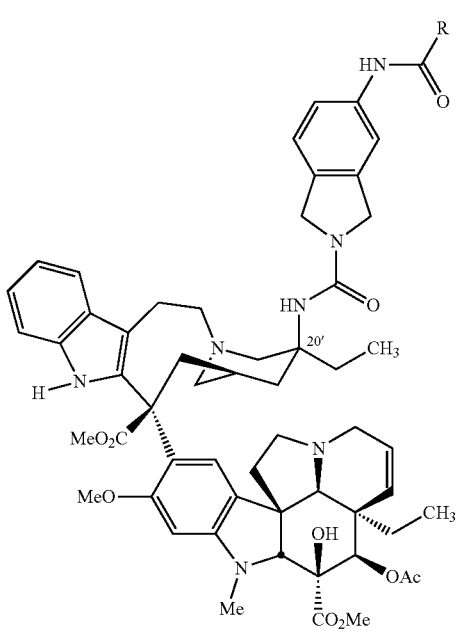

B wherein R is a substituent of the formula

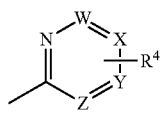

in which N is nitrogen and one of W, X, Y and Z can be nitrogen (N), and when not nitrogen, W, X, Y and Z are CH or one of W, X, Y, Z is $CR^4$, where $R^4$ is hydrido or is selected from the group consisting of one or more of a $C_1$-$C_4$ hydrocarbyl, amino, mono-$C_1$-$C_4$ hydrocarbylamino, di-$C_1$-$C_4$ hydrocarbylamino and $C_1$-$C_4$ hydrocarbyloxy group.

12. The 20'-substituted vinblastine or salt according to claim 11, wherein $R^4$ is amino.

13. The 20'-substituted vinblastine or salt according to claim 11, wherein R has a structural formula of one or more of

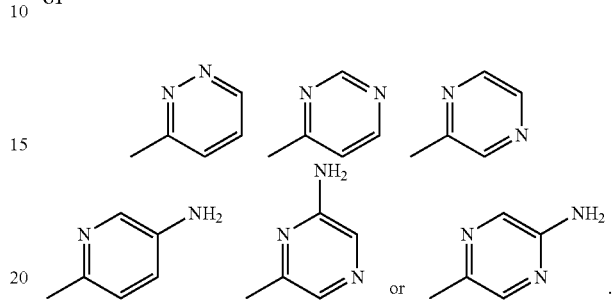

14. A pharmaceutical composition that comprises a cancerous cell proliferation-inhibiting amount of a 20'-hydroxy-vinca derivative compound of claim 1 or a pharmaceutically acceptable salt thereof dissolved or dispersed in a physiologically acceptable carrier.

15. The pharmaceutical composition according to claim 14, wherein a) one of W, X, Y and Z is nitrogen, b) $R^4$ is amino, and c) $R^b$ is H.

16. A method of inhibiting the growth of cancerous cells that comprises contacting said cancerous cells with a cancerous cell proliferation-inhibiting amount of a 20'-hydroxy-vinca derivative compound of claim 1 or a pharmaceutically acceptable salt thereof.

17. The method according to claim 16, wherein said cancerous cells are contacted a plurality of times.

18. The method according to claim 16, wherein said cancerous cells are contacted in vitro.

19. The method according to claim 16, wherein said contacted cancerous cells are leukemia cells.

20. The method according to claim 16, wherein said contacted cancerous cells are carcinoma cells.

21. The method according to claim 20, wherein said contacted carcinoma cells are resistant to vinblastine.

* * * * *